US012741938B2

(12) United States Patent
Liu et al.

(10) Patent No.: US 12,741,938 B2
(45) Date of Patent: Sep. 22, 2026

(54) CABOZANTINIB COMPOSITIONS AND METHODS OF USE

(71) Applicant: Handa Oncology, LLC, San Jose, CA (US)

(72) Inventors: Fang-Yu Liu, San Jose, CA (US); K.C. Sung, Tainan City (TW); Yu Zhang, Hangzhou (CN); Shang Wei Qin, Hangzhou (CN); John Duan, Tainan City (TW); George Kraft, San Jose, CA (US)

(73) Assignee: Handa Oncology, LLC, San Jose, CA (US)

( * ) Notice: Subject to any disclaimer, the term of this patent is extended or adjusted under 35 U.S.C. 154(b) by 0 days.

(21) Appl. No.: 19/444,948

(22) Filed: Jan. 9, 2026

(65) Prior Publication Data

US 2026/0138953 A1 May 21, 2026

Related U.S. Application Data

(63) Continuation of application No. 19/184,689, filed on Apr. 21, 2025, now Pat. No. 12,552,749, which is a continuation of application No. 18/938,926, filed on Nov. 6, 2024, now Pat. No. 12,415,784, which is a continuation of application No. PCT/US2024/013450, filed on Jan. 30, 2024.

(60) Provisional application No. 63/467,388, filed on May 18, 2023, provisional application No. 63/482,334, filed on Jan. 31, 2023.

(51) Int. Cl.

| | |
|---|---|
| ***C07D 215/22*** | (2006.01) |
| ***A61K 9/48*** | (2006.01) |
| ***A61K 31/47*** | (2006.01) |
| ***C07C 317/04*** | (2006.01) |

(52) U.S. Cl.

CPC .......... *C07D 215/22* (2013.01); *A61K 9/4816* (2013.01); *A61K 9/4825* (2013.01); *A61K 9/4858* (2013.01); *A61K 9/4866* (2013.01); *A61K 31/47* (2013.01); *C07C 317/04* (2013.01)

(58) Field of Classification Search

None

See application file for complete search history.

(56) References Cited

U.S. PATENT DOCUMENTS

| | | | |
|---|---|---|---|
| 7,579,473 | B2 | 8/2009 | Bannen et al. |
| 7,798,475 | B2 | 9/2010 | Demirbüker |
| 7,977,345 | B2 | 7/2011 | Bannen et al. |
| 8,067,436 | B2 | 11/2011 | Bannen et al. |
| 8,497,284 | B2 | 7/2013 | Bannen et al. |
| 8,585,942 | B2 | 11/2013 | Demirbüker |
| 8,585,943 | B2 | 11/2013 | Demirbüker |
| 8,673,912 | B2 | 3/2014 | Cannon et al. |
| 8,877,776 | B2 | 11/2014 | Brown et al. |
| 9,174,947 | B2 | 11/2015 | Bannen et al. |
| 9,365,516 | B2 | 6/2016 | Wilson et al. |
| 9,456,992 | B2 | 10/2016 | Brisander et al. |
| 9,717,720 | B2 | 8/2017 | Wilson et al. |
| 9,724,342 | B2 | 8/2017 | Wilson et al. |
| 9,809,549 | B2 | 11/2017 | Brown et al. |
| 9,815,789 | B2 | 11/2017 | Jetti et al. |
| 9,827,230 | B2 | 11/2017 | Brisander et al. |
| 9,833,442 | B2 | 12/2017 | Brisander et al. |
| 9,833,443 | B2 | 12/2017 | Brisander et al. |
| 9,861,624 | B2 | 1/2018 | Aftab |
| 9,969,692 | B2 | 5/2018 | Wilson et al. |
| 10,034,873 | B2 | 7/2018 | Wilson et al. |
| 10,039,757 | B2 | 8/2018 | Wilson et al. |
| 10,053,427 | B2 | 8/2018 | Stefinovic et al. |
| 10,080,723 | B2 | 9/2018 | Figueiredo et al. |
| 10,123,999 | B2 | 11/2018 | Wilson |
| 10,143,683 | B2 | 12/2018 | Brisander et al. |
| 10,159,666 | B2 | 12/2018 | Aftab et al. |
| 10,166,225 | B2 | 1/2019 | Aftab et al. |
| 10,206,916 | B2 | 2/2019 | Stefinovic et al. |
| 10,273,211 | B2 | 4/2019 | Aftab et al. |
| 10,314,830 | B2 | 6/2019 | Brisander et al. |
| 10,501,418 | B2 | 12/2019 | Aftab et al. |
| 10,543,206 | B2 | 1/2020 | Wilson et al. |
| 10,548,888 | B2 | 2/2020 | Wilson et al. |
| 10,736,886 | B2 | 8/2020 | Aftab et al. |

(Continued)

FOREIGN PATENT DOCUMENTS

| | | |
|---|---|---|
| CA | 3135464 | 4/2023 |
| CN | 103664776 | 3/2014 |

(Continued)

OTHER PUBLICATIONS

International Search Report for PCT/US2024/013450 dated May 31, 2024.

Written Opinion for PCT/US2024/013450 dated May 31, 2024.

Morcos et al., "Effects of the Wetting Agent Sodium Lauryl Sulfate on the Pharmacokinetics of Alectinib: Results from a Bioequivalence Study in Healthy Subjects" Clinical Pharmacology in Drug Development, vol. 6, No. 3, May 1, 2017, pp. 266-279.

Mallikarjun et al., "In-Vitro and Kinetic Studies of Immediate Release Sorafenib Tosylate Film Coated Tablets," World Journal of Pharmaceutical Research, vol. 7, May 1, 2018, pp. 931-944.

(Continued)

*Primary Examiner* — Sun Jae Yoo

(74) *Attorney, Agent, or Firm* — FLOREK & ENDRES PLLC

(57) ABSTRACT

The present invention relates to oral compositions comprising cabozantinib salts and at least one pharmaceutically acceptable excipient and methods of using the oral compositions to increase the oral bioavailability of the cabozantinib and reduce the adverse events associated with the oral administration of cabozantinib. The invention also relates to methods for preparing cabozantinib lauryl sulfate salts. The present invention further relates to polymorphic forms of cabozantinib lauryl sulfate salts, methods for preparing the polymorphic forms and uses thereof.

6 Claims, 11 Drawing Sheets

(56) References Cited

U.S. PATENT DOCUMENTS 10,851,061 B2 12/2020 Aftab et al.
10,940,149 B1 3/2021 Liu et al.
11,007,195 B2 5/2021 Liu et al.
11,052,088 B2 7/2021 Liu et al.
11,065,240 B2 7/2021 Aftab et al.
11,091,439 B2 8/2021 Brown et al.
11,091,440 B2 8/2021 Brown et al.
11,098,015 B2 8/2021 Brown et al.
11,124,481 B2 9/2021 Xu et al.
11,124,482 B2 9/2021 Bannen et al.
11,141,413 B2 10/2021 Aftab et al.
11,160,805 B2 11/2021 Liu et al.
11,261,160 B2 3/2022 Srinivasan et al.
11,279,675 B2 3/2022 Shah
11,433,064 B2 9/2022 Aftab et al.
11,498,902 B2 11/2022 Amala et al.
11,590,122 B2 2/2023 Dube et al.
11,679,105 B1 6/2023 Dube et al.
11,724,986 B2 8/2023 Aftab et al.
11,731,941 B2 8/2023 Shah
12,064,430 B2 8/2024 Liu et al.
2007/0054928 A1 3/2007 Bannen et al.
2009/0274693 A1 11/2009 Gilmer et al.
2010/0143459 A1 6/2010 Leipold et al.
2012/0070368 A1 3/2012 Bannen et al.
2012/0252840 A1 10/2012 Aftab et al.
2012/0270872 A1 10/2012 Cannon et al.
2012/0282179 A1 11/2012 Aftab et al.
2013/0030172 A1 1/2013 Wilson et al.
2013/0093111 A1 4/2013 Demirbüker et al.
2013/0143881 A1 6/2013 Cannon et al.
2013/0197230 A1 8/2013 Wilson et al.
2013/0330377 A1 12/2013 Wilson
2013/0337015 A1 12/2013 Wilson
2014/0044819 A1 2/2014 Demirbüker
2014/0057908 A1 2/2014 Smith et al.
2014/0057943 A1 2/2014 Smith et al.
2014/0066444 A1 3/2014 Smith et al.
2014/0121239 A1 5/2014 Aftab
2014/0179736 A1 6/2014 Schwab et al.
2014/0200242 A1 7/2014 Wilson
2014/0221372 A1 8/2014 Kulkarni et al.
2014/0228401 A1 8/2014 Aftab et al.
2014/0235631 A1 8/2014 Bunt et al.
2014/0256938 A1 9/2014 Wilson et al.
2014/0323522 A1 10/2014 Aftab et al.
2014/0330170 A1 11/2014 Holland
2014/0378454 A1 12/2014 Brisander et al.
2015/0133494 A1 5/2015 Aftab
2016/0022662 A1 1/2016 DeCillis
2016/0031818 A1 2/2016 Aftab
2016/0082019 A1 3/2016 Sweeney et al.
2016/0250153 A1 9/2016 Brisander et al.
2016/0361313 A1 12/2016 Brisander et al.
2017/0042828 A1 2/2017 Figueiredo et al.
2017/0044106 A1 2/2017 Aftab et al.
2017/0087143 A1 3/2017 Aftab et al.
2017/0143689 A1 5/2017 Wilson et al.
2017/0209372 A1 7/2017 Temtem et al.
2017/0217896 A1 8/2017 Xu et al.
2017/0224672 A1 8/2017 Aftab et al.
2017/0266178 A1 9/2017 Wilson et al.
2017/0281559 A1 10/2017 Chaudhary
2018/0042906 A1 2/2018 Brisander et al.
2018/0326078 A1 11/2018 Yang et al.
2019/0133935 A1 5/2019 Sommer et al.
2019/0167630 A1 6/2019 Bunt et al.
2019/0209547 A1 7/2019 Aftab et al.
2019/0262330 A1 8/2019 Schwab et al.
2019/0352403 A1 11/2019 Schwab et al.
2020/0113903 A1 4/2020 Liu et al.
2020/0188400 A1 6/2020 Liu et al.
2020/0255382 A1 8/2020 Schwab et al.
2020/0268737 A1 8/2020 Shah et al.
2020/0330451 A1 10/2020 Aftab et al.
2021/0030737 A1 2/2021 Tolaney et al.
2021/0046077 A1 2/2021 Liu et al.
2021/0161885 A1 6/2021 Wilson et al.
2021/0161895 A1 6/2021 Liu et al.
2021/0188776 A1 6/2021 Amala et al.
2021/0261509 A1 8/2021 Shah
2021/0275515 A1 9/2021 Apolo
2021/0283133 A1 9/2021 Liu et al.
2021/0315815 A1 10/2021 Ni et al.
2021/0332014 A1 10/2021 Chen et al.
2022/0265633 A1 8/2022 Dube et al.
2022/0280500 A1 9/2022 Dube et al.
2022/0362235 A1 11/2022 Dube et al.
2022/0387418 A1 12/2022 Dube et al.
2023/0142737 A1 5/2023 Liu et al.
2023/0149384 A1 5/2023 Schwab et al.
2023/0181559 A1 6/2023 Aftab et al.
2024/0366603 A1 11/2024 Liu et al.
2025/0049797 A1 2/2025 Liu et al.
2025/0057841 A1 2/2025 Liu et al.

FOREIGN PATENT DOCUMENTS

CN 107556238 1/2018
WO 2008055966 5/2008
WO 2013055996 4/2013
WO 2016020697 2/2016
WO 2019241504 12/2019
WO WO-2019241504 A1 * 12/2019 ............. A61P 35/02
WO 2022115464 6/2022
WO 2022177983 8/2022
WO 2023088284 5/2023
WO 2023165948 9/2023
WO 2023179774 9/2023
WO 2024114710 6/2024
WO 2024163400 8/2024

OTHER PUBLICATIONS

Cabometyx Package Insert Dec. 2017.

Cometriq Package Insert Oct. 2017.

Liu et al., "Improving Oral Bioavailability of Sorafenib by Optimizing the "Spring" and "Parachute" Based on Molecular Interaction Mechanism," Mol. Pharm.Feb. 2016. 1:13(2): 599-608.

Sharma et al., "The Concomitant Use of Tyrosine Kinase Inhibitors and Proton Pump Inhibitors: Prevalence, Predictors, and Impact on Survival and Discontinuation of Therapy in Older Adults with Cancer," Jan. 2019.

BASF Brochure Solubility Enhancement with BASF Pharma Polymers, Oct. 2011.

Capmul Technical Data Sheet Feb. 14, 2014.

BASF Brochure Pharma Solution Product Overview Dec. 2018. 2017.

Capmul Brochure Dec. 2015.

Sharma, M., et al. "The Prevalence and Predictors of Concomitant use of Tyrosine Kinase Inhibitors and Proton Pump Inhibitors in Older Adults with Cancer: An Observational Study Using Seer-Medicare Data." Value in Health 21 (2018): S19.

Abitec Personal Care Products Brochure, downloaded Jun. 25, 2020.

Abitec Food, Flavor & Nutrition Brochure, downloaded Jun. 25, 2020.

K.C. Panigrahi, et al., "Gelucire: A Versatile Polymer for Modified Release Drug Delivery System," Future Journal of Pharmaceutical Sciences (Nov. 2017), https://doi.org/10.1016/j.fjps.2017.11.001.

Daublain, et al. "Analyzing the Potential Root Causes of Variability of Pharmacokinetics in Preclinical Species," Mol Pharm. Mar. 2017;14:1634-45. doi:10.1021/acs.molpharmaceut.6b01118.

Fleisher et al., "Drug, Meal and Formulation Interactions Influencing Drug Absorption After Oral Administration," Clin Pharmacokinet. Mar. 1999;36:233-54.

Charman et al., Physicochemical and Physiological Mechanisms for the Eeffects of Food on Drug Absorption: the Role of pH and Llipids, J Pharm Sci. Mar. 1997;86:269-82.

(56) References Cited

OTHER PUBLICATIONS

Chen, Mei-Ling, "Lipid Excipients and Delivery Systems for Pharmaceutical Development: A Regulatory Perspective," Advanced Drug Delivery Reviews, Nov. 2007, 60 (6), pp. 768-777. DOI: 10.1016/j.addr.2007.09.010.

Porter et al., "Lipids and lipid-Based Formulations: Optimizing the Oral Delivery of Lipophilic Drugs," Nature Reviews. Drug Discovery, Mar. 2007, 6 (3), pp. 231-248. DOI: 10.1038/nrd2197.

Guidance for Industry Food-Effect Bioavailability and Fed Bioequivalence Studies. https://www.fda.gov/downloads/Drugs/GuidanceComplianceRegulatoryInformation/Guidances/UCM070241.pdf, Dec. 2002.

Kasashima et al. "Oral Sustained-Release Suspension Based on a Lauryl Sulfate Salt/Complex," International Journal of Pharmaceutics, 2016, pp. 677-683 (available online Oct. 17, 2016).

Kasashima et al., "Oral Sustained Release of a Hydrophilic Drug Using the Lauryl Sulfate Salt/Complex," Chem. Pharm. Bull. May 2016; 64(9); pp. 1304-1309 (Abstract).

Kasashima et al., "Oral Sustained Release of a Hydrophilic Drug Using the Lauryl Sulfate Salt/Complex," Chem. Pharm. Bull. May 2016; 64(9); pp. 1304-1309.

O'Brien "Small Molecule Kinase Inhibitors Approved by the FDA From 2000 to 2011: A Systematic Review of Preclinical ADME Data," Expert Opinion on Drug Metabolism & Toxicology, 9:12, 1597-1612, Aug. 31, 2013.

* cited by examiner

Effect of oral Cabozantinib on body weight in Wistar rats ($\bar{x} \pm$ SE, n=10)

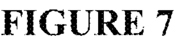
FIGURE 7
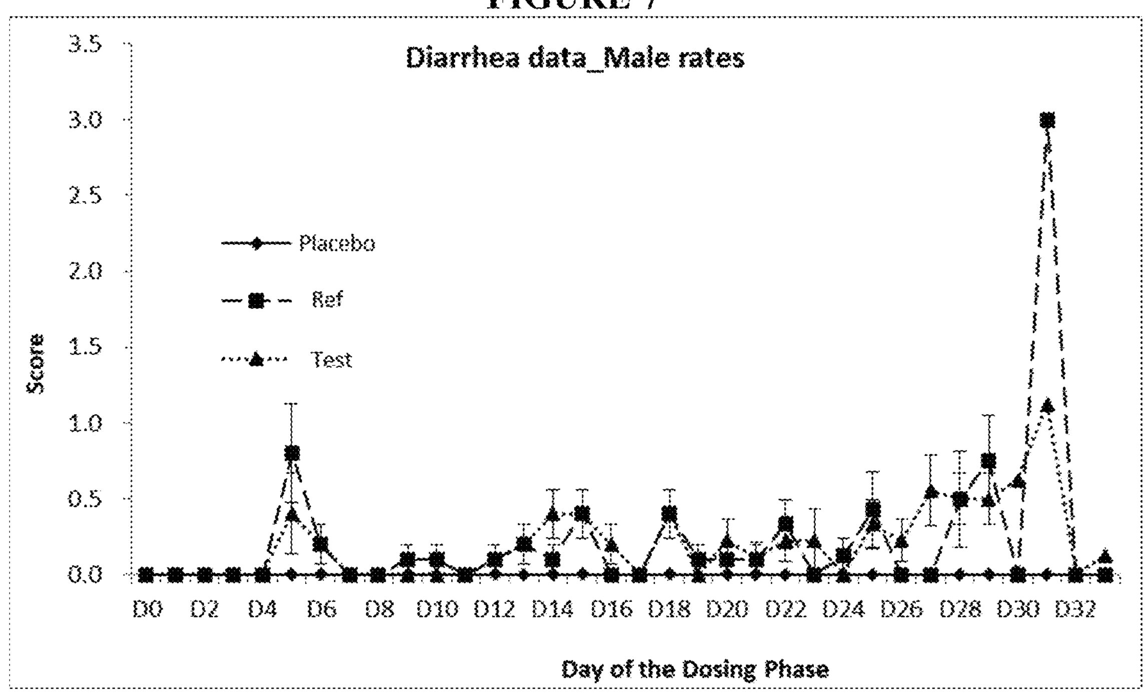
Effect of oral Cabozantinib on Diarrhea score in wistar rats ($\bar{x}$ ± SEM, n=10)
FIGURE 8
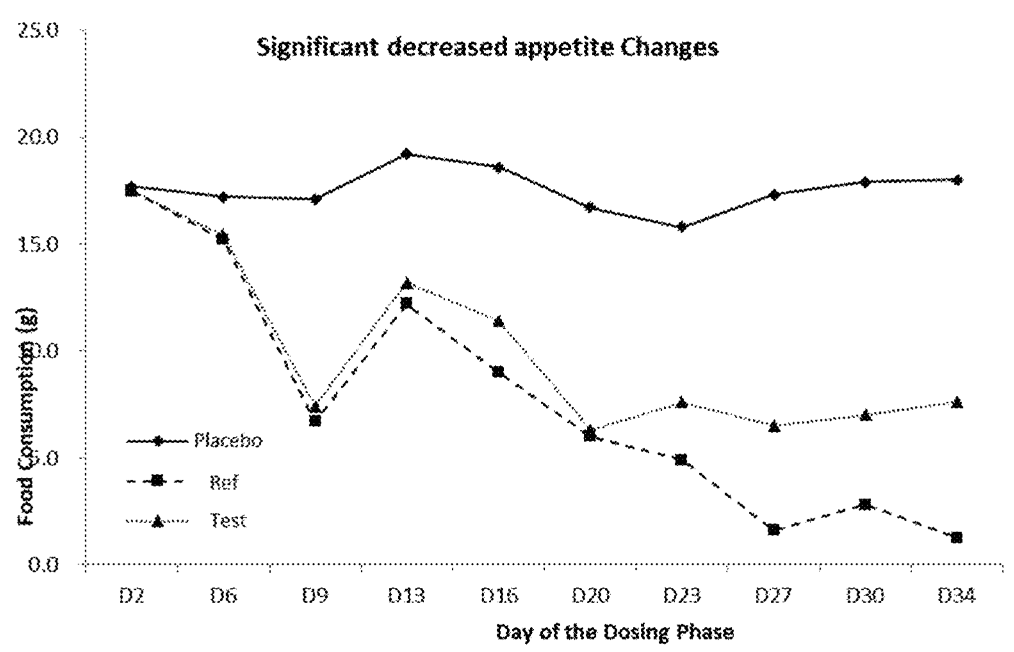
Effect of oral Cabozantinib on food intake in wistar rats ($\bar{x}$ ± SEM, n=10)

Effect of oral Cabozantinib on Survival Functions in wistar rats ($\bar{x}$ ± SEM, n=10)

CABOZANTINIB COMPOSITIONS AND METHODS OF USE

This application is a continuation of U.S. patent application Ser. No. 19/184,689 filed on Apr. 21, 2025, which is a continuation application of U.S. patent application Ser. No. 18/938,926 filed Nov. 6, 2024, now U.S. Pat. No. 12,415,784, which is a continuation of International Patent Application No. PCT/US2024/013450 filed on Jan. 30, 2024 which claims the benefits of U.S. Provisional Patent Application Ser. No. 63/482,334, filed on Jan. 31, 2023 and U.S. Provisional Patent Application Ser. No. 63/467,388, filed on May 18, 2023, each of which is herein incorporated by reference in its entirety.

FIELD OF THE INVENTION

The present invention relates to cabozantinib compositions and methods of using the compositions. The cabozantinib compositions may be orally administered to subjects in combination with one or more pharmaceutically acceptable excipients. In certain embodiments, the present invention relates to oral dosage forms comprising the mono- or di-lauryl sulfate salts of cabozantinib and one or more pharmaceutically acceptable excipient, and methods of treating various conditions such as cancer comprising the oral administration of the dosage forms.

The present invention further relates to methods for preparing cabozantinib lauryl sulfate salts and polymorphic forms thereof.

BACKGROUND

Cabozantinib lauryl sulfate salts are described in International Patent Application No. PCT/US2019/036947 filed on Jun. 13, 2019 and published as WO 2019/241504 and U.S. patent application Ser. No. 18/096,598 filed on Jan. 13, 2023. These patent applications also describe pharmaceutical compositions containing cabozantinib lauryl sulfate salts and methods of treating various conditions with the oral administration of the cabozantinib lauryl sulfate salts. The contents of WO 2019/241504 and U.S. patent application Ser. No. 18/096,598 filed on Jan. 13, 2023 are incorporated herein by reference.

Cabozantinib and various pharmaceutically acceptable salts other than the lauryl sulfate salt are described in numerous literature references such as U.S. Pat. Nos. 7,579,473 and 8,877,776. Pharmaceutical compositions containing cabozantinib and cabozantinib malate salt are also described for example in U.S. Pat. Nos. 9,724,342, 10,034,873 and 11,091,439.

Cabozantinib, in the form of capsules and tablets containing cabozantinib (S)-malate salt, is currently approved by the U.S. Food and Drug Administration (hereinafter "U.S. FDA") for treating various cancers such as renal cell carcinoma, hepatocellular carcinoma and medullary thyroid cancer. More specifically, cabozantinib is currently marketed as CABOMETYX® film coated tablets and COMETRIQ® capsules.

The CABOMETYX® tablets contain 20, 40 or 60 mg of cabozantinib free base (i.e., 25 mg, 51 mg or 76 mg of cabozantinib (S)-malate), microcrystalline cellulose, lactose anhydrous, hydroxypropyl cellulose, croscarmellose sodium, colloidal silicon dioxide, and magnesium stearate. The film coating contains hypromellose, titanium dioxide, triacetin, and iron oxide yellow. The U.S. FDA approved prescribing information (package insert or labeling) indicates the CABOMETYX® tablets can be used to treat patients with advanced renal cell carcinoma; patients with advanced renal cell carcinoma, as a first-line treatment in combination with nivolumab and patients with hepatocellular carcinoma who have been previously treated with sorafenib. The U.S. FDA prescribing information further indicates the recommended dose is 60 mg once daily and 40 mg once daily, administered in combination with nivolumab 240 mg every 2 weeks or 480 mg every 4 weeks. The U.S. FDA prescribing information also indicates that CABOMETYX® should be administered at least 1 hour before or at least 2 hours after eating because administration with food, particularly a high fat meal, can increase the $C_{max}$ and AUC of cabozantinib by 41% and 57%, respectively, relative to fasted conditions in healthy subjects administered a single oral dose of cabozantinib (S)-malate capsule formulation.

The COMETRIQ® capsules are hard gelatin capsules that contain 20 mg or 80 mg cabozantinib free base in the form of cabozantinib (S)-malate salt, silicified microcrystalline cellulose, croscarmellose sodium, sodium starch glycolate, fumed silica, and stearic acid. The U.S. FDA approved prescribing information indicates the COMETRIQ® capsules can be used to treat patients with progressive, metastatic medullary thyroid cancer. U.S. FDA approved prescribing information further indicates the COMETRIQ® capsules recommended dose is 140 mg once daily and the capsules should be administered at least 1 hour before or at least 2 hours after eating because administration with food, particularly a high fat meal, can increase the $C_{max}$ and AUC of cabozantinib by 41% and 57%, respectively, relative to fasted conditions in healthy subjects administered a single oral 140 mg COMETRIQ® dose.

SUMMARY OF THE INVENTION

The present invention relates to pharmaceutical compositions comprising cabozantinib and/or the pharmaceutically acceptable salts thereof, such as cabozantinib lauryl sulfate for oral administration and methods of using the oral compositions to treat cancer that obtain one or more the following needs and desires.

The present invention further relates oral pharmaceutical compositions comprising a therapeutic amount of cabozantinib, preferably cabozantinib lauryl sulfate salt, and one or more pharmaceutically acceptable excipients wherein the oral composition exhibits enhanced bioavailability or absorption under fasted conditions, compared to the commercially available CABOMETYX® tablets and/or COMETRIQ® capsules having the same dosage. In certain aspects, the present invention does not exhibit a food effect. In further aspects, the present invention exhibits a similar or equivalent $C_{max}$ and/or AUC, collectively a similar or equivalent bioavailability, when administered under fed and fasted conditions.

The present invention also relates oral pharmaceutical compositions comprising a therapeutic amount of cabozantinib, preferably cabozantinib lauryl sulfate salt, and one or more pharmaceutically acceptable excipients wherein the oral composition exhibits lower occurrence or severity of adverse events compared to the commercially available CABOMETYX® tablets and/or COMETRIQ® capsules. In some aspects, the present invention obtains the lower occurrence or severity of adverse events by administering an amount of cabozantinib base, preferably in the form of the cabozantinib lauryl sulfate salt, that provides a similar or equivalent $C_{max}$ and/or AUC, collectively a "similar bioavailability" or an "equivalent bioavailability", as the commercially available CABOMETYX® tablets and/or COMETRIQ® capsules. The lower occurrence or severity of adverse events may include gastrointestinal inflammation, diarrhea, loss of appetite, weight loss or a combination thereof.

The present invention still further relates oral pharmaceutical compositions comprising a therapeutic amount of cabozantinib, preferably cabozantinib lauryl sulfate salt, and one or more pharmaceutically acceptable excipients wherein the oral composition exhibits lower inter-subject variability for at least one pharmacokinetic parameter (i.e., $C_{max}$, $AUC_{0-t}$ and $AUC_{0-infinity}$) compared to the commercially available CABOMETYX® tablets and/or COMETRIQ® capsules when administered orally to human subjects.

In one aspect, the present invention provides a low dose oral pharmaceutical composition comprising cabozantinib, preferably cabozantinib lauryl sulfate salt, and one or more pharmaceutically acceptable excipients, wherein said composition, when administered orally, provides an equivalent efficacy at a lower dose of cabozantinib compared to the commercially available CABOMETYX® tablets and/or COMETRIQ® capsules, wherein said dose of cabozantinib free base, preferably provided in the form of cabozantinib lauryl sulfate, is at least about 10%, 15%, 20%, 25%, 30% 35%, 40%, 45%, 50%, 55%, 60%, 65%, 70%, 75%, 80%, 85% or 90% lower than the dose of cabozantinib free base provided in the form of cabozantinib (S)-malate salt.

The oral compositions of the present invention may be in the form of tablets, capsules, granules, beads, pellets or powders. In certain embodiments, the oral composition is a capsule wherein the contents of the capsule comprise a therapeutic amount of cabozantinib, preferably cabozantinib lauryl sulfate, and at least one pharmaceutically acceptable excipient. In one embodiment, the contents of the capsule comprise 2.5 mg to 250 mg of cabozantinib lauryl sulfate wherein the cabozantinib lauryl sulfate is amorphous, crystalline or a combination of amorphous and crystalline. In another embodiment, the contents of the capsule comprise one or more excipients with an HLB value of 10 or greater and which is a solid at room temperature but exhibits a melting point less than 100° C., 95° C., 90° C., 85° C., 80° C., 75° C., 70° C., 65° C., 60° C., 55° C., 50° C., 45° C., 40° C. or less.

The present invention further relates to methods of administration to a patient in need thereof, particularly a human patient, in need of treatment of a disorder treatable with a multiple receptor tyrosine kinase inhibitor. Examples of disorders that may be treated with oral compositions of the present invention comprising cabozantinib lauryl sulfate include, but are not limited to renal cell carcinoma, hepatocellular carcinoma and medullary thyroid cancer.

The present invention also relates to methods of preparing cabozantinib lauryl sulfate salts and polymorphic forms thereof. In certain embodiments the methods of preparing the cabozantinib lauryl sulfate salts produce stable crystalline forms with low impurity levels.

BRIEF DESCRIPTION OF DRAWINGS

FIG. 7 is a graph of the mean diarrhea data provided in Example 22.

FIG. 8 is a graph of the mean appetite data provided in Example 22.

DETAILED DESCRIPTION OF THE INVENTION

Figure 1:
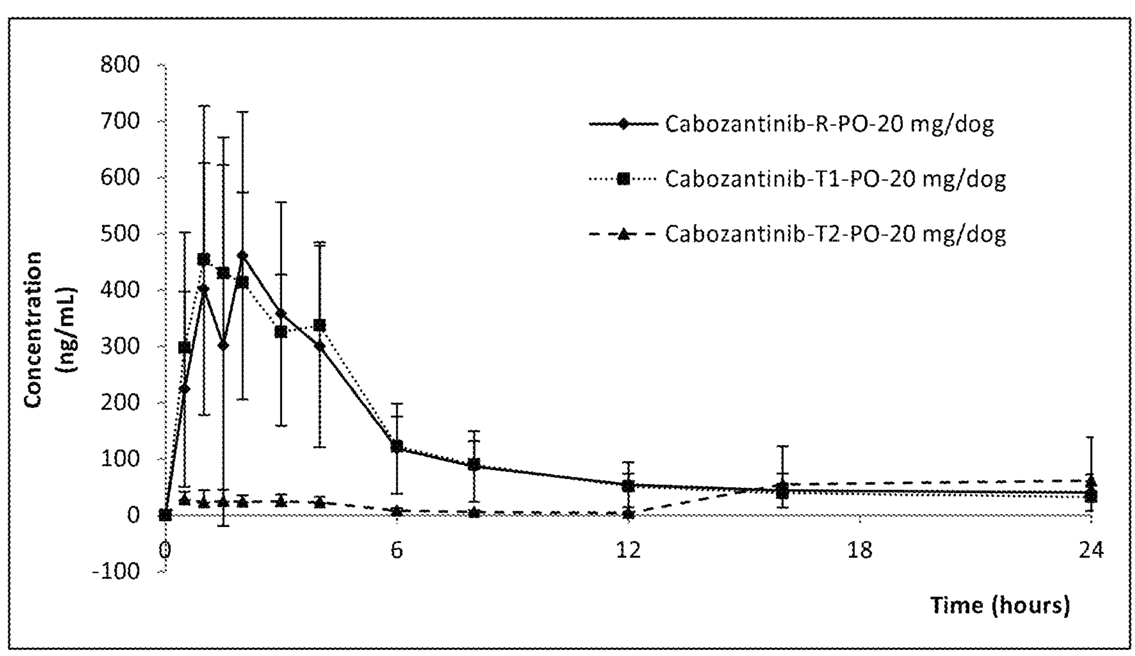
FIG. 1 is a graph of the mean in vivo plasma data provided in Example 17.

The U.S. FDA package insert for both CABOMETYX® tablets and COMETRIQ® capsules indicate the recommended dosages can be lowered for patients with moderate hepatic impairment and warn of very high incidents of gastrointestinal adverse effects, specifically about 63% for COMETRIQ® capsules and 62% for CABOMETYX® tablets of the patients experiencing diarrhea. It is believed that the diarrhea may be caused by a high amount of unabsorbed cabozantinib present in a patient's intestinal tract. This belief is based on data reported in the both CABOMETYX® tablets and COMETRIQ® capsules U.S. FDA approved package inserts which indicate that in a single dose study with healthy human subjects administered radiolabeled $^{14}C$-cabozantinib, approximately 81% of the total administered radioactivity was recovered within a 48-day collection period, with approximately 54% recovered in feces and 27% in urine. The U.S. FDA package inserts recommend dose reduction, dose interruption or discontinuation of treatment based on the severity of adverse effects.

The U. S. FDA package inserts for both CABOMETYX® tablets and COMETRIQ® capsules also report high inter-subject variability for $C_{max}$ and AUC values after administration [CV % $C_{max}$: 51% for the tablet formulation, 61% for the capsule formulation; CV % $AUC_{0-last}$, or $AUC_{0-infinity}$: 40-43% for the tablet formulation, 43% for the capsule formulation]. The reported geometric mean $C_{max}$ of the tablet formulation was approximately 49% higher than the value observed for the capsule formulation. The reported geometric mean $AUC_{0-last}$ and $AUC_{0-inafinity}$ values for the tablet formulation were also higher (15% and 19%, respectively) than those observed/or the capsule formulation.

In view of the foregoing, there is a need to develop pharmaceutical compositions of cabozantinib which can increase the bioavailability or absorption of cabozantinib and thereby allow for a reduction in the currently approved daily dose of cabozantinib to be administered to a human subject while maintaining therapeutic efficacy and reducing adverse events.

There also exists a need to reduce the food effect exhibited by the commercially available CABOMETYX® tablets and COMETRIQ® capsules thereby allowing administration of the cabozantinib to the patient at any time regardless of the fed state. The reduced food effect should maintain an equivalent bioavailability of cabozantinib in the patient if the patient is administered the cabozantinib in the fed or fasted state. This reduced food effect would improve patient compliance because the patient could take the medication at any convenient time and would prevent unwanted peaks or troughs in the cabozantinib plasma levels thereby maintaining optimal therapeutic concentrations of cabozantinib in the patients and reducing adverse events.

It is also desirable to have a composition for oral administration which provides cabozantinib to a patient population with lower variability in bioavailability, thus providing consistent PK parameters (e.g., a narrower observed range for $C_{max}$ and AUC values) across a patient population to whom the composition is administered.

U.S. Patent Application Publication No. 2022/0387418 and International Patent Publication No. WO 2022/115464 suggest pharmaceutical compositions that may be able to achieve some of the foregoing needs and desires, however, the compositions described is these publications are very complicated to prepare and none of these publications describe the compositions that employ cabozantinib lauryl sulfate salts.

Before the present invention is further described, it is to be understood that this invention is not limited to the particular embodiments described. It is also to be understood that the terminology used herein is for the purpose of describing particular embodiments only, and is not intended to be limiting.

It should be noted that as used herein, the singular forms "a," "an," and "the" include plural referents unless the context clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein, the term "normal storage conditions" refers to storage at room temperature, approximately 25° C. and approximately 60% relative humidity for at least three months, preferably at least six months, and most preferably at least one year. The dosage form in accordance with the present invention should be stored in pharmaceutically acceptable containers such as glass bottles, plastic bottles, metal foil pouch, or blister packaging with or without a desiccant.

As used herein, the term "accelerated storage conditions" refers to storage at approximately 40° C. and approximately 75% relative humidity for at least two weeks or longer, one month or longer, two months or longer, three months or longer, four months or longer, five months or longer, or six months or longer. The dosage form in accordance with the present invention should be stored in pharmaceutically acceptable containers such as glass bottles, plastic bottles, metal foil pouch, or blister packaging with or without a desiccant.

The term "HLB" refers to the "hydrophilic-lipophilic balance" of a surfactant or emulsifier and is a measure of the degree to which it is hydrophilic or lipophilic and is determined by calculating values for the different regions of the molecule, as described by Griffin W C, "Calculation of HLB Values of Non-Ionic Surfactants," Journal of the Society of Cosmetic Chemists, 5:259 (1954). HLB values range from 0 to 20, with an HLB value of 0 corresponding to a completely lipophilic molecule, and a value of 20 corresponding to a completely hydrophilic molecule. HLB values are generally known and reported in the literature such as the manufacturer's technical brochures.

The term "$C_{max}$" denotes the maximum plasma concentration obtained during the dosing interval.

The term "$T_{max}$" denotes the time to maximum plasma concentration ($C_{max}$).

The term "AUC" means an area under the drug concentration-time curve (AUC) calculated using linear trapezoidal summation for a specified interval of time, for example, $AUC_{0-12}$ refers to the area under the drug concentration-time curve from the time immediately preceding administration to 12 hours after administration, $AUC_{0-24}$ refers to the area under the drug concentration-time curve from the time immediately preceding administration to 24 hours after administration, $AUC_{0-\infty}$ or $AUC_{0-inf}$ refers to the area under the drug concentration-time curve from the time immediately preceding administration to infinity and $AUC_{0-t}$ refers to the area under the drug concentration-time curve from the time immediately preceding administration to the designated time point such as 2 hours, 8 hours, 18 hours etc. after administration. In some embodiments, the designated time point is the last time point of blood sampling.

The pharmacokinetic values described herein are generally determined according to methods known and understood by those in the art and are generally described in publications such as the United States Food and Drug Administration's (U.S. FDA) Guidance for Industry: Bioavailability and Bioequivalence Studies for Orally Administered Drug Products—General Considerations (March 2003); U.S. FDA's Guidance for Industry: Statistical Approaches to Establishing Bioequivalence (January 2001); and U.S. FDA's Guidance for Industry: Food-Effect Bioavailability and Fed Bioequivalence Studies (December 2002), which are incorporated herein by reference.

"Bioequivalence" and "equivalent" pharmacokinetic values such as $C_{max}$, $T_{max}$ or AUC refer to the absence of a significant difference between the bioavailability or designated pharmacokinetic value, e.g., the mean ratio of AUC (over 24 hours) and the mean ratio of $C_{max}$ is within 80% to 125% between two pharmaceutical drug products (e.g., a test composition and a reference composition) over the course of a period of time, at the same dose and/or under the same conditions. The determination of whether or not a test composition is bioequivalent to a reference composition may be determined by performing a study, referred to as a bioequivalence or comparative bioavailability study, in a group of subjects under controlled conditions.

The term "bioavailability" indicates the extent to which a drug or another substance is utilized by a target tissue after administration. For example, "bioavailability" may refer to the fraction of drug absorbed following administration to a subject or patient under fed or fasted conditions. The bioavailability may include one or more pharmacokinetic values such as $C_{max}$, AUC, and combinations thereof.

Reference throughout this specification will be made to the administration of a pharmaceutical composition under fed conditions or fasted condition. It is understood in the art that the pharmacokinetic performance of some drugs and compositions are affected by the presence or absence of food in the gastro-intestinal system. These references to fed and fasted conditions thus relate to the normally accepted administration circumstances that are referred to in the art as "fed" or "fasted."

As used herein, the term "fasted condition" generally means that the human or other mammal has not ingested 500 calories or more than 500 calories for at least one hour before taking a drug containing dosage form and for at least two hours after taking the drug containing dosage form.

As used herein, the term "fed state" refers to a human who has eaten a United States Food and Drug Administration (FDA) standard high fat breakfast (or other meal containing a comparable quantity of fat and calories) within said time period. The meal is high in both fat (approximately 50% of total calorie content of the meal) and calories (approximately 800-1000 calories).

The term "food effect" as used herein means food-drug interactions which either decrease or increase the extent of drug absorption. In other words, the bioavailability for a drug is altered when administered under fasted condition, in comparison to the drug when administered in the fed state. It may refer to a relative difference in one or more of $AUC_{0\text{-}infinity}$, $AUC_{0\text{-}t}$ and/or $C_{max}$ of a drug, when said drug or a formulation thereof is administered orally to a human, concomitantly with food or in a fed state as compared to the same values when the same formulation is administered in a fasted condition or without food.

In certain aspects, the food effect may be defined as the ratio of the $C_{max}$ and/or AUC values of the tested drug in fed versus fasted conditions. Measuring the $C_{max}$ and/or AUC values of the tested drug in fed and in fasted conditions is standard practice in the art.

In certain embodiments, the pharmaceutical compositions described herein reduce or eliminate the food effect. As used herein, "reducing the food effect" refers to narrowing the difference in bioavailability, e.g., $AUC_{0\text{-}infinity}$, $AUC_{0\text{-}t}$, $AUC_{0\text{-}12}$, $AUC_{0\text{-}24}$ and/or $C_{max}$ for a drug administered under fasted condition in comparison to the drug administered under fed condition. In certain aspects, the food effect is eliminated. Thus, upon oral administration of a pharmaceutical composition as described herein, to a mammal in need thereof, there is not a significant food effect. In other words, the difference between a pharmacokinetic parameter measured after oral administration to a mammal with and without food, respectively, is less than 40%, e.g., less than 35%, less than 30%, less than 25%, less than 20%, less than 15%, less than 10 or less than 5%. Preferably the composition or the pharmaceutical composition of the invention has at least 15% reduced food effect, preferably 20%, preferably 25%, preferably 30%, preferably 40%, reduced food effect.

The term "no food effect" as used herein means that formulation can be given with or without food. Further, there is no significant impact on $C_{max}$ value when given in fed or fasted condition. The mean fed/fasted ratio of $C_{max}$ value are preferably in the range of about 0.8 to about 1.25. Further, there is no significant impact on $AUC_{0\text{-}t}$ such as $AUC_{0\text{-}72}$ value when given in fed or fasted condition. The mean fed/fasted ratio of $AUC_{0\text{-}t}$ value are preferably in the range of about 0.8 to about 1.25.

The difference in AUC of the compositions of the present invention, when administered in the fed versus the fasted condition, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

The difference in $C_{max}$ of the compositions of the present invention, when administered in fed versus the fasted condition, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

In some embodiments, administration of the pharmaceutical composition to fed and/or fasted subjects produce a coefficient of variation in $AUC_{0\text{-}t}$, $T_{max}$, $C_{max}$ and/or $AUC_{0\text{-}infinity}$ of less than about 60% (e.g., less than 55%, 50%, 45%, 40%, 35%, 30%, 25%, 20%, and 15%). In particular embodiments, the coefficient of variation in $AUC_{0\text{-}t}$, $T_{max}$, $C_{max}$ and/or $AUC_{0\text{-}infinity}$ is of from about 20% to about 60% (e.g., from 20% to 30%, from 20% to 35%, from 20% to 40%, from 20% to 45%, from 20% to 50%, from 20% to 55%, from 30% to 35%, from 30% to 40%, from 30% to 45%, from 30% to 50%, from 30% to 55%, from 30% to 60%, from 35% to 40%, from 35% to 45%, from 35% to 50%, from 35% to 55%, from 35% to 60%, from 40% to 45%, from 40% to 50%, from 40% to 55%, from 40% to 60%, from 45% to 50%, from 45% to 55%, from 45% to 60%, from 50% to 55%, from 50% to 60%, and from 55% to 60%).

Oral administration of the pharmaceutical compositions of the present invention enhances the bioavailability of the cabozantinib making it possible to use reduced doses of cabozantinib (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124 or 125 mg per day) while achieving same or substantially similar therapeutic efficacy as compared to the commercially approved doses (e.g., 20, 40, and 60 mg CABOMETYX® tablet and/or 140 mg COMETRIQ® capsule per day).

On the other hand, the pharmaceutical compositions of the present invention allow administration of a lower dose (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124 or 125 mg per day) while retaining the therapeutic efficacy of cabozantinib, resulting in reduced undesirable side effects such as hemorrhage, gastro-intestinal perforations and fistulas, thrombotic events, hypertension and hypertensive crisis, diarrhea, vomiting, nausea, palmar-plantar erythrodysesthesia, proteinuria, decreased appetite, weight decreased associated with the use of conventional doses.

In certain embodiments, the pharmaceutical compositions of the present invention allow administration of a reduced dose of cabozantinib, preferably in the form of cabozantinib lauryl sulfate salt, while achieving same or substantially similar therapeutic efficacy as compared to the commercially approved CABOMETYX® tablet and/or COMETRIQ® capsule as the follows:

| | Reduced dose of cabozantinib | | |
|---|---|---|---|
| Per dosage form | Preferred | More Preferred | Most Preferred |
| 20 mg CABOMETYX ® | 5 to 17 mg | 8 to 15 mg | 10 to 14 mg |
| 40 mg CABOMETYX ® | 10 to 35 mg | 16 to 30 mg | 20 to 28 mg |
| 60 mg CABOMETYX ® | 20 to 50 mg | 25 to 45 mg | 30 to 40 mg |
| 20 mg COMETRIQ ® | 5 to 17 mg | 8 to 15 mg | 10 to 14 mg |
| 80 mg COMETRIQ ® | 24 to 65 mg | 30 to 60 mg | 40 to 55 mg |

In one aspect of this embodiment, the present invention includes a method for administering a reduced dose of cabozantinib to a patient comprising the steps of (i) determining the amount of cabozantinib free base that will or is providing a therapeutic dose of cabozantinib to a subject in need of cabozantinib via the oral administration of a cabozantinib (S)-malate salt in the form of a solid immediate release tablet, i.e., the CABOMETYX® tablet and/or an immediate release capsule, i.e. the COMETRIQ® capsule and (ii) orally administering to the subject a dosage form in accordance with the present invention with a reduced dose of cabozantinib or pharmaceutically acceptable salt thereof as shown in the above reduced dose table.

For example, if the subject is obtaining therapeutic effects via administration once daily of the 60 mg CABOMETYX® tablet, then the subject will be adminstered a dosage form in accordance with the present invention comprising 20 to 50 mg, 25 to 45 mg or 30 to 40 mg of cabozantinib or a pharmaceutically acceptable salt thereof. Similarly, if the subject is obtaining therapeutic effects via administration once daily of the 80 mg COMETRIQ® capsule, then the subject will be adminstered a dosage form in accordance with the present invention comprising 24 to 65 mg, 30 to 60 mg or 40 to 55 mg of cabozantininb or a pharmaceutically acceptable salt thereof.

In another one aspect of this embodiment, the present invention includes a method for administering a reduced dose of cabozantinib to a patient comprising the steps of (i) determining the amount of cabozantinib free base that will or is providing a therapeutic dose of cabozantinib to a subject in need of cabozantinib via the oral administration of a cabozantinib (S)-malate salt in the form of a solid immediate release tablet, i.e., the CABOMETYX® tablet and/or an immediate release capsule, i.e. the COMETRIQ® capsule and (ii) orally administering to the subject a dosage form in accordance with the present invention with a reduced dose of cabozantinib or pharmaceutically acceptable salt thereof wherein the reduced dose is 90%, 85%, 80%, 75%, 70%, 65%, 60%, 55% or 50% of amount of cabozantinib determine in step (i).

Oral administration of the pharmaceutical compositions of the present invention will reduce one or more undesirable side effects, especially decreased appetite, weight decreased and gastrointestinal adverse reaction such as diarrhea, nausea, vomiting, stomatitis, constipation, abdominal pain, dyspepsia or any combination of the foregoing compared to the commercially available CABOMETYX® tablets and/or COMETRIQ® capsules.

In certain embodiments, the occurrence rate of one or more adverse reactions may be reduced by administering compositions in accordance with the present invention to a human subject compared to the commercially available CABOMETYX® tablets and/or COMETRIQ® capsules as follows:

| | Reduction in Occurring Percentage (%) of Patients | | |
|---|---|---|---|
| AEs | Preferred | More Preferred | Most Preferred |
| Diarrhea | 5% to 60% | 10% to 50% | 15% to 45% |
| Nausea | 5% to 40% | 6% to 30% | 7.5% to 25% |
| Vomiting | 5% to 30% | 5% to 20% | 5% to 15% |
| Stomatitis | At least 10% | At least 15% | At least 20% |
| Constipation | At least 10% | At least 15% | At least 20% |
| Abdominal pain | At least 10% | At least 15% | At least 20% |
| Dyspepsia | At least 5% | At least 7.5% | At least 10% |
| Decreased appetite | 5% to 60% | 10% to 50% | 15% to 45% |
| Weght decreased | 5% to 60% | 10% to 50% | 15% to 45% |
| Fatigue | 5% to 60% | 10% to 50% | 15% to 45% |
| Hypertension | 5% to 60% | 10% to 50% | 15% to 45% |

In certain embodiments, the occurrence rate of one or more severe adverse reactions (Grade 2-4 AEs) may be reduced by administering compositions in accordance with the present invention to a human subject compared to the commercially available CABOMETYX® tablets and/or COMETRIQ® capsules as follows:

| | Reduction in Occurring Percentage (%) of Patients | | |
|---|---|---|---|
| Grade 2-4 AEs | Preferred | More Preferred | Most Preferred |
| Diarrhea | At least 5% | At least 7.5% | At least 10% |
| Decreased appetite | At least 5% | At least 7.5% | At least 10% |
| Weght decreased | At least 5% | At least 7.5% | At least 10% |
| Nausea | At least 5% | At least 7.5% | At least 10% |
| Vomiting | At least 5% | At least 7.5% | At least 10% |
| Fatigue | At least 5% | At least 7.5% | At least 10% |
| Hypertension | At least 5% | At least 7.5% | At least 10% |

In certain embodiments, the occurrence rate of dose interruption and/or dose reduction due to adverse reactions may be reduced by administering compositions in accordance with the present invention to a human subject compared to the commercially available CABOMETYX® tablets and/or COMETRIQ® capsules as follows:

| | Reduction in Occurring Percentage (%) of Patients | | |
|---|---|---|---|
| AEs | Preferred | More Preferred | Most Preferred |
| Diarrhea | At least 5% | At least 7.5% | At least 10% |
| Decreased appetite | At least 5% | At least 7.5% | At least 10% |
| Weght decreased | At least 5% | At least 7.5% | At least 10% |
| Nausea | At least 5% | At least 7.5% | At least 10% |
| Vomiting | At least 5% | At least 7.5% | At least 10% |
| Fatigue | At least 5% | At least 7.5% | At least 10% |
| Hypertension | At least 5% | At least 7.5% | At least 10% |

For example, it is reported that 63% of patients administered the commercially available CABOMETYX© tablets experienced diarrhea. It is expected that 56% or less of the human subjects administered compositions according to the present invention will experience diarrhea, which is at least a 10% reduction in the occurring percentage.

In certain embodiments, the reduction in adverse events will be determined by administering a composition of the present invention and the commercially available CABOMETYX® tablets or COMETRIQ® capsules wherein the composition of the present invention and the commercially available CABOMETYX® tablets or COMETRIQ® capsules contain the same or equal amounts of cabozantinib free base. Alternatively, the reduction in adverse events will be determined by administering a composition of the present invention and the commercially available CABOMETYX® tablets or COMETRIQ® capsules wherein the composition of the present invention contains a reduced or lower amount of cabozantinib free base as described herein compared to the amount of cabozantinib administered with the commercially available CABOMETYX® tablets or COMETRIQ® capsules. In this alternative embodiment, the reduced or lower amount of cabozantinib free base administered with the compositions of the present invention should produce the same or equivalent $C_{max}$ and/or AUC values obtained by the administration of the commercially available CABOMETYX® tablets or COMETRIQ® capsules.

In certain embodiments, the occurrence rate of one or more adverse reactions may be reduced by administering compositions in accordance with the present invention to a human subject as follows:

| | Occurrence rate (%) of Patients | | |
|---|---|---|---|
| AEs | Preferred | More Preferred | Most Preferred |
| Diarrhea | Less than 60% | Less than 50% | 10% to 45% |
| Decreased appetite | Less than 40% | Less than 30% | Less than 25% |
| Weght decreased | Less than 40% | Less than 30% | Less than 25% |
| Nausea | Less than 50% | Less than 40% | Less than 25% |
| Vomiting | Less than 40% | Less than 30% | Less than 25% |
| Fatigue | Less than 50% | Less than 40% | Less than 30% |
| Hypertension | Less than 35% | Less than 25% | 10% to 20% |

In certain embodiments, the occurrence rate of one or more severe adverse reactions (Grade 2-4 AEs) may be reduced by administering compositions in accordance with the present invention to a human subject as follows:

| | Occurrence rate (%) of Patients | | |
|---|---|---|---|
| Grade 2-4 AEs | Preferred | More Preferred | Most Preferred |
| Diarrhea | Less than 30% | Less than 20% | Less than 10% |
| Decreased appetite | Less than 8% | Less than 5% | Less than 3% |
| Weght decreased | Less than 8% | Less than 5% | Less than 3% |
| Nausea | Less than 15% | Less than 10% | Less than 5% |
| Vomiting | Less than 8% | Less than 5% | Less than 3% |
| Fatigue | Less than 30% | Less than 20% | Less than 10% |
| Hypertension | Less than 40% | Less than 30% | Less than 20% |

In certain embodiments, the occurrence rate of dose interruption and/or dose reduction due to adverse reactions may be reduced by administering compositions in accordance with the present invention as follows:

| | Occurrence rate (%) of Patients | | |
|---|---|---|---|
| AEs | Preferred | More Preferred | Most Preferred |
| Diarrhea | Less than 60% | Less than 50% | 10% to 45% |
| Decreased appetite | Less than 40% | Less than 30% | Less than 25% |
| Weght decreased | Less than 40% | Less than 30% | Less than 25% |
| Nausea | Less than 50% | Less than 40% | Less than 25% |
| Vomiting | Less than 40% | Less than 30% | Less than 25% |
| Fatigue | Less than 50% | Less than 40% | Less than 30% |
| Hypertension | Less than 35% | Less than 25% | 10% to 20% |

In certain embodiments, following administration of the pharmaceutical composition of the present invention to subjects (e.g., fed or fasted condition), the mean bioavailability is greater than about 10% (e.g., greater than 15%, 20%, 25%, 30%, 35%, 40%, 4%5% 50%, 55%, 60%, 65%, 70%, 75%, 80%, 85%, 90%, 95%, or even 99%) or between about 10% to about 90% (e.g., from 10% to 20%, from 10% to 30%, from 10% to 40%, from 10% to 50%, from 10% to 60%, from 10% to 70%, from 10% to 80%, from 10% to 90%, from 15% to 20%, from 15% to 30%, from 15% to 40%, from 15% to 50%, from 15% to 60%, from 15% to 70%, from 15% to 80%, from 15% to 90%, from 20% to 30%, from 20% to 40%, from 20% to 50%, from 20% to 60%, from 20% to 70%, from 20% to 80%, from 20% to 90%, from 30% to 40%, from 30% to 50%, from 30% to 60%, from 30% to 70%, from 30% to 80%, from 30% to 90%, from 40% to 50%, from 40% to 60%, from 40% to 70%, from 40% to 80%, from 40% to 90%, from 50% to 60%, from 50% to 70%, from 50% to 80%, from 50% to 90%, from 60% to 70%, from 60% to 80%, from 60% to 90%, from 70% to 80%, from 70% to 90%, and from 80% to 90%) as compared to the commercially available CABOMETYX® tablets and/or COMETRIQ® capsules.

As used herein, and unless otherwise defined, the term "subject" refers to a mammal such as a human, monkey, cow, horse, sheep, pig, chicken, turkey, quail, cat, dog, mouse, rat, rabbit, or guinea pig, preferably humans and includes healthy mammals and mammals affected with a disease that may be treated with cabozantinib. A subject that is affected with a disease that may be treated with the cabozantinib is sometimes referred to as "patient".

As used herein, and unless otherwise defined, the phrase "therapeutically effective amount" when used in connection with a pharmaceutical composition or dosage form comprising the cabozantinib lauryl sulfate salt means an amount of cabozantinib lauryl sulfate salt thereof effective for treating a disease or disorder disclosed herein, such as cancer including but not limited to renal cell carcinoma, hepatocellular carcinoma and medullary thyroid cancer.

As used herein, and unless otherwise defined, the phrases "intimately mixed," "intimate mixture" and the like refer to a combination of the cabozantinib lauryl sulfate salt and at least one pharmaceutically acceptable excipient, preferably a carrier with an HLB value of about 10 or greater, about 11 or greater, about 12 or greater, about 13 or greater, or about 14 or greater such as a wetting agent, emulsifying agent, solubilizing agent, surfactant or combinations thereof, wherein the cabozantinib lauryl sulfate salt and at least one pharmaceutically acceptable excipient are in intimate contact or close association with each other. The intimate mixture may be prepared by any procedure that enables through blending of the cabozantinib lauryl sulfate salt and the at least one pharmaceutically acceptable excipient, preferably a carrier with an HLB value of about 10 or greater. An example of a suitable process for achieving the intimate mixture includes dissolving, suspending or dispersing the cabozantinib sulfate salt in a solution or suspension containing the at least one pharmaceutically acceptable excipient, preferably a carrier with an HLB value of about 10 or greater and optionally at least one additional pharmaceutically acceptable excipient such as a pharmaceutically acceptable solvent. The pharmaceutically acceptable solvent may or may not be removed. Another example of a suitable process for achieving the intimate mixture includes employing a liquid excipient wherein the liquid comprises at least one pharmaceutically acceptable excipient with an HLB value of about 10 or greater or melting one or more solid excipients wherein the melt comprises at least one pharmaceutically acceptable excipient with an HLB value of about 10 or greater, to create a melted or liquid excipient composition comprising at least one excipient with an HLB value of about 10 or greater, and dissolving, suspending or dispersing the cabozantinib, preferably cabozantinib lauryl sulfate salt, in the melted or liquid excipient composition. The liquid excipient composition comprising at least one excipient with an HLB value of about 10 or greater, may also comprise one or more pharmaceutically acceptable excipients and described in greater detail below. Other processes that may be used to achieve the intimate mixture of the cabozantinib, preferably cabozantinib lauryl sulfate salt, and at least one pharmaceutically acceptable excipient preferably with an HLB value of about 10 or greater, include co-blending, co-screening, co-compacting, co-compressing or a combination thereof. Once the intimate mixture of the cabozantinib, preferably cabozantinib lauryl sulfate salt, and at least one pharmaceutically acceptable excipient, preferably with an HLB value of about 10 or greater, is prepared, the intimately mixed composition may be combined with at least one additional pharmaceutical excipient or carrier. The intimate mixture may preferably comprise the cabozantinib, preferably the cabozantinib lauryl sulfate salt, and one, two or three excipients prior to being combined with any additional excipients.

The cabozantinib employed in the present invention may be cabozantinib free base, one or more pharmaceutically acceptable salts of cabozantinib or a combination thereof. The pharmaceutically acceptable salt may include acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like. Preferably, the present invention employs cabozantinib lauryl sulfate.

The cabozantinib lauryl sulfate salt may be formed by reacting the cabozantinib molecule with an alkaline or alkaline earth metal lauryl sulfate. Examples of preferred alkaline or alkaline earth metal lauryl sulfate include but are not limited to sodium or potassium lauryl sulfate. One process for preparing the cabozantinib lauryl sulfate can be found in International Patent Application Publication No. WO 2019/241504, example 41 which is incorporated herein by reference.

The present invention also encompasses compositions and dosage forms comprising the cabozantinib, preferably cabozantinib lauryl sulfate salt, and at least one pharmaceutically acceptable excipient for oral administration to a subject. The compositions and dosage forms may be a solid, semi-solid or liquid, wherein the cabozantinib, preferably cabozantinib lauryl sulfate salt, is combined with pharmaceutically acceptable excipients such as fillers, diluents, binders, stabilizing agents, lubricants, disintegrants, wetting/solubilizing/emulsifying agents or mixtures thereof. The pharmaceutically acceptable excipients are well known in the art and are described in Remington, The Science and Practice of Pharmacy, $21^{st}$ ed. (2006), pp. 1058-1092, and Handbook of Pharmaceutical Excipients, $6^{th}$ ed. (2009). Representative examples of the various pharmaceutically acceptable excipients employed in the embodiments of the present invention are provided below.

The solid and semi-solid compositions and dosage forms include powders, granules, pellets, beads, mini-tablets, tablets, or capsules and may be made by methods known in the art such as direct compression, wet or dry granulation, and extrusion spheronization.

The liquid compositions and dosage forms include solutions, suspensions, or dispersions and these may also be made by methods known in the art.

In one embodiment of the present invention, the composition or dosage form for oral administration is a tablet or a hard capsule such as a gelatin capsule or a HPMC capsule or a soft capsule comprising cabozantinib, preferably cabozantinib lauryl sulfate salt, and one or more pharmaceutically acceptable carriers, preferably in an intimate mixture. In certain aspects of this embodiment, the pharmaceutically acceptable carrier is a solid at ambient conditions, i.e., 25° C. and standard atmospheric pressure but has a melting point above 25° C. but less than 100° C., 95° C., 90° C., 85° C., 80° C., 75° C., 70° C., 65° C., 60° C., 55° C., 50° C., 45° C., 40° C., 35° C. or any range of the foregoing.

If the carrier is a solid or semi-solid at ambient temperature, the carrier may be mixed or granulated with the cabozantinib, preferably cabozantinib lauryl sulfate salt, and optionally one or more additional pharmaceutically acceptable excipients prior to forming into a tablet or filling or forming into a hard or soft capsule. Alternatively, if the carrier is a solid or semi-solid at ambient temperature the carrier may be heated to melt the carrier and the melted carrier, cabozantinib, preferably cabozantinib lauryl sulfate salt, and optionally one or more additional pharmaceutically acceptable excipients are mixed prior to forming into a tablet or filling or forming into a hard or soft capsule.

In certain embodiments, the cabozantinib, preferably the cabozantinib lauryl sulfate salt, is dispersed or suspended in the liquid carrier or dispersed or suspended in the melted solid or semi-solid carrier.

Examples of liquid carriers that may be used in preparing the oral dosage forms of the present invention include but are not limited to fatty acids, medium chain triglycerides, fatty acid esters, fatty acid alcohols, vegetable oils such as corn oil, soybean oil, olive oil, sun flower oil, peanut oil or mixtures thereof. In certain embodiments the liquid carrier should comprise about 10%, 15%, 20%, 25%, 30%, 40%, 45%, 50%, 55%, 60%, 65%, 70%, 75%, 80%, 85%, 90% and 95% (w/w) of the composition or any range encompassed by the foregoing values, preferably about 15% (w/w)

to about 90% (w/w) and most preferably about 20% (w/w) to about 85% (w/w) of the composition filled into the capsule.

Examples of solid carriers with a melting point between 25° C. and 100° C., preferably with a melting point between 30° C. and 90° C., preferably with a melting point between 35° C. and 80° C., and most preferably with a melting point between 40° C. and 75° C. include aliphatic alcohols, polyethylene glycol, such as polyethylene glycol 1000 with a melting point of 37-40° C., polyethylene glycol 1500 with a melting point of 44-48° C., hard fat (aka hydrogenated vegetable glycerides), hydrogenate vegetable oil, vitamin E polyethylene glycol succinate (aka TPGS), poloxamers (nonionic polyoxyethylene-polyoxypropylene copolymers such as poloxamer 188, poloxamer 237, poloxamer 338 and poloxamer 407), polyoxylglycerides, polyoxyethylene stearates, polyoxyl stearates, and waxes, such as carnauba wax, cetyl ester wax, microcrystalline wax, white wax, and yellow wax and combinations of the foregoing solid carriers. In certain embodiments, the solid carrier should comprise about 2.5%, 5%, 7.5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 92.5%, 95% (w/w) or any range encompassed by the foregoing values, preferably about 5% (w/w) to about 90% (w/w) and most preferably about 7.5% (w/w) to about 85% (w/w) of the composition filled into the capsule or formed into a tablet.

Additional examples of the solid, semi-sold and liquid carriers that may be used in preparing the solid, semi-solid or liquid dosage forms of the present invention including but not limited to hard HPMC capsules, hard gelatin capsules, soft gelatin capsules and tablets of the present invention include wetting agents, emulsifying agents, solubilizing agents, surfactants or combinations thereof that exhibit an HLB value of about 10 or greater, an HLB value of about 11 or greater, an HLB value of about 12 or greater, an HLB value of about 13 or greater or an HLB value of about 14 or greater are described in detail below.

In another embodiment of the present invention, the compositions or dosage forms may comprise the cabozantinib, preferably cabozantinib lauryl sulfate salt, and one or more wetting agent, emulsifying agent, solubilizing agent, surfactant or combinations thereof that exhibits an HLB value of about 10 or greater, an HLB value of about 11 or greater, an HLB value of about 12 or greater, an HLB value of about 13 or greater or an HLB value of about 14 or greater and optionally at least one additional pharmaceutically acceptable excipient. The cabozantinib, preferably cabozantinib lauryl sulfate salt, may be present in the composition in an amount of about 1 wt % to about 80 wt % based on the total weight of the composition or dosage form, preferably about 2 wt % to about 70 wt %, more preferably about 2.5 wt % to about 60 wt % and most preferably about 3 wt % to about 50 wt %. In certain embodiments, the cabozantinib, preferably cabozantinib lauryl sulfate salt, may be present in the composition in an amount of about 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, or any range encompassed by the foregoing values. The one or more wetting agent, emulsifying agent, solubilizing agent, surfactant or combinations thereof that exhibits an HLB value of about 10 or greater, about 11 or greater, about 12 or greater, about 13 or greater or about 14 or greater should be present in the composition or dosage form in an amount of 1 wt % or greater based on the total weight of the composition or dosage form, preferably in an amount of about 2 wt % or greater and most preferably in an amount of about 5 wt % or greater based on the total weight of the composition or dosage form. In certain embodiments, the one or more wetting agent, emulsifying agent, solubilizing agent, surfactant or combinations thereof that exhibits an HLB value of about 10 or greater, about 11 or greater, about 12 or greater, about 13 or greater or about 14 or greater should be present in the composition or dosage form in an amount of about 10 wt % to about 90 wt %, preferably about 20 wt % to about 80 wt % and most preferably about 30 wt % to about 70 wt %. In certain embodiments, the one or more wetting agent, emulsifying agent, solubilizing agent, surfactant or combinations thereof that exhibits an HLB value of about 10 or greater, about 11 or greater, about 12 or greater, about 13 or greater or about 14 or greater should be present in the composition or dosage form in an amount of about 40 wt % to about 90 wt %, preferably about 45 wt % to about 85 wt % and most preferably about 50 wt % to about 80 wt %. In certain embodiments, the one or more wetting agent, emulsifying agent, solubilizing agent, surfactant or combinations thereof that exhibits an HLB value of about 10 or greater may be present in the composition in an amount of about 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt % 49 wt % 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, 90 wt % or any range encompassed by the foregoing values.

The one or more wetting agent, emulsifying agent, solubilizing agent, surfactant or combinations thereof that exhibits with an HLB value of about 10 or greater may be a non-ionic surfactant, an ionic surfactant or a combination thereof and is preferably a non-ionic surfactant. Examples of non-ionic surfactants that may be used include polyethoxylated castor oil, a polyoxyethylene alkyl ester, a polyglycolyzed glyceride, a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, a polyoxypropylene fatty acid ester, polyoxylglycerides, polyoxyethylene stearates, polyoxyl stearates, vitamin E polyethylene glycol succinate (aka TPGS) or a mixture of the foregoing. A further listing of possible non-ionic surfactants can be found on pages 1243-1249 of Martindale, The Extra Pharmacopoeia, $29^{th}$ ed. which is incorporated herein by reference.

The one or more wetting agent, emulsifying agent, solubilizing agent, surfactant or combinations thereof that exhibits an HLB value of about 10 or greater may be a non-ionic surfactant such as fatty alcohol acid or amide ethoxylates, monoglyceride ethoxylates, sorbitan ester ethoxylates alkyl polyglycosides, and mixtures thereof. Examples of these non-ionic surfactants include but are not limited to polyoxyethylene derivatives of polyol esters, such as Polysorbate 20 (commercially available under the tradename TWEEN® 20), Polysorbate 40 (commercially available under the tradename TWEEN® 40) Polysorbate 60 (commercially available under the tradename TWEEN® 60), and Polysorbate 80 (commercially available under the tradename TWEEN® 80).

The one or more wetting agent, emulsifying agent, solubilizing agent, surfactant or combinations thereof that exhibit an HLB value of about 10 or greater may be a polyoxyethylene castor oil such as polyoxyl castor oil or polyoxyl hydrogenated castor oil or mixtures thereof. Examples of these surfactants include but are not limited to polyoxyl 35 castor oil (commercially available under the tradename CREMAPHOR EL or KOLLIPHOR EL), polyoxyl 40 hydrogenated castor oil (commercially available under the tradename CREMOPHOR RH 40) and polyoxyl 60 hydrogenated castor oil.

The one or more wetting agent, emulsifying agent, solubilizing agent, surfactant or combinations thereof that exhibit an HLB value of about 10 or greater may be a polyoxyethylene stearate, also known as polyethoxylated derivatives of stearic acid, ethoxylated fatty acid esters; macrogol stearates; PEG fatty acid esters; PEG stearates; polyethylene glycol stearates; and polyoxyethylene glycol stearates. Polyoxyethylene stearates are nonionic surfactants produced by polyethoxylation of stearic acid. Numerous commercial grades are available which vary by the approximate polymer length or molecular weight of oxyethylene units. The polyoxyethylene stearates may be mono-stearates, di-stearates or a combination of mono-stearates and di-stearates. Preferred polyoxyethylene stearates comprise monostearates such as PEG-150 stearate, PEG-100 stearate, PEG-50 stearate, PEG-40 stearate, PEG-32 stearate, PEG-20 stearate and PEG-12 stearate.

The one or more wetting agent, emulsifying agent, solubilizing agent, surfactant or combinations thereof that exhibits an HLB value of about 10 or greater may be a polyoxyethylene alkyl ether such as a polyoxyl cetostearyl ether, polyoxyl cetyl ether, polyoxyl lauryl ether, polyoxyl oleyl ether, polyoxyl stearyl ether or mixtures thereof.

The one or more wetting agent, emulsifying agent, solubilizing agent, surfactant or combinations thereof that exhibit an HLB value of about 10 or greater may be a tyloxapol, a poloxamer, i.e., a nonionic polyoxyethylene-polyoxypropylene copolymers such as poloxamer 188, poloxamer 237, poloxamer 338, poloxamer 407 or a combination thereof.

The one or more wetting agent, emulsifying agent, solubilizing agent, surfactant or combinations thereof that exhibit an HLB value of about 10 or greater may be a fatty acid ester or fatty acid alcohol of a polyglyceride such as a caprylic/capric triglyceride (commercially available under the tradename MYIGLYOL).

The one or more wetting agent, emulsifying agent, solubilizing agent, surfactant or combinations thereof that exhibit an HLB value of about 10 or greater may be a vitamin E derivative such as Vitamin E polyethylene glycol succinate, aka TPGS.

In certain embodiments of the present invention, the composition comprises the cabozantinib, preferably cabozantinib lauryl sulfate salt, and one or more wetting agent, emulsifying agent, solubilizing agent, surfactant or combinations thereof that exhibit an HLB value of about 10 or greater, preferably in an intimate mixture, and may also further comprise at least one additional secondary carrier with a low or no HLB value. The secondary carrier may be one or more wetting agent, emulsifying agent, solubilizing agent, surfactant or combinations thereof that exhibits an HLB value of about less than 10, more preferably an HLB value of about 9 or less, about 8 or less, and most preferably an HLB value of about 7 or less. Examples of the at least one additional secondary carriers with a low HLB value include non-ionic surfactants which include but are not limited to polyethoxylated castor oil, a polyoxyethylene alkyl ester, a polyglycolyzed glyceride, a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, a polyoxypropylene fatty acid ester, or a mixture of the foregoing. A further listing of possible non-ionic surfactants with low HLB values can be found on pages 1243-1249 of Martindale, The Extra Pharmacopoeia, $29^{th}$ ed. which is incorporated herein by reference.

In certain embodiments, the secondary carrier with an HLB value of about less than 10 is a medium chain (i.e., about 4 to about 20 carbon atoms, preferably about 6 to about 18 carbon atoms and most preferably about 6 to and 14 carbon atoms) monoglyceride or diglyceride such as a glyceryl caprylate/caprate (commercially available under the tradename CAPMUL MCM), a glyceryl caprylate (commercially available under the tradename CAPMUL MCM C8), glyceryl caprate (commercially available under the tradename CAPMUL MCM C10), glyceryl monocaprylocaprate (commercially available under the tradename CAPMUL 471) or mixtures thereof.

In certain embodiments, the secondary carrier with an HLB value of about less than 10 is a polyoxylglyceride such as caprylocaproyl polyoxylglycerides, lauroyl polyoxylglycerides, linoleoyl polyoxylglycerides, oleoyl polyoxylglycerides, stearoyl polyoxylglycerides, and mixtures of the foregoing.

In certain embodiments, the secondary carrier with an HLB value of about less than 10 is a sorbitan ester or sorbitan fatty acid ester such as sorbitan monolaurate, sorbitan monooleate, sorbitan monopalmitate, sorbitan monostearate, sorbitan sesquioleate, sorbitan trioleate, tyloxapol, and mixtures of the foregoing.

In certain embodiments, the secondary carrier with an HLB value of about less than 10 is a phospholipid or lecithin.

In certain embodiments, the secondary carrier is an oil, a medium chain triglyceride, hydrogenated vegetable oil, suppository bases or combinations thereof.

In certain embodiments, the secondary carrier with an HLB of about less than 10 is liquid at ambient temperature or exhibits a melting point of about 75° C. or less, about 70° C. or less, about 65° C. or less, about 60° C. or less, about 55° C. or less, about 50° C. or less, about 45° C. or less or about 40° C. or less.

In the embodiments employing the secondary carrier with an HLB value of about less than 10, the amount of the secondary carrier with an HLB value about less than 10 may be about 1 wt % to about 90 wt % based on the total weight of the composition, preferably about 5 wt % to about 85 wt % and most preferably about 10 wt % to about 80 wt %. In certain embodiments employing the secondary carrier with an HLB value of about less than 10, the amount of the secondary carrier with an HLB value about less than 10 may be about 1 wt % to about 50 wt % based on the total weight of the composition, preferably about 5 wt % to about 45 wt % and most preferably about 10 wt % to about 40 wt %. The forgoing weight percentages may be based on a single secondary carrier or a combination of secondary carriers. In certain embodiments, the one or more wetting agent, emulsifying agent, solubilizing agent, surfactant or combinations thereof that exhibits an HLB value of about less than 10 may be present in the composition in an amount of about 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt % 49 wt % 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt % or any range encompassed by the foregoing values.

The compositions and dosage forms of the present invention may also optionally comprise additional pharmaceutically acceptable excipients such as stabilizers, fillers, viscosity enhancing agents, binders, disintegrants, lubricants, glidants, flavoring agents, and combinations thereof.

In certain embodiments the dosage form of the present invention is a solid or semi-solid oral dosage form, preferably a capsule or tablet that comprises:

(i) about 1 wt % to about 60 wt % based on the total weight of the solid composition or dosage form, preferably about 2 wt % to about 55 wt % and most preferably about 5 wt % to about 50 wt % of cabozantinib, preferably cabozantinib lauryl sulfate salt;

(ii) about 1 wt % to about 95 wt %, preferably about 5 wt % to about 90 wt % and most preferably about 10 wt % to about 85 wt % of one or more wetting agents, solubilizing agents, emulsifying agents, surfactants or combinations thereof that exhibits an HLB value of about 10 or greater, an HLB value of about 11 or greater, an HLB value of about 12 or greater an HLB value of about 13 or greater or an HLB value of about 14 or greater; and (iii) optionally at least one additional pharmaceutically acceptable excipient selected from the group consisting of stabilizers, fillers, viscosity enhancing agents, binders, disintegrants, lubricants, glidants, flavoring agents, and combinations thereof.

In certain embodiments, the composition of the present invention is capsule, preferably a hard capsule wherein the contents of the capsule comprise:

(i) about 1 wt % to about 60 wt % based on the total weight of the solid composition or dosage form, preferably about 2 wt % to about 55 wt % and most preferably about 5 wt % to about 50 wt % of cabozantinib, preferably cabozantinib lauryl sulfate salt;

(ii) about 10 wt % to about 95 wt %, preferably about 15 wt % to about 90 wt % and most preferably about 20 wt % to about 85 wt % of one or more wetting agents, solubilizing agents, emulsifying agents, surfactants or combinations thereof that exhibits an HLB value of about 10 or greater, an HLB value of about 11 or greater, an HLB value of about 12 or greater, an HLB value of about 13 or greater or an HLB value of about 14 or greater; and (iii) optionally at least one additional pharmaceutically acceptable excipient selected from the group consisting of stabilizers, fillers, lubricants, glidants, and combinations thereof.

In certain embodiments, the composition of the present invention is capsule, preferably a hard capsule wherein the contents of the capsule comprise:

(i) about 1 wt % to about 60 wt % based on the total weight of the solid composition or dosage form, preferably about 2 wt % to about 55 wt % and most preferably about 5 wt % to about 50 wt % of cabozantinib, preferably cabozantinib lauryl sulfate salt;

(ii) about 10 wt % to about 95 wt %, preferably about 15 wt % to about 90 wt % and most preferably about 20 wt % to about 85 wt % of one or more wetting agents, solubilizing agents, emulsifying agents, surfactants or combinations thereof that exhibits an HLB value of about 10 or greater, an HLB value of about 11 or greater, an HLB value of about 12 or greater, an HLB value of about 13 or greater or an HLB value of about 14 or greater;

(iii) about 1 wt % to about 50 wt %, preferably about 2 wt % to about 45 wt % and most preferably about 3 wt % to about 40 wt % of a secondary carrier that exhibits an HLB value of about less than 10, an HLB value about 9 or less, an HLB value about 8 or less, an HLB value about 7 or less, and wherein the secondary carrier is selected from the group consisting of wetting agents, solubilizing agents, emulsifying agents, surfactants or combinations thereof, and (iv) optionally at least one additional pharmaceutically acceptable excipient selected from the group consisting of stabilizers, fillers, lubricants, glidants, and combinations thereof.

In certain aspects of the preferred capsule embodiment, the one or more wetting agents, solubilizing agents, emulsifying agents, surfactants or combinations thereof that exhibits an HLB value of about 10 or greater is selected from the group consisting of fatty alcohol acid or amide ethoxylates, monoglyceride ethoxylates, sorbitan ester ethoxylates alkyl polyglycosides, polyoxyethylene castor oil, polyoxyethylene stearates, polyoxyethylene hydrogenated castor oil, poloxamer, tyloxapol, a fatty acid ester or fatty acid alcohol of a polyglyceride, vitamin E derivatives such as vitamin E polyethylene glycol succinate or combinations thereof and most preferably selected form the group consisting of polyoxyethylene castor oil, polyoxyethylene hydrogenated castor oil, polyoxyethylene stearates, poloxamer, a caprylic/capric triglyceride, vitamin E polyethylene glycol succinate or combinations thereof; In certain aspects of the preferred capsule embodiment, capsule content is free or substantially free of any polymer such as a binding polymer, viscosity enhancing polymer, disintegrant polymer, with a melting point above 100° C. As used in this context "free" means 0 wt % or below detectable limits and "substantially free" means less than 5 wt %, 3 wt %, 2 wt %, 1.5 wt %, 1.0 wt %, 0.75 wt % 0.5 wt %, 0.25 wt %, or 0.1 wt % based on the total weight of the contents of the capsule.

In certain aspects the compositions of the present invention are hard capsules wherein the contents of the capsules comprise:

(i) about 1 wt % to about 60 wt % based on the total weight of the capsule content, preferably about 2 wt % to about 55 wt % and most preferably about 5 wt % to about 50 wt % of cabozantinib, preferably cabozantinib lauryl sulfate salt;

(ii) about 10 wt % to about 95 wt %, preferably about 15 wt % to about 90 wt % and most preferably about 20 wt % to about 85 wt % of one or more wetting agents, solubilizing agents, emulsifying agents, surfactants or combinations thereof that exhibits an HLB value of about 12 to about 16 selected from the group consisting of fatty alcohol acid or amide ethoxylates, monoglyceride ethoxylates, sorbitan ester ethoxylates alkyl polyglycosides, polyoxyethylene castor oil, polyoxyethylene stearates, polyoxyethylene hydrogenated castor oil, poloxamer, tyloxapol, a fatty acid ester or fatty acid alcohol of a polyglyceride, vitamin E derivatives such as vitamin E polyethylene glycol succinate or combinations thereof and preferably selected form the group consisting of polyoxyethylene castor oil, polyoxyethylene hydrogenated castor oil, polyoxyethylene stearates, poloxamer, a caprylic/capric triglyceride, vitamin E polyethylene glycol succinate or combinations thereof; and (iii) optionally at least one stabilizer, filler, lubricant, glidant, and combinations thereof wherein the cabozantinib, preferably cabozantinib lauryl sulfate, is crystalline and either micronized or non-micronized.

In certain embodiments, the compositions of the present invention are capsules, preferably hard capsules, wherein the contents of the capsules comprise:

(i) about 5 wt % to about 50 wt % based on the total weight of the capsule content, preferably about 10 wt % to about 45 wt % and most preferably about 15 wt % to about 40 wt % of a cabozantinib pharmaceutically salt, preferably cabozantinib lauryl sulfate salt;

(ii) about 50 wt % to about 95 wt %, preferably about 55 wt % to about 90 wt % and most preferably about 60 wt % to about 85 wt % of one or more polyoxyethylene stearates that exhibits an HLB value of about 12 or higher; and (iii) optionally at least one additional pharmaceutically acceptable excipient selected from the group consisting of stabilizers, fillers, viscosity enhancing agents, binders, disintegrants, lubricants, glidants, flavoring agents, and combinations thereof.

In certain embodiments, the compositions of the present invention are capsules, preferably hard capsules, wherein the contents of the capsules comprise:

(i) about 5 wt % to about 50 wt % based on the total weight of the capsule content, preferably about 10 wt % to about 45 wt % and most preferably about 15 wt % to about 40 wt % of a cabozantinib pharmaceutically salt, preferably cabozantinib lauryl sulfate salt;

(ii) about 50 wt % to about 95 wt %, preferably about 55 wt % to about 90 wt % and most preferably about 60 wt % to about 85 wt % of one or more polyoxyethylene alkyl ethers that exhibits an HLB value of about 12 or higher; and (iii) optionally at least one additional pharmaceutically acceptable excipient selected from the group consisting of stabilizers, fillers, viscosity enhancing agents, binders, disintegrants, lubricants, glidants, flavoring agents, and combinations thereof.

In certain embodiments, the compositions of the present invention are capsules, preferably hard capsules wherein the contents of the capsules comprise:

(i) about 5 wt % to about 50 wt % based on the total weight of the capsule content, preferably about 10 wt % to about 45 wt % and most preferably about 15 wt % to about 40 wt % of a cabozantinib pharmaceutically salt, preferably cabozantinib lauryl sulfate salt;

(ii) about 50 wt % to about 95 wt %, preferably about 55 wt % to about 90 wt % and most preferably about 60 wt % to about 85 wt % of one or more polyoxyethylene-polyoxypropylene copolymer that exhibits an HLB value of about 12 or higher; and (iii) optionally at least one additional pharmaceutically acceptable excipient selected from the group consisting of stabilizers, fillers, viscosity enhancing agents, binders, disintegrants, lubricants, glidants, flavoring agents, and combinations thereof.

In certain embodiments, the compositions of the present invention are capsules, preferably hard capsules wherein the contents of the capsules comprise:

(i) about 5 wt % to about 50 wt % based on the total weight of the capsule content, preferably about 10 wt % to about 45 wt % and most preferably about 15 wt % to about 40 wt % of a cabozantinib pharmaceutically salt, preferably cabozantinib lauryl sulfate salt;

(ii) about 50 wt % to about 95 wt %, preferably about 55 wt % to about 90 wt % and most preferably about 60 wt % to about 85 wt % of one or more polyglyceride fatty acid esters that exhibits an HLB value of about 12 or higher; and (iii) optionally at least one additional pharmaceutically acceptable excipient selected from the group consisting of stabilizers, fillers, viscosity enhancing agents, binders, disintegrants, lubricants, glidants, flavoring agents, and combinations thereof.

In certain embodiments, the compositions of the present invention are capsules, preferably hard capsules wherein the contents of the capsules comprise:

(i) about 5 wt % to about 50 wt % based on the total weight of the capsule content, preferably about 10 wt % to about 45 wt % and most preferably about 15 wt % to about 40 wt % of a cabozantinib pharmaceutically salt, preferably cabozantinib lauryl sulfate salt;

(ii) about 50 wt % to about 95 wt %, preferably about 55 wt % to about 90 wt % and most preferably about 60 wt % to about 85 wt % of one or more polyglyceride fatty acid alcohols that exhibits an HLB value of about 12 or higher; and (iii) optionally at least one additional pharmaceutically acceptable excipient selected from the group consisting of stabilizers, fillers, viscosity enhancing agents, binders, disintegrants, lubricants, glidants, flavoring agents, and combinations thereof.

In certain embodiments, the compositions of the present invention are capsules, preferably hard capsules wherein the contents of the capsules comprise:

(i) about 5 wt % to about 50 wt % based on the total weight of the capsule content, preferably about 10 wt % to about 45 wt % and most preferably about 15 wt % to about 40 wt % of a cabozantinib pharmaceutically salt, preferably cabozantinib lauryl sulfate salt;

(ii) about 50 wt % to about 95 wt %, preferably about 55 wt % to about 90 wt % and most preferably about 60 wt % to about 85 wt % of one or more vitamin E derivatives that exhibits an HLB value of about 12 or higher; and (iii) optionally at least one additional pharmaceutically acceptable excipient selected from the group consisting of stabilizers, fillers, viscosity enhancing agents, binders, disintegrants, lubricants, glidants, flavoring agents, and combinations thereof.

Examples of stabilizers that may be used in the present invention include, but are not limited to, antioxidants, drying agents, buffers, pH adjusting agents, or combination thereof. The stabilizer(s) if present in the dosage form should be less than about 20% of the total weight of the composition, preferably less than about 15% of the total weight of the composition, and most preferably less than about 10% of the total weight of the composition. In certain embodiments, the stabilizer may be present in the composition in an amount of about 0.01 wt %, 0.02 wt %, 0.03 wt %, 0.04 wt %, 0.05 wt %, 0.06 wt %, 0.07 wt %, 0.08 wt %, 0.09 wt %, 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.2 wt %, 1.3 wt %, 1.4 wt %, 1.5 wt %, 1.6 wt %, 1.7 wt %, 1.8 wt %, 1.9 wt %, 2.0 wt %, 2.1 wt %, 2.2 wt %, 2.3 wt %, 2.4 wt %, 2.5 wt %, 2.6 wt %, 2.7 wt %, 2.8 wt %, 2.9 wt %, 3.0 wt %, 3.1 wt %, 3.2 wt %, 3.3 wt %, 3.4 wt %, 3.5 wt %, 3.6 wt %, 3.7 wt %, 3.8 wt %, 3.9 wt % 4.0 wt % 4.1 wt %, 4.2 wt %, 4.3 wt %, 4.4 wt %, 4.5 wt %, 4.6 wt %, 4.7 wt %, 4.8 wt %, 4.9 wt %, 5.0 wt % or any range encompassed by the foregoing values.

Examples of antioxidants that may be used in the present invention include, but are not limited to, ascorbic acid, ascorbyl palmitate (AP), butylated hydroxyanisole (BHA), butylated hydroxytoluene (BHT), citric acid, ethyl oleate, fumaric acid, hypophosphorous acid, malic acid, monothioglycerol, potassium metabisulfite, propyl gallate, sodium bisulfite, sodium formaldehyde sulfoxylate, sodium metabisulfite, sodium sulfite, sodium thiosulfate, sulfur dioxide, tocopherols, methylparaben, ethylparaben, propylparaben, butylparaben, benzyl benzoate, pyridoxine, ethyl vanillin and mixtures thereof. Preferred antioxidants for use according to the invention include BHT, BHA, AP, propyl gallate, alpha tocopherol, or any mixtures thereof. Generally, the amount antioxidant present in the composition of the present invention will comprise about 0.0001 wt % to about 5 wt %, preferably about 0.01 wt % to about 2 wt %, and most preferably about 0.05 wt % to about 1 wt % based on the total weight of the composition.

As used herein, and unless otherwise defined, the term “drying agent” refers to pharmaceutically acceptable excipients that have the ability to bind or absorb water present in the composition. Examples of a drying agent useful in the present invention may include, for example, magnesium oxide (MgO), aluminum oxide, attapulgite, bentonite, kaolin, pectin, saponite, colloidal silicon dioxide, and mixtures thereof. Depending upon the specific dosage form, the viscosity enhancing agents discussed below may also be used as a drying agent. The amount of drying agent, if present, in the composition of the present invention can range from about 0.05 wt % to about 10 wt % of the total weight of the composition, preferably about 0.1 wt % to about 5 wt % of the total weight of the composition, and most preferably about 0.5 wt % to about 2.5 wt % of the total weight of the composition.

Examples of buffers that may be used in the present invention include, but are not limited to, acetic acid, adipic acid, ammonium carbonate, ammonium phosphate, boric acid, citric acid, lactic acid, phosphoric acid, potassium citrate, potassium phosphate, sodium acetate, sodium citrate, sodium carbonate, potassium carbonate, sodium bicarbonate, potassium bicarbonate, sodium lactate, sodium phosphate, succinic acid, and combinations thereof. Typically, the buffer will comprise a combination of the foregoing as to create a buffer system such as citric acid and sodium citrate or acetic acid and sodium acetate.

Examples of pH adjusting agents that may be used in the present invention include, but are not limited to, any of the pharmaceutically acceptable acids or bases used to adjust the pH of pharmaceutical compositions. Examples of compounds typically used to adjust the pH of pharmaceutical compositions include hydrochloric acid, citric acid, lactic acid, tartaric acid, glacial acetic acid, sodium hydroxide, potassium hydroxide, arginine, lysine, meglumine, triethanol amine, or combinations thereof.

If employed, the buffer and/or pH adjusting agent may comprise about 0.01 wt % to about 20 wt % of the composition, preferably about 0.1 wt % to about 10 wt % of the composition, and most preferably about 0.5 wt % to about 5 wt % of the composition.

Fillers, sometimes referred to as diluents, may also be used in the present invention and include water; sugars such as lactose, dextrose, sucrose, maltose, or microcrystalline cellulose; clays, and mixtures thereof. Generally, the amount filler present in the compositions of the present invention will comprise about 0 wt % to about 90 wt %, preferably about 0.01 wt % to about 80 wt %, and most preferably about 1 wt % to about 70 wt % based on the total weight of the composition.

Viscosity enhancing agents that may be used in the present invention include organic materials such as natural or synthetic waxes, $C_{12}$-$C_{60}$ alcohols, $C_{12}$-$C_{60}$ acids, alpha-hydroxy fatty acids, polyhydroxy fatty acid esters, polyhydroxy fatty acid amides, and inorganic/organic materials such as metal ester complexes containing zinc, calcium, aluminum or magnesium, fumed silicas, and organoclays. Additional viscosity enhancing agents include polyol polyesters, glyceryl esters, polyglyceryl esters, and polysiloxanes.

Waxes are also suitable for use as viscosity enhancing agents in compositions of the present invention. Natural waxes may include, but are not limited to, carnauba, ozokerite, beeswax, candelilla, paraffin, ceresin, esparto, ouricuri, rezowax and other known mined and mineral waxes. Synthetic waxes may include, but are not limited to, paraffin waxes and microcrystalline waxes.

Still further viscosity enhancing agents that may be included in the compositions of the present invention are gelling agents. Gelling agents are materials that can swell or expand when in contact with water. Examples of gelling agents that may be used in the present invention include swellable polymers, also known as osmopolymers or hydrogels. The swellable polymer can be non-cross-linked or lightly cross-linked. The cross-links can be covalent or ionic bonds with the polymer possessing the ability to swell in the presence of fluid, and when cross-linked, it will not be dissolved in the fluid. The polymer can be of plant, animal, or synthetic origin. Polymeric gelling agents useful for the present purpose include polyhydroxyalkylcellulose having a molecular weight greater than 50,000, such as hydroxyl propylmethylcellulose (METHOCEL K 100M available from Dow Chemical); poly(hydroxyalkylmethacrylate) having a molecular weight of from 5,000 to 5,000,000; poly (vinylpyrrolidone) having a molecular weight of from 100,000 to 3,000,000; anionic and cationic hydrogels; poly (electrolyte) complexes; poly(vinylalcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; a water-swellable copolymer produced by a dispersion of a finely divided copolymer of maleic anhydride with styrene, ethylene, propylene, or isobutylene; a water-swellable polymer of N-vinyl lactams, and the like.

Other gelling agents useful in the present invention include pectin having a molecular weight ranging from 30,000 to 300,000; polysaccharides such as agar, acacia, karaya, tragacanth, algins and guar; CARBOPOL® an acrylic acid polymer, a carboxyvinyl polymer, sometimes referred to as carboxypolymethylene, a polymer of acrylic acid cross-linked with a polyallyl ether of sucrose, as described in U.S. Pat. Nos. 2,798,053 and 2,909,462 and available as CARBOPOL® 934, 940 and 941, and its salt derivatives; polyacrylamides; water-swellable indene maleic anhydride polymers; GOOD-RITE® polyacrylic acid having a molecular weight of 80,000 to 200,000; POLYOX™ polyethylene oxide polymers having a molecular weight of 100,000 to 7,000,000; starch graft copolymers; AQUA-KEEP™ acrylate polymers with water absorbability of about 400 times its original weight; diesters of polyglucan; a mixture of cross-linked polyvinyl alcohol and poly(N-vinyl-2-pyrrolidone); poly(ethylene glycol) having a molecular weight of 4,000 to 100,000. Representative polymers possessing gelling properties are described in U.S. Pat. Nos. 6,419,954, 4,915,949, 4,327,725, 4,207,893 and in Handbook of Common Polymers, by Scott and Roff, published by Cleveland Rubber Company, Cleveland, Ohio.

Generally, the amount of viscosity enhancing agent present in the compositions of the present invention will comprise about 0 wt % to about 30 wt %, preferably about 0.01 wt % to about 25 wt %, and most preferably about 1 wt % to about 15 wt % based on the total weight of the composition. In certain embodiments, the amount of viscosity enhancing agent present in the compositions of the present invention will comprise about 5 wt % to about 60 wt %, preferably about 10 wt % to about 55 wt %, and most preferably about 15 wt % to about 50 wt % based on the total weight of the composition. In the semi-solid embodiments of the present invention, the viscosity enhancing agent that is a solid at ambient temperatures but that exhibits a melting point below 120° C., preferably below 100° C., more preferably below 80° C. and most preferably below 60° C. as discussed above and may comprise about 7.5 wt % to about 75 wt %, preferably about 10 wt % to about 60 wt % and most preferably about 12 wt % to about 50 wt % of the total weight of the composition. Examples of these viscosity enhancing agents include but are not limited to the natural or synthetic waxes such as carnauba wax, cetyl ester wax, microcrystalline wax, white wax, yellow wax, bees wax, ozokerite, paraffin, ceresin, esparto, ouricuri, and rezowax, hard fats (aka hydrogenated vegetable glycerides), hydrogenated vegetable oils, $C_{12}$-$C_{60}$ alcohols, $C_{12}$-$C_{60}$ acids, alpha-hydroxy fatty acids, polyhydroxy fatty acid esters, polyhydroxy fatty acid amides and combinations thereof described above.

Examples of binders that may be employed in the solid dosage form of the present invention include acacia, povidone, hypromellose, hydroxypropyl cellulose, hydroxyethyl cellulose, polyethylene oxide, polymethacrylates, methyl cellulose, ethyl cellulose, pregelatinized starch, gelatin, tragacanth, zein, or mixtures thereof. Preferably, the binder is selected from povidone, hypromellose, hydroxypropyl cellulose, hydroxyethyl cellulose, polymethacrylates, methyl cellulose, gelatin and ethyl cellulose, or mixtures thereof. Especially preferred binders include water soluble binders such as povidone, hypromellose, hydroxypropyl cellulose, gelatin and mixtures thereof. If the binder is a polymeric binder, it is preferred that the binder have a low molecular weight and/or exhibit a viscosity of less than 200 mPa s, preferably less than 100 mPa s, and most preferably less than 50 mPa s when tested at a concentration of 2% (w/v) aqueous preparation at 20° C.

Generally, the amount binder present in the compositions of the present invention will comprise about 0 wt % to about 30 wt %, preferably about 0.01 wt % to about 25 wt %, and most preferably about 1 wt % to about 15 wt % based on the total weight of the composition.

Examples of disintegrants that may be employed in the solid dosage form of the present invention include croscarmellose sodium, starch, crospovidone, sodium starch glycolate, alginic acid, calcium carboxymethylcellulose, sodium carboxymethylcellulose, potassium carboxymethylcellulose, powdered cellulose, chitosan, guar gum, magnesium aluminum silicate, methylcellulose, sodium alginate, and mixtures thereof. Generally, the amount of disintegrant present in the compositions of the present invention will comprise about 0 wt % to about 40 wt %, preferably about 1 wt % to about 25 wt %, and most preferably about 2 wt % to about 20 wt % based on the total weight of the composition.

Examples of lubricants that may be employed in the solid dosage form of the present invention include magnesium stearate, sodium stearyl fumarate, stearic acid, glyceryl behenate, polyethylene glycols (preferably wherein the polyethylene glycol has a molecular weight of 6000 or more), polyoxyethylene stearate, magnesium lauryl sulfate, sodium oleate, and mixtures thereof. The lubricants may be present in an amount ranging from about 0.1 wt % to about 10 wt % based on the total weight of the dosage form, preferably about 0.2 wt % to about 7 wt %, and most preferably about 0.5 wt % to about 5 wt %.

Examples of glidants that may be employed in the solid dosage form of the present invention include colloidal silicon dioxide, corn starch, talc and mixtures thereof. The glidants may be present in an amount ranging from about 0.1 wt % to about 10 wt % based on the total weight of the dosage form, preferably about 0.2 wt % to about 7 wt %, and most preferably about 0.5 wt % to about 5 wt %.

Examples of flavoring agents that may be employed in the solid dosage form of the present invention include artificial sweeteners such as aspartame, saccharin, dipotassium glycyrrhizinate, stevia, thaumatin, and flavorants such as citric acid, peppermint oil, wintergreen oil, menthol, lemon, lime, orange, grape, cherry, and vanilla extract. Additional taste enhancing agents are described in U.S. Pat. No. 6,027,746, which is incorporated herein by reference.

In certain embodiments of the present invention, the dissolution rate of oral dosage forms when tested using a USP Type II Apparatus (Paddle) with 500 ml to 900 ml of 0.01 N HCl at 50-75 rpm, with or without a sinker, with or without a surfactant and 37° C. as follows:

| Time (minutes) | Preferred | More Preferred | Most Preferred |
|---|---|---|---|
| 15 | NLT 10% | NLT 20% | NLT 30% |
| 30 | NLT 30% | NLT 40% | NLT 50% |

-continued

| Time (minutes) | Preferred | More Preferred | Most Preferred |
|---|---|---|---|
| 45 | NLT 40% | NLT 45% | NLT 50% |
| 60 | NLT 70% | NLT 75% | NLT 85% |

*NLT: not lower than

In certain embodiments of the present invention, the dissolution rate of oral dosage forms when tested using a USP Type II Apparatus (Paddle) with 500 ml to 900 ml of 0.01 N HCl at 50-75 rpm, with a sinker, with 0.02%-0.5% of a surfactant and 37° C. as follows:

| Time (minutes) | Preferred | More Preferred | Most Preferred |
|---|---|---|---|
| 15 | 0-100% | 1%-100% | 2.5%-100% |
| 30 | 10%-100% | 15%-100% | 20%-100% |
| 45 | 25%-100% | 30%-100% | 35%-100% |
| 60 | 40%-100% | 45%-100% | 50%-100% |

In certain embodiments of the present invention, the dissolution rate of oral dosage forms when tested using a USP Type II Apparatus (Paddle) with 500 ml to 900 ml of 0.01 N HCl at 50-75 rpm, with a stationary basket, with 0.02% to 0.5% of a surfactant and 37° C. as follows:

| Time (minutes) | Preferred | More Preferred | Most Preferred |
|---|---|---|---|
| 15 | 10-95% | 20%-90% | 25%-85% |
| 30 | 30%-100% | 40%-100% | 50%-100% |
| 45 | 40%-100% | 45%-100% | 60%-100% |
| 60 | NLT 50% | NLT 60% | NLT 70% |

In certain embodiments of the present invention, the dissolution rate of oral dosage forms will when tested using a USP Type II Apparatus (Paddle) with 500 ml to 900 ml of pH 4.5 Acetate Buffer Solution at 50-75 rpm, with or without a sinker, with or without a surfactant and 37° C. as follows:

| Time (minutes) | Preferred | More Preferred | Most Preferred |
|---|---|---|---|
| 15 | NLT 10% | NLT 20% | NLT 30% |
| 30 | NLT 30% | NLT 40% | NLT 50% |
| 60 | NLT 60% | NLT 65% | NLT 75% |

In certain embodiments of the present invention, the dissolution rate of oral dosage forms will when tested using a USP Type II Apparatus (Paddle) with 500 ml to 900 ml of pH 4.5 Acetate Buffer Solution at 50-75 rpm, with a sinker, with 0.02% to 0.5% of a surfactant and 37° C. as follows:

| Time (minutes) | Preferred | More Preferred | Most Preferred |
|---|---|---|---|
| 15 | 0-70% | 1%-65% | 1.5%-60% |
| 30 | 5%-100% | 7.5%-100% | 10%-100% |
| 45 | 5%-100% | 7.5%-100% | 10%-100% |
| 60 | 5%-100% | 7.5%-100% | 10%-100% |

In certain embodiments of the present invention, the dissolution rate of oral dosage forms will when tested using a USP Type II Apparatus (Paddle) with 500 ml to 900 ml of pH 4.5 Acetate Buffer Solution at 50-75 rpm, with a stationary basket, with 0.2% to 0.5% of a surfactant and 37° C. as follows:

| Time (minutes) | Preferred | More Preferred | Most Preferred |
|---|---|---|---|
| 15 | 5%-80% | 10%-75% | 15%-70% |
| 30 | 25%-100% | 30%-100% | 35%-100% |
| 45 | 40%-100% | 45%-100% | 50%-100% |
| 60 | NLT 65% | NLT 70% | NLT 75% |

The compositions and dosage forms of the present invention will be stable when prepared and stored under normal and accelerated conditions. More specifically, the dosage forms of the present invention will contain about 1.0% or less of any individual degradation product, preferably about 0.75% or less of any individual degradation product, and most preferably about 0.5% or less of any individual degradation product when the dosage form is stored in a sealed bottle, preferably a sealed plastic bottle such as a high density polyethylene bottle (with or without a desiccant), at approximately 25° C. and approximately 60% relative humidity for at least three months, preferably at least six months and most preferably at least one year and/or at approximately 40° C. and approximately 75% relative humidity for one month, two months, or three months.

The compositions and dosage forms of the present invention should also contain a total amount of degradation products of about 2.0% or less, preferably about 1.5% or less, and most preferably about 1.0% or less when the dosage form is stored in a sealed bottle, preferably a sealed plastic bottle such as a high density polyethylene bottle (with or without a desiccant) at approximately 25° C. and approximately 60% relative humidity for at least three months, preferably at least six months, and most preferably at least one year and/or at approximately 40° C. and approximately 75% relative humidity for one month, two months, or three months.

The cabozantinib, preferably cabozantinib lauryl sulfate, employed in the compositions and dosage forms of the present invention can be in an amorphous form, a crystalline form or combination of amorphous and crystalline forms. In certain aspects, the cabozantinib, preferably cabozantinib lauryl sulfate, is substantially, i.e., greater than 50%, 60%, 70%, 80%, 90% or 100%, crystalline. The cabozantinib, preferably cabozantinib lauryl sulfate, may also be micronized or non-micronized when incorporated into the compositions and dosage forms of the present invention. In certain aspects, the cabozantinib, preferably cabozantinib lauryl sulfate, may have a particle size D90 of less than 100 μm, preferably a D90 of less than 90 μm and more preferably a D90 of less than 85 μm. Alternatively, in certain aspects the cabozantinib, preferably cabozantinib lauryl sulfate, may have a particle size D50 of less than 75 μm, preferably a D50 of less than 65 μm and more preferably a D50 of less than 55 μm and/or a D10 of less than 40 μm, preferably a D10 of less than 35 μm and more preferably a D10 of less than 25 μm.

In certain embodiments, the crystalline cabozantinib lauryl sulfate employed in the present invention will be crystalline cabozantinib monolauryl sulfate and will exhibit one, two, three, four or more of the following 2θ peaks in an X-Ray Powder Diffraction (XRPD) analysis: 5.0±0.2; 11.3±0.2; 12.1±0.2; 13.5±0.2; 16.8±0.2; 17.5±0.2; 18.6±0.2; 20.2±0.2; 20.6±0.2; 21.3±0.2; 21.9±0.2; 22.4±0.2; 22.7±0.2; 23.2±0.2, 24.2±0.2; 26.6±0.2; and/or 27.7±0.2.

The amount of cabozantinib, preferably cabozantinib lauryl sulfate salt, that will be present in the dosage forms of the present invention will comprise about 5 mg to about 120 mg, about 5 mg to about 100 mg, about 5 mg to about 80 mg, about 7.5 mg to about 100 mg, about 7.5 mg to about 80 mg, about 7.5 mg to about 70 mg, about 10 mg to about 50 mg, about 10 mg to about 60 mg, about 10 mg to about 80 mg, about 12 mg to about 60 mg, about 12 mg to about 50 mg and about 12 mg to about 45 mg of cabozantinib base preferably in the form of a cabozantinib slat and more preferably in the form of cabozantinib lauryl sulfate salt.

The present invention includes methods for treating the various cancers including but not limited to cancers such renal cell carcinoma, hepatocellular carcinoma and medullary thyroid cancer. In certain embodiments:

(i) the oral administration may be with or without food and the oral administration will exhibit substantially similar, equivalent or constant pharmacokinetic values or will not exhibit a food effect as described in detail below;

(ii) the oral administration will allow for a reduction in the total daily dose of cabozantinib compared to the currently U.S. FDA approved CABOMETYX® tablets and/or COMETRIQ® capsules while maintaining similar pharmacokinetics as described in detail below;

(iii) the oral administration will also lower occurrence or severity of one or more adverse events as listed in the following table compared to the commercially available CABOMETYX® tablets and/or COMETRIQ® capsules having an amount of cabozantinib (S)-malate that provides a similar or an equivalent $C_{max}$ and/or AUC, collectively a similar or an equivalent bioavailability, as the oral cabozantinib composition of the present invention:

| System Organ Class | Adverse Reaction |
|---|---|
| Gastrointestinal Disorders | Gastrointestinal perforations and/or fistula; Diarrhea; Nausea; Vomiting; Stomatitis; Constipation; Abdominal pain; Dyspepsia |
| General | Fatigue |
| Metabolism and Nutrition Disorders | Decreased appetite |
| Vascular | Hypertension |
| Investigation Disorders | Weight decreased |

(iv) exhibits lower inter-subject variability for at least one pharmacokinetic parameter (i.e., $C_{max}$, $AUC_{0-t}$ and $AUC_{0-infinity}$) compared to the commercially available CABOMETYX® tablets and/or COMETRIQ® capsules, when administered orally to human subjects; or (v) the oral administration will exhibit a combination of (i), (ii), (iii) and/or (iv).

In certain embodiments, the present invention includes methods for treating the above-identified cancers by orally administering one or more dosage forms described herein and comprising about 5 mg to about 100 mg, preferably about 7.5 mg to about 80 mg and more preferably about 10 mg to about 50 mg of cabozantinib base in the form of the cabozantinib sulfate salt. In these embodiments:

(i) the oral administration may be with or without food and the oral administration will exhibit substantially similar, equivalent or constant pharmacokinetic values or will not exhibit a food effect as described in detail below;

(ii) the oral administration will allow for a reduction in the total daily dose of cabozantinib compared to the currently U.S. FDA approved CABOMETYX® tablets and/or COMETRIQ® capsules while maintaining similar pharmacokinetics as described in detail below;

(iii) the oral administration will reduce the occurrence and/or severity of diarrhea compared to compared to the currently U.S. FDA approved CABOMETYX® tablets and/or COMETRIQ® capsules; or (iv) the oral administration will exhibit a combination of (i); (ii) and/or (iii).

The compositions and dosage forms of the present invention can be administered to a subject, wherein the subject may be either in a fed state or a fasted state and the administration will under either fed or fasted conditions will result in substantially similar, equivalent or constant pharmacokinetic values or no food effect. In general, a fed state is defined as having consumed food within about 30 minutes prior to administration of the composition or dosage form. The food may be a high fat meal, a low fat meal, a high calorie meal, or a low calorie meal. A fasted state may be defined as not having ingested food for up to 10 hours prior to administration of the composition or dosage form. In some embodiments, the subject may have fasted for at least 10 hours prior to administration and refrains from ingesting food for about 30 minutes to 2 hours, preferably about one hour following administration. In other embodiments, the fasted subject may not have ingested food for at least 1 hour, 2 hours, 3 hours, 4 hours, 5 hours, 6 hours, 7 hours, 8 hours, 9 hours, or 10 hours prior to administration of each dose of the composition or dosage form.

The method of orally administering the composition and/or dosage form of the present invention to a patient or healthy subject will produce substantially similar, equivalent or constant pharmacokinetic values such as $T_{max}$, $C_{max}$ and AUC whether the composition is administered with or without food. A substantially similar, equivalent or constant pharmacokinetic value means the measured pharmacokinetic value obtained after a single or multiple dose administration of the composition or dosage form to a patient or healthy subject under fasted conditions as described by the U.S. FDA Guidance documents does not change by more than 40%, preferably does not change by more than 30% and most preferably does not change by more than 20% when the same composition is administered to the same patient or healthy subject under fed conditions as described in the U.S. FDA Guidance documents. For example, if a $T_{max}$ of 3 hours was obtained after a single dose administration to a patient under fasted conditions, a $T_{max}$ in the range of 1.8 hours to 4.2 hours would be considered substantially constant, i.e., 3 hours±40%.

In certain preferred embodiments of the present invention, a single oral dose administration of a composition or dosage form prepared in accordance with the present invention will be bioequivalent when administered under fed and fasted conditions or exhibit no food effect. The terms "bioequivalent" and "no food effect" are used in accordance with the U.S. FDA Guidance documents.

In certain embodiments of the present invention, a single oral administration of the composition or dosage form prepared in accordance with the present invention will produce a ratio of the cabozantinib $C_{max}$ administered with food to the cabozantinib $C_{max}$ administered without food ($C_{max\ fed}/C_{max\ fasted}$) of about 0.60 to about 2.5, preferably about 0.70 to about 2.0, more preferably about 0.75 to about 1.5 and most preferably about 0.8 to about 1.25. In certain embodiments of the present invention, a single oral administration of the composition or dosage form prepared in accordance with the present invention will produce a ratio of the cabozantinib $AUC_{0-t}$ of the pharmaceutical composition administered with food to the cabozantinib $AUC_{0-t}$ of the pharmaceutical composition administered without food ($AUC_{0-t\ fed}/AUC_{0-t\ fasted}$) of about 0.60 to about 2.5, preferably about 0.70 to about 2.0, more preferably about 0.75 to about 1.5 and most preferably about 0.8 to about 1.25. Similarly, in certain embodiments of the present invention, a single oral administration of the composition or dosage form prepared in accordance with the present invention will produce a ratio of the cabozantinib $AUC_{0-\infty}$ of the pharmaceutical composition administered with food to the cabozantinib $AUC_{0-\infty}$ of the pharmaceutical composition administered without food ($AUC_{0-\infty\ fed}/AUC_{0-\infty\ fasted}$) of about 0.60 to about 2.5, preferably about 0.70 to about 2.0, more preferably about 0.75 to about 1.5 and most preferably about 0.8 to about 1.25.

Upon oral administration of the compositions or dosage forms of the present invention a cabozantinib plasma profile is obtained wherein at least one pharmacokinetic parameter differs by less than about 40% under fed and fasted conditions. In various embodiments, the pharmacokinetic parameter may vary by less than about 35%, 30%, 25%, 20%, 15%, 10%, or 5% under fed and fasted conditions. The pharmacokinetic parameter that is independent of food may be, but is not limited to, $C_{max}$, AUC, $T_{max}$, or combinations thereof.

Certain embodiments of the present invention include methods for treating cancer in human patients comprising the step of orally administering to the patient one or more dosage forms as described herein wherein the administration may be with or without food and wherein the dose of the cabozantinib lauryl sulfate salt does not require an adjustment in dose or a change in time of administration.

In certain embodiments, the administration of compositions or dosage forms prepared in accordance with the present invention may allow for a reduction in the amount of cabozantinib base currently approved by the U.S. FDA for the CABOMETYX® tablets and/or COMETRIQ® capsules and still obtain an equivalent therapeutic plasma level of cabozantinib. More specifically, the compositions of the present invention will allow at least a 10%, 15%, 20%, 25%, 30%, 35% 40%, 45%, 50%, 55% or 60% reduction in the daily amount of cabozantinib free base and still provide equivalent therapeutic plasma levels.

In certain embodiments of the present invention, the reduction in dose will result in a $C_{max}$ of at least about 7.0 ng/mL/mg of cabozantinib free base administered, at least about 7.5 ng/mL/mg of cabozantinib free base administered, at least about 8.0 ng/mL/mg of cabozantinib free base administered, at least about 8.5 ng/mL/mg of cabozantinib free base administered, at least about 9.0 ng/mL/mg of cabozantinib free base administered, at least about 9.5 ng/mL/mg of cabozantinib free base administered, at least about 10.0 ng/mL/mg of cabozantinib free base administered, at least about 10.5 ng/mL/mg of cabozantinib free base administered, at least about 11 ng/mL/mg of cabozantinib free base administered, at least about 11.5 ng/mL/mg of cabozantinib free base administered or at least about 12 ng/mL/mg of cabozantinib free base administered. In certain embodiments the $C_{max}$ will range from at least about 7.0 ng/mL/mg to about 25 ng/mL/mg of cabozantinib free base administered, preferably at least about 7.5 ng/mL/mg to about 20 ng/mL/mg of cabozantinib free base administered and more preferably at least about 8.0 ng/mL/mg to about 15 ng/mL/mg of cabozantinib free base administered. The foregoing values are based on single dose administrations to adult healthy humans or adult human cancer patients under fasted conditions.

In certain embodiments of the present invention, the reduction in dose will result in a $AUC_{0-\infty}$ of at least about 550 ng·hr/mL/mg of cabozantinib free base administered, at least about 575 ng·hr/mL/mg of cabozantinib free base administered, at least about 600 ng·hr/mL/mg of cabozantinib free base administered, at least about 625 ng·hr/mL/mg of cabozantinib free base administered, at least about 650 ng·hr/mL/mg of cabozantinib free base administered, or at least about 675 ng·hr/mL/mg of cabozantinib free base administered. In certain embodiments the $AUC_{0-\infty}$ will range from at least about 550 ng·hr/mL/mg to about 1200 ng·hr/mL/mg of cabozantinib free base administered, preferably at least about 575 ng·hr/mL/mg to about 1000 ng·hr/mL/mg of cabozantinib free base administered and more preferably at least about 600 ng·hr/mL/mg to about 800 ng·hr/mL/mg of cabozantinib free base administered. The foregoing values are based on single dose administrations to adult healthy humans or adult human cancer patients under fasted conditions.

The present invention also includes methods for preparing cabozantinib that can be used in the dosage forms of the present invention. The method comprises the steps of:

(a) reacting a 4-halo-6,7-dimethoxyquinoline with p-aminophenol to produce 4-((6,7-dimethoxyquinolin-4-yl)oxy)aniline;

(b) reacting 4-((6,7-dimethoxyquinolin-4-yl)oxy)aniline with 1,1-cyclopropanedicarboxylic acid to produce 1-((4-((6,7-dimethoxyquinolin-4-yl)oxy)phenyl) carbamoyl)cyclopropane-1-carboxylic acid; and (c) reacting 1-((4-((6,7-dimethoxyquinolin-4-yl)oxy)phenyl)carbamoyl)cyclopropane-1-carboxylic acid with 4-fluoroaniline to produce crude cabozantinib free base.

The present invention also includes methods for preparing cabozantinib lauryl sulfate salts that can be used in the dosage forms of the present invention. The method comprises the steps of:

(a) reacting a 4-halo-6,7-dimethoxyquinoline with p-aminophenol to produce 4-((6,7-dimethoxyquinolin-4-yl)oxy)aniline;

(b) reacting 4-((6,7-dimethoxyquinolin-4-yl)oxy)aniline with 1,1-cyclopropanedicarboxylic acid to produce 1-((4-((6,7-dimethoxyquinolin-4-yl)oxy)phenyl) carbamoyl)cyclopropane-1-carboxylic acid;

(c) reacting 1-((4-((6,7-dimethoxyquinolin-4-yl)oxy)phenyl)carbamoyl)cyclopropane-1-carboxylic acid with 4-fluoroaniline to produce crude cabozantinib free base; and (d) reacting the crude cabozantinib free base with a lauryl sulfate salt to produce cabozantinib lauryl sulfate salt.

The above process may be conducted using various solvents known to the skilled artisan and specifically described below in the examples.

The resulting cabozantinib lauryl sulfate salt is preferably crystalline, pure and stable. As used herein pure means the cabozantinib lauryl sulfate salt has less than 0.2%, less than 0.15%, less than 0.1%, or less than 0.05% based of any individual impurities, including but not limited the individual impurities identified in Example 25 herein and less than 2%, less than 1.5%, less than 1% of total impurities. As used herein stable means the cabozantinib lauryl sulfate exhibits the afore-described purity after storage for at least 6 months, 12 months, 18 months, 24 months or longer when stored in a sealed plastic container with or without desiccant at room temperature or at least 1 month, 2 months, 3, months, 4 months, 5 months, 6 months or longer when stored in a sealed plastic container, with or without a desiccant, at 40° C. and 75% relative humidity.

In certain embodiments, cabozantinib or the salt, preferably the cabozantinib lauryl sulfate salt, is stable and has:

(a) less than 0.2%, less than 0.15%, less than 0.1%, or less than 0.05% of (N,N'-bis(4-((6,7-dimethoxyquinolin-4-yl)oxy)phenyl)cyclopropane-1,1-dicarboxamide);

(b) less than 0.2%, less than 0.15%, less than 0.1%, or less than 0.05% of (N-(4-((6,7-dimethoxyquinolin-4-yl)oxy)phenyl)-N-phenylcyclopropane-1,1-dicarboxamide);

(c) less than 0.2%, less than 0.15%, less than 0.1%, or less than 0.05% of N-(4-fluorophenyl)-N-(4-((6-hydroxy-7-methoxyquinolin-4-yl)oxy)phenyl)cyclopropane-1,1-dicarboxamide;

(d) less than 0.2%, less than 0.15%, less than 0.1%, or less than 0.05% of (N-(4-((6,7-dimethoxyquinolin-4-yl)oxy)phenyl)-N-(2-fluorophenyl)cyclopropane-1,1-dicarboxamide); or (e) any combination of the foregoing.

In certain embodiments, cabozantinib or the salt, preferably the cabozantinib lauryl sulfate salt, is stable and has:

(a) less than 250 ppm, less than 125 ppm, less than 37.5 ppm, less than 25 ppm, less than 15 ppm, less than 10 ppm, or less than 7.5 ppm of (4-((6,7-dimethoxyquinolin-4-yl)oxy)aniline);

(b) less than 250 ppm, less than 125 ppm, less than 37.5 ppm, less than 25 ppm, less than 15 ppm, less than 10 ppm, or less than 7.5 ppm of (6,7-dimethoxy-4-(4-nitrophenoxy)quinolone);

(c) less than 250 ppm, less than 125 ppm, less than 37.5 ppm, less than 25 ppm, less than 15 ppm, less than 10 ppm, or less than 7.5 ppm of 3,4-dimethoxyaniline;

(d) less than 250 ppm, less than 125 ppm, less than 37.5 ppm, less than 25 ppm, less than 15 ppm, less than 10 ppm, or less than 7.5 ppm of 4-aminophenol;

(e) less than 250 ppm, less than 125 ppm, less than 37.5 ppm, less than 25 ppm, less than 15 ppm, less than 10 ppm, or less than 7.5 ppm of 4-fluoroaniline; or (f) any combination of the foregoing.

DESCRIPTION OF EMBODIMENTS

The following are provided by way of example only and are by no means intended to be limiting.

Comparative Example 1

A cabozantinib (S)-malate tablet dosage form was prepared by the following processes:

(i) 2.028 g of cabozantinib (S)-malate was passed through 60 mesh sieve and blended with 2.486 g of microcrystalline cellulose PH102, 1.243 g of anhydrous lactose and 0.192 g of croscarmellose sodium (Part I) that had been previously passed through a 40 mesh sieve;

(ii) the mixture of step (i) was wet granulated with a granulating solution prepared by dissolving 0.192 g of hydroxypropyl cellulose EXF in 1.28 g of purified water;

(iii) the wet granules were passed through a 20 mesh sieve, dried in the oven at 60° C. to evaporate the purified water and the dry granules were passed through a 24 mesh sieve;

(iv) the dried and sieved granules were mixed with 0.192 g of croscarmellose sodium (Part II) and 0.019 g of colloidal silicon dioxide;

(v) 0.048 g of magnesium stearate was added to the mixture of step (iv) and blended well to obtain final blend; and (vi) the final blend was compressed into tablets using a 6 mm round-shaped punch and a target hardness of about 4 Kp.

The composition of the tablet content is as follows:

| Materials | mg | wt % |
|---|---|---|
| Cabozantinib (S)-malate, (EQ to 20 mg free base) | 25.345 | 31.68 |
| Microcrystalline cellulose PH102 | 31.08 | 38.85 |
| Lactose Anhydrous | 15.535 | 19.42 |
| Hydroxypropyl cellulose EXF | 2.40 | 3.00 |
| Croscarmellose Sodium (Part I) | 2.40 | 3.00 |
| Croscarmellose Sodium (Part II) | 2.40 | 3.00 |
| Colloidal Silicon Dioxide | 0.24 | 0.30 |
| Magnesium stearate | 0.60 | 0.75 |
| Total | 80.00 | 100.00 |
| Purified water | 16.00 | N/A |

The cabozantinib (S)-malate salt tablet was tested using a U.S.P. Type II (paddle) apparatus with the following conditions:

Condition: 0.01N HCl containing 0.5% TRITON™ X-100, 900 mL, Paddle with Sinker, 75 rpm, 37° C.

| Time | CT210812 (Ref) | |
|---|---|---|
| (minutes) | Avg. | % RSD |
| 10 | 92.3% | 4.3 |
| 15 | 97.0% | 3.9 |
| 20 | 100.2% | 4.0 |
| 30 | 99.6% | 3.5 |
| 45 | 98.8% | 4.6 |
| 60 | 101.1% | 2.8 |
| 75 (Infinity) | 97.6% | 2.7 |

TRITON™ X-100 is a commercially available non-ionic surfactant, also known as 2-[4-(2,4,4-trimethylpentan-2-yl)phenoxy]ethanol; octylphenol ethoxylate; t-octylphenoxypolyethoxyethanol; and polyethylene glycol tert-octylphenyl ether.

Condition: pH4.5 Acetate Buffer Solution ("ABS") containing 0.025% TRITON™ X-100, 900 mL, Paddle with Sinker, 75 rpm, 37° C.

| Time | CT210812 (Ref) | |
|---|---|---|
| (minutes) | Avg. | % RSD |
| 5 | 6.8% | N/A |
| 10 | 22.4% | N/A |
| 15 | 34.3% | N/A |
| 20 | 42.4% | N/A |
| 30 | 52.0% | N/A |
| 45 | 62.7% | N/A |
| 60 | 66.9% | N/A |
| 75 (Infinity) | 67.9% | N/A |

Condition: pH4.5 ABS containing 0.2% TRITON™ X-100, 900 mL, Paddle with Sinker, 75 rpm, 37° C.

| Time | CT210812 (Ref) | |
|---|---|---|
| (minutes) | Avg. | % RSD |
| 5 | 26.6% | N/A |
| 10 | 52.0% | N/A |
| 15 | 63.8% | N/A |
| 20 | 72.2% | N/A |
| 30 | 81.4% | N/A |
| 45 | 89.2% | N/A |
| 60 | 91.8% | N/A |
| 75 (Infinity) | 94.0% | N/A |

Condition: pH6.8 Phosphate Buffer Solution ("PBS"), 900 mL, Paddle with Sinker, 75 rpm, 37° C.

| Time | CT210812 (Ref) | |
|---|---|---|
| (minutes) | Avg. | % RSD |
| 5 | 0 | N/A |
| 10 | 0 | N/A |
| 15 | 0.3% | N/A |
| 20 | 0.7% | N/A |
| 30 | 1.6% | N/A |
| 45 | 2.3% | N/A |
| 60 | 3.1% | N/A |
| 75 (Infinity) | 4.0% | N/A |

Condition: pH6.8 PBS containing 0.025% TRITON™ X-100, 900 mL, Paddle with Sinker, 75 rpm, 37° C.

| Time | CT210812 (Ref) | |
|---|---|---|
| (minutes) | Avg. | % RSD |
| 15 | 0.8% | N/A |
| 20 | 2.0% | N/A |
| 30 | 3.2% | N/A |
| 45 | 3.7% | N/A |
| 60 | 4.4% | N/A |

Condition: pH6.8 PBS containing 0.2% TRITON™ X-100, 900 mL, Paddle with Sinker, 75 rpm, 37° C.

| Time | CT210812 (Ref) | |
|---|---|---|
| (minutes) | Avg. | % RSD |
| 5 | 14.0% | N/A |
| 10 | 24.9% | N/A |
| 15 | 27.8% | N/A |
| 20 | 28.5% | N/A |
| 30 | 29.1% | N/A |
| 45 | 29.1% | N/A |
| 60 | 29.0% | N/A |
| 75 (Infinity) | 29.5% | N/A |

Example 1

A cabozantinib capsule dosage form was prepared by dissolving butylated hydroxytoluene (BHT) in glyceryl monocaprylate (CAPMUL® MCM C8) and adding polyoxyl 40 stearate (SP MYRJ S40 MBAL-PA-(SG)) into the solution using a water bath (55±5° C.) to obtain a uniform solution. Cabozantinib monolauryl sulfate (non-micronized) was added into the solution to obtain a uniform dispersion or coagulate into a semi-solid. The semi-solid suspension was filled into size 3 hypromellose capsules (HPMC capsule, Vcaps Plus) for 20 mg cabozantinib free base strength.

The composition of the capsule content is as follows:

| Materials | mg | % |
|---|---|---|
| Cabozantinib monolauryl sulfate (CT-LS) | 30.6 | 25.35 |
| Glyceryl Monocaprylate | 30.0 | 24.86 |
| Polyoxyl 40 Stearate | 60.0 | 49.71 |
| Butylated hydroxytoluene (BHT) | 0.1 | 0.08 |
| Total | 120.7 | 100.00 |

Glyceryl monocaprylate (CAPMUL® MCM C8) is reported to have an HLB value of 3.7-5.8.

Polyoxyl 40 stearate (SP MYRJ S40 MBAL-PA-(SG)) is reported to have an HLB value of 16.5-17.5.

The cabozantinib capsule was tested using a U.S.P. Type II (paddle) apparatus with the following conditions:

Condition: 0.01N HCl containing 0.5% TRITON™ X-100, 900 mL, Paddle with Sinker, 75 rpm, 37° C.

| Time | CT210819 | |
|---|---|---|
| (minutes) | Avg. | % RSD |
| 10 | 15.4% | 45.1 |
| 15 | 35.1% | 19.2 |
| 20 | 51.0% | 6.0 |
| 30 | 73.3% | 3.0 |
| 45 | 90.5% | 1.9 |
| 60 | 95.8% | 2.0 |
| 75 (Infinity) | 97.1% | 2.0 |

Condition: pH4.5ABS containing 0.025% TRITON™ X-100, 900 mL, Paddle with Sinker, 75 rpm, 37° C.

| Time | CT210819 | |
|---|---|---|
| (minutes) | Avg. | % RSD |
| 10 | 4.3% | N/A |
| 15 | 15.9% | N/A |
| 20 | 24.3% | N/A |
| 30 | 33.1% | N/A |
| 45 | 39.3% | N/A |
| 60 | 43.2% | N/A |
| 75 (Infinity) | 43.4% | N/A |

Condition: pH4.5 ABS containing 0.2% TRITON™ X-100, 900 mL, Paddle with Sinker, 75 rpm, 37° C.

| Time | CT210819 | |
|---|---|---|
| (minutes) | Avg. | % RSD |
| 10 | 16.0% | N/A |
| 15 | 38.9% | N/A |
| 20 | 53.9% | N/A |
| 30 | 71.9% | N/A |
| 45 | 84.7% | N/A |
| 60 | 91.5% | N/A |
| 75 (Infinity) | 94.3% | N/A |

Condition: pH6.8 PBS, 900 mL, Paddle with Sinker, 75 rpm, 37° C.

| Time | CT210819 | |
|---|---|---|
| (minutes) | Avg. | % RSD |
| 10 | 0.4% | N/A |
| 15 | 5.5% | N/A |
| 20 | 10.2% | N/A |
| 30 | 11.7% | N/A |
| 45 | 13.0% | N/A |
| 60 | 11.7% | N/A |
| 75 (Infinity) | 11.5% | N/A |

Condition: pH6.8 PBS containing 0.025% TRITON™ X-100, 900 mL, Paddle with Sinker, 75 rpm, 37° C.

| Time | CT210819 | |
|---|---|---|
| (minutes) | Avg. | % RSD |
| 10 | 1.2% | N/A |
| 15 | 6.8% | N/A |
| 20 | 11.1% | N/A |
| 30 | 21.6% | N/A |
| 45 | 31.9% | N/A |
| 60 | 36.8% | N/A |
| 75 (Infinity) | 36.2% | N/A |

Condition: pH6.8 PBS containing 0.2% TRITON™ X-100, 900 mL, Paddle with Sinker, 75 rpm, 37° C.

| Time | CT210819 | |
|---|---|---|
| (minutes) | Avg. | % RSD |
| 10 | 3.0% | N/A |
| 15 | 25.8% | N/A |
| 20 | 46.2% | N/A |
| 30 | 57.3% | N/A |
| 45 | 63.9% | N/A |
| 60 | 66.1% | N/A |
| 75 (Infinity) | 68.4% | N/A |

Example 2

A cabozantinib capsule dosage form was prepared by dissolving butylated hydroxytoluene (BHT) in glyceryl monocaprylate (CAPMUL® MCM C8) and adding polyoxyl 40 stearate (SP MYRJ S40 MBAL-PA-(SG)) into the solution using a water bath (55±5° C.) to obtain a uniform solution. Cabozantinib free base (non-micronized) was added into the solution to obtain a uniform dispersion or coagulate into a semi-solid. The semi-solid suspension was filled into size 3 HPMC capsule for 20 mg cabozantinib free base strength.

The composition of the capsule content is as follows:

| Materials | mg | % |
|---|---|---|
| Cabozantinib free base | 20.0 | 18.17 |
| Glyceryl Monocaprylate | 30.0 | 27.25 |
| Polyoxyl 40 Stearate | 60.0 | 54.50 |
| Butylated hydroxytoluene (BHT) | 0.1 | 0.09 |
| Total | 110.1 | 100.00 |

The cabozantinib capsule was tested using a U.S.P. Type II (paddle) apparatus with the following conditions:

Condition: 0.01N HCl containing 0.5% TRITON™ X-100, 900 mL, Paddle with Sinker, 75 rpm, 37° C.

| Time | CT210820A | |
|---|---|---|
| (minutes) | Avg. | % RSD |
| 10 | 23.9% | 30.8 |
| 15 | 46.7% | 20.6 |
| 20 | 60.8% | 8.4 |
| 30 | 77.4% | 5.5 |
| 45 | 92.4% | 4.7 |
| 60 | 95.9% | 3.4 |
| 90 (Infinity) | 97.6% | 1.2 |

Condition: pH4.5 ABS containing 0.025% TRITON™ X-100, 900 mL, Paddle with Sinker, 75 rpm, 37° C.

| Time | CT210820A | |
|---|---|---|
| (minutes) | Avg. | % RSD |
| 10 | 0.7% | N/A |
| 15 | 5.6% | N/A |
| 20 | 7.7% | N/A |
| 30 | 9.0% | N/A |
| 45 | 9.5% | N/A |
| 60 | 9.7% | N/A |
| 75 (Infinity) | 9.7% | N/A |

Condition: pH4.5 ABS containing 0.2% TRITON™ X-100, 900 mL, Paddle with Sinker, 75 rpm, 37° C.

| Time | CT210820A | |
|---|---|---|
| (minutes) | Avg. | % RSD |
| 10 | 1.8% | N/A |
| 15 | 15.6% | N/A |
| 20 | 22.8% | N/A |
| 30 | 29.5% | N/A |
| 45 | 35.5% | N/A |
| 60 | 38.4% | N/A |
| 75 (Infinity) | 39.5% | N/A |

Condition: pH6.8 PBS, 900 mL, Paddle with Sinker, 75 rpm, 37° C.

| Time | CT210820A | |
|---|---|---|
| (minutes) | Avg. | % RSD |
| 10 | 0 | N/A |
| 15 | 0 | N/A |
| 20 | 0 | N/A |
| 30 | 0.5% | N/A |
| 45 | 1.0% | N/A |
| 60 | 0.9% | N/A |
| 75 (Infinity) | 1.1% | N/A |

Condition: pH6.8 PBS containing 0.025% TRITON™ X-100, 900 mL, Paddle with Sinker, 75 rpm, 37° C.

| Time | CT210820A | |
|---|---|---|
| (minutes) | Avg. | % RSD |
| 10 | 0 | N/A |
| 15 | 0 | N/A |
| 20 | 0.4% | N/A |
| 30 | 1.1% | N/A |
| 45 | 2.3% | N/A |

-continued

| Time | CT210820A | |
|---|---|---|
| (minutes) | Avg. | % RSD |
| 60 | 2.7% | N/A |
| 75 (Infinity) | 3.0% | N/A |

Condition: pH6.8 PBS containing 0.2% TRITON™ X-100, 900 mL, Paddle with Sinker, 75 rpm, 37° C.

| Time | CT210820A | |
|---|---|---|
| (minutes) | Avg. | % RSD |
| 10 | 1.5% | N/A |
| 15 | 8.0% | N/A |
| 20 | 14.6% | N/A |
| 30 | 20.9% | N/A |
| 45 | 25.4% | N/A |
| 60 | 26.6% | N/A |
| 75 (Infinity) | 27.3% | N/A |

Example 3

A cabozantinib capsule dosage form was prepared by dissolving butylated hydroxytoluene (BHT) in glyceryl monocaprylate (CAPMUL® MCM C8) and adding polyethylene glycol monostearate into the solution using a water bath (55±5° C.) to obtain a uniform solution. Cabozantinib monolauryl sulfate (micronized) was added into the solution to obtain a uniform dispersion or coagulate into a semi-solid. The semi-solid suspension was filled into size 3 HPMC capsule for 20 mg cabozantinib free base strength.

The composition of the capsule content is as follows:

| Materials | mg | % |
|---|---|---|
| Cabozantinib monolauryl sulfate (CT-LS) | 30.6 | 20.31 |
| Glyceryl Monocaprylate | 40.0 | 26.54 |
| Polyethylene glycol monostearate | 80.0 | 53.09 |
| Butylated hydroxytoluene (BHT) | 0.1 | 0.07 |
| Total | 150.7 | 100.00 |

Polyethylene glycol monostearate is available under the tradename GELUCIRE® 48/16 and is reported to have an HLB value of 12.

The cabozantinib capsule was tested using a U.S.P. Type II (paddle) apparatus with the following conditions:

Condition: 0.01N HCl containing 0.5% TRITON™ X-100, 900 mL, Paddle with Sinker, 75 rpm, 37° C.

| Time | CT2111101 | |
|---|---|---|
| (minutes) | Avg. | % RSD |
| 10 | 1.8% | 125.7 |
| 15 | 11.1% | 129.9 |
| 20 | 22.7% | 96.4 |
| 30 | 41.6% | 55.1 |
| 45 | 61.1% | 31.3 |
| 60 | 72.8% | 22.4 |
| 90 (Infinity) | 101.6% | 2.6 |

Condition: pH4.5 ABS containing 0.2% TRITON™ X-100, 900 mL, Paddle with Sinker, 75 rpm, 37° C.

| Time | CT2111101 | |
|---|---|---|
| (minutes) | Avg. | % RSD |
| 10 | 9.3% | 73.7 |
| 15 | 35.3% | 29.2 |
| 20 | 52.6% | 14.4 |
| 30 | 70.2% | 3.5 |
| 45 | 84.8% | 3.0 |
| 60 | 95.8% | 2.8 |
| 75 (Infinity) | 101.9% | 1.3 |

Example 4

A cabozantinib capsule dosage form was prepared by dissolving butylated hydroxytoluene (BHT) in caprylocaproyl polyoxylglycerides and adding stearoyl polyoxylglycerides into the solution using a water bath (55±5° C.) to obtain a uniform solution. Cabozantinib monolauryl sulfate (micronized) was added into the solution to obtain a uniform dispersion or coagulate into a semi-solid. The semi-solid suspension was filled into size 3 HPMC capsule for 20 mg cabozantinib free base strength.

The composition of the capsule content is as follows:

| Materials | mg | % |
|---|---|---|
| Cabozantinib monolauryl sulfate (CT-LS) | 30.6 | 17.92 |
| Caprylocaproyl Polyoxylglycerides | 30.0 | 17.57 |
| Stearoyl polyoxylglycerides | 110.0 | 64.42 |
| Butylated hydroxytoluene (BHT) | 0.15 | 0.09 |
| Total | 170.75 | 100.00 |

Caprylocaproyl Polyoxylglycerides is available under the tradename LABRASOL® and is reported to have and HLB value of 12.

Stearoyl polyoxylglycerides is available under the tradename GELUCIRE® 50/13 and is reported to have and HLB value of 11.

The cabozantinib capsule was tested using a U.S.P. Type II (paddle) apparatus with the following conditions:

Condition: 0.01N HCl containing 0.5% TRITON™ X-100, 900 mL, Paddle with Sinker, 75 rpm, 37° C.

| Time | CT2110282 | |
|---|---|---|
| (minutes) | Avg. | % RSD |
| 10 | 0.4% | 23.6 |
| 15 | 3.8% | 27.8 |
| 20 | 10.1% | 35.5 |
| 30 | 26.1% | 24.8 |
| 45 | 49.1% | 7.4 |
| 60 | 67.2% | 3.7 |
| 90 (Infinity) | 94.4% | 3.3 |

Condition: pH4.5 ABS containing 0.025% TRITON™ X-100, 900 mL, Paddle with Sinker, 75 rpm, 37° C.

| Time | CT2110282 | |
|---|---|---|
| (minutes) | Avg. | % RSD |
| 10 | 0.1% | N/A |
| 15 | 1.5% | N/A |
| 20 | 6.0% | N/A |

-continued

| Time | CT2110282 | |
|---|---|---|
| (minutes) | Avg. | % RSD |
| 30 | 17.0% | N/A |
| 45 | 32.6% | N/A |
| 60 | 41.9% | N/A |
| 75 (Infinity) | 48.6% | N/A |

Condition: pH4.5 ABS containing 0.2% TRITON™ X-100, 900 mL, Paddle with Sinker, 75 rpm, 37° C.

| Time | CT2110282 | |
|---|---|---|
| (minutes) | Avg. | % RSD |
| 10 | 0.9% | N/A |
| 15 | 3.9% | N/A |
| 20 | 9.1% | N/A |
| 30 | 25.7% | N/A |
| 45 | 51.4% | N/A |
| 60 | 73.5% | N/A |
| 75 (Infinity) | 96.7% | N/A |

Example 5

A cabozantinib capsule dosage form was prepared by melting polyethylene glycol monostearate (GELUCIRE® 48/16) in water bath (55±5° C.) to obtain a solution. Cabozantinib monolauryl sulfate (micronized) was added into the solution to obtain a uniform dispersion or coagulate into a semi-solid. The semi-solid suspension was filled into size 1 hard gelatin capsule for 40 mg cabozantinib free base strength and size 9 hard gelatin capsule for 2 mg and 8 mg cabozantinib free base strengths.

The composition of the capsule content is as follows:

| | Strength (mg of free base) | | | |
|---|---|---|---|---|
| Materials | 40 mg mg | 8 mg mg | 2 mg mg | % |
| Cabozantinib monolauryl sulfate (CT-LS) | 61.2 | 12.24 | 3.06 | 23.43 |
| Polyethylene glycol monostearate | 200.0 | 40.00 | 10.00 | 76.57 |
| | 261.2 | 52.24 | 13.06 | 100.00 |

The 40 mg cabozantinib capsule was tested using a U.S.P. Type II (paddle) apparatus with the following conditions:

Condition: 0.01N HCl with 0.375% TRITON™ X-100, 900 mL, Paddle with stationary basket, 75 rpm, 37° C.

| Time | T220401 | |
|---|---|---|
| (minutes) | Avg. | % RSD |
| 15 | 35.9% | 14.8 |
| 30 | 74.0% | 6.3 |
| 45 | 94.7% | 2.9 |
| 60 | 98.3% | 1.3 |

Example 6

A cabozantinib capsule dosage form was prepared by melting vitamin E polyethylene glycol succinate (Vitamin E TPGS) in a water bath (55±5° C.) to obtain a solution. Cabozantinib monolauryl sulfate (micronized) was added into the solution to obtain a uniform dispersion or coagulate into a semi-solid. The semi-solid suspension was filled into size 1 hard gelatin capsule for 40 mg cabozantinib free base strength and size 9 hard gelatin capsule for 2 mg cabozantinib free base strength.

The composition of the capsule content is as follows:

| | Strength (mg of free base) | | |
|---|---|---|---|
| Materials | 40 mg mg | 2 mg mg | % |
| Cabozantinib monolauryl sulfate (CT-LS) | 61.2 | 3.06 | 23.43 |
| Vitamin E Polyethylene Glycol Succinate | 200.0 | 10.00 | 76.57 |
| Total | 261.2 | 13.06 | 100.00 |

Vitamin E TPGS is reported to have an HLB value of about 13.2.

The 40 mg cabozantinib capsule was tested using a U.S.P. Type II (paddle) apparatus with the following conditions:

Condition: 0.01N HCl with 0.375% TRITON™ X-100, 900 mL, Paddle with stationary basket, 75 rpm, 37° C.

| Time | T220402 | |
|---|---|---|
| (minutes) | Avg. | % RSD |
| 15 | 51.8% | 16.6 |
| 30 | 98.0% | 0.5 |
| 45 | 98.1% | 0.4 |
| 60 | 98.5% | 0.6 |

Example 7

A cabozantinib capsule dosage form was prepared by melting vitamin E polyethylene glycol succinate in a water bath (55±5° C.) to obtain a solution. Cabozantinib (S)-malate (non-micronized) was added into the solution to obtain a uniform dispersion or coagulate into a semi-solid. The semi-solid suspension was filled into size 3 hard gelatin capsule for 20 mg cabozantinib free base strength.

The composition of the capsule content is as follows:

| Materials | mg | % |
|---|---|---|
| Cabozantinib (S)-malate | 25.35 | 20.22 |
| Vitamin E Polyethylene Glycol Succinate | 100.00 | 79.78 |
| Total | 125.35 | 100.00 |

The cabozantinib capsule was tested using a U.S.P. Type II (paddle) apparatus with the following conditions:

Condition: 0.01N HCl with 0.375% TRITON™ X-100, 900 mL, Paddle with stationary basket, 75 rpm, 37° C.

| Time | CT221017 | |
|---|---|---|
| (minutes) | Avg. | % RSD |
| 15 | 77.8% | 15.8 |
| 20 | 97.2% | 3.2 |
| 30 | 98.6% | 2.3 |

-continued

| Time | CT221017 | |
|---|---|---|
| (minutes) | Avg. | % RSD |
| 45 | 100.1% | 2.5 |
| 60 | 99.4% | 2.6 |

Example 8

A cabozantinib capsule dosage form was prepared by adding polyethylene glycol monostearate into polyethylene glycol 400 (PEG 400) and melting using a water bath (55±5° C.) to obtain a uniform solution. Cabozantinib monolauryl sulfate (micronized) was added into the solution to obtain a uniform dispersion or coagulate into a semi-solid. The semi-solid suspension was filled into size 3 hard gelatin capsule for 20 mg cabozantinib free base strength and size 1 hard gelatin capsule for 40 mg cabozantinib free base strength.

The composition of the capsule content is as follows:

| | Strength (mg of free base) | | |
|---|---|---|---|
| Materials | 20 mg mg | 40 mg mg | % |
| Cabozantinib monolauryl sulfate (CT-LS) | 30.6 | 61.2 | 20.32 |
| Polyethylene Glycol 400 | 20.0 | 40.0 | 13.28 |
| Polyethylene glycol monostearate | 100.0 | 200.0 | 66.40 |
| Total | 150.6 | 301.2 | 100.00 |

The cabozantinib capsule was tested using a U.S.P. Type II (paddle) apparatus with the following conditions:

Condition: 0.01N HCl with 0.375% TRITON™ X-100, 900 mL, Paddle with stationary basket, 75 rpm, 37° C.

| Time | CT2203282A 20 mg | | CT2203282B 40 mg | |
|---|---|---|---|---|
| (minutes) | Avg. | % RSD | Avg. | % RSD |
| 15 | 57.0% | 12.3 | 37.7% | 5.9 |
| 20 | 76.4% | 8.2 | 52.1% | 4.2 |
| 30 | 96.3% | 2.5 | 77.1% | 2.5 |
| 60 | 98.1% | 1.2 | 99.0% | 1.5 |

Example 9

A cabozantinib capsule dosage form was prepared by melting polyethylene glycol 1500 (PEG 1500) and polyethylene glycol monostearate in water bath (55±5° C.) to obtain a uniform solution. Cabozantinib monolauryl sulfate (micronized) was added into the solution to obtain a uniform dispersion or coagulate into a semi-solid. The semi-solid suspension was filled into size 3 hard gelatin capsule for 20 mg cabozantinib free base strength.

The composition of the capsule content is as follows:

| Materials | mg | % |
|---|---|---|
| Cabozantinib monolauryl sulfate (CT-LS) | 30.6 | 20.32 |
| Polyethylene glycol monostearate | 60.0 | 39.84 |
| Polyethylene Glycol 1500 | 60.0 | 39.84 |
| Total | 150.6 | 100.00 |

The cabozantinib capsule was tested using a U.S.P. Type II (paddle) apparatus with the following conditions:

Condition: 0.01N HCl with 0.375% TRITON™ X-100, 900 mL, Paddle with stationary basket, 75 rpm, 37° C.

| Time | CT2203172 | |
|---|---|---|
| (minutes) | Avg. | % RSD |
| 15 | 76.3% | 9.1 |
| 20 | 92.8% | 3.5 |
| 30 | 97.3% | 1.3 |
| 60 | 98.2% | 1.5 |

Condition: pH4.5 ABS containing 0.2% TRITON™ X-100, 900 mL, Paddle with stationary basket, 75 rpm, 37° C.

| Time | CT2203172 | |
|---|---|---|
| (minutes) | Avg. | % RSD |
| 15 | 56.3% | 22.7 |
| 20 | 84.1% | 10.1 |
| 30 | 99.5% | 2.0 |
| 60 | 99.3% | 2.0 |

Example 10

A cabozantinib capsule dosage form was prepared by melting poloxamer 188 in water bath (55±5° C.) to obtain a solution. Cabozantinib monolauryl sulfate (micronized) was added into the solution to obtain a uniform dispersion or coagulate into a semi-solid. The semi-solid suspension was filled into size 3 hard gelatin capsule for 20 mg cabozantinib free base strength.

The composition of the capsule content is as follows:

| Materials | mg | % |
|---|---|---|
| Cabozantinib monolauryl sulfate (CT-LS) | 30.6 | 23.43 |
| Poloxamer 188 | 100.0 | 76.57 |
| Total | 130.6 | 100.00 |

Poloxamer 188 is reported to have an HLB value of about 29.

The cabozantinib capsule was tested using a U.S.P. Type II (paddle) apparatus with the following conditions:

Condition: 0.01N HCl with 0.375% TRITON™ X-100, 900 mL, Paddle with stationary basket, 75 rpm, 37° C.

| Time | CT220610A | |
|---|---|---|
| (minutes) | Avg. | % RSD |
| 15 | 70.1% | 9.8 |
| 20 | 90.9% | 7.3 |
| 30 | 100.5% | 3.3 |
| 45 | 100.5% | 2.9 |
| 60 | 100.2% | 2.8 |

Example 11

A cabozantinib capsule dosage form was prepared by melting polyoxyl 40 hydrogenated castor oil in a water bath (55±5° C.) to obtain a solution. Cabozantinib monolauryl sulfate (micronized) was added into the solution to obtain a uniform dispersion or coagulate into a semi-solid. The semi-solid suspension was filled into size 3 hard gelatin capsule for 20 mg cabozantinib free base strength.

The composition of the capsule content is as follows:

| Materials | mg | % |
|---|---|---|
| Cabozantinib monolauryl sulfate (CT-LS) | 30.6 | 23.43 |
| Polyoxyl 40 hydrogenated castor oil | 100.0 | 76.57 |
| Total | 130.6 | 100.00 |

Polyoxyl 40 hydrogenated castor oil (KOLLIPHOR® RH 40) is reported to have an HLB value of 14-16.

The cabozantinib capsule was tested using a U.S.P. Type II (paddle) apparatus with the following conditions:

Condition: 0.01N HCl with 0.375% TRITON™ X-100, 900 mL, Paddle with stationary basket, 75 rpm, 37° C.

| Time | CT220607A | |
|---|---|---|
| (minutes) | Avg. | % RSD |
| 15 | 74.3% | 18.3 |
| 20 | 95.5% | 3.2 |
| 30 | 98.7% | 1.9 |
| 45 | 99.1% | 2.1 |
| 60 | 99.1% | 2.8 |

Example 12

A cabozantinib capsule dosage form was prepared by melting polyethylene glycol monostearate in a water bath (55±5° C.) to obtain a solution. Cabozantinib monolauryl sulfate (micronized) was added into the solution to obtain a uniform dispersion or coagulate into a semi-solid. The semi-solid suspension was filled into size 3 hard gelatin capsule for 14 mg cabozantinib free base strength.

The composition of the capsule content is as follows:

| Materials | mg | % |
|---|---|---|
| Cabozantinib monolauryl sulfate (CT-LS) | 21.4 | 17.63 |
| Polyethylene glycol monostearate | 100.0 | 82.37 |
| Total | 121.4 | 100.00 |

The cabozantinib capsule was tested using a U.S.P. Type II (paddle) apparatus with the following conditions:

Condition: 0.01N HCl with 0.375% TRITON™ X-100, 900 mL, Paddle with stationary basket, 75 rpm, 37° C.

| Time | CT220301A | |
|---|---|---|
| (minutes) | Avg. | % RSD |
| 15 | 62.5% | 14.3 |
| 20 | 85.2% | 7.4 |
| 30 | 97.4% | 2.0 |
| 60 | 97.9% | 2.1 |

Condition: 0.01N HCl with 0.5% TRITON™ X-100, 900 mL, Paddle with stationary basket, 75 rpm, 37° C.

| Time | CT220301A | |
|---|---|---|
| (minutes) | Avg. | % RSD |
| 15 | 59.8% | 11.9 |
| 20 | 81.6% | 7.6 |
| 30 | 97.1% | 2.1 |
| 60 | 98.0% | 1.8 |

Condition: 0.01N HCl with 0.5% TRITON™ X-100, 900 mL, Paddle with sinker, 75 rpm, 37° C.

| Time | CT220301A | |
|---|---|---|
| (minutes) | Avg. | % RSD |
| 15 | 59.3% | 30.0 |
| 20 | 75.7% | 24.4 |
| 30 | 91.8% | 13.0 |
| 60 | 99.8% | 1.8 |

Condition: pH4.5 ABS containing 0.2% TRITON™ X-100, 900 mL, Paddle with sinker, 75 rpm, 37° C.

| Time | CT220301A | |
|---|---|---|
| (minutes) | Avg. | % RSD |
| 15 | 31.0% | 67.7 |
| 20 | 54.3% | 41.7 |
| 30 | 80.8% | 17.9 |
| 60 | 99.5% | 2.9 |

Condition: 25 mM pH4.5 ABS containing 0.5% TRITON™ X-100, 900 mL, Paddle with sinker, 75 rpm, 37° C.

| Time | CT220301A | |
|---|---|---|
| (minutes) | Avg. | % RSD |
| 15 | 55.4% | 35.0 |
| 20 | 74.8% | 18.4 |
| 30 | 90.9% | 7.6 |
| 60 | 98.1% | 2.4 |

Condition: 25 mM pH4.5 ABS containing 0.2% TRITON™ X-100, 900 mL, Paddle with stationary basket, 75 rpm, 37° C.

| Time | CT220301A | |
|---|---|---|
| (minutes) | Avg. | % RSD |
| 15 | 48.8% | 14.4 |
| 20 | 79.2% | 9.3 |
| 30 | 97.8% | 2.2 |
| 60 | 99.1% | 2.0 |

Condition: 25 mM pH4.5 ABS containing 0.5% TRITON™ X-100, 900 mL, Paddle with stationary basket, 75 rpm, 37° C.

| Time | CT220301A | |
|---|---|---|
| (minutes) | Avg. | % RSD |
| 15 | 52.9% | 22.7 |
| 20 | 80.1% | 6.6 |
| 30 | 96.8% | 2.0 |
| 60 | 97.4% | 1.7 |

Condition: 50 mM pH4.5 ABS containing 0.2% TRITON™ X-100, 900 mL, Paddle with stationary basket, 75 rpm, 37° C.

| Time | CT220301A | |
|---|---|---|
| (minutes) | Avg. | % RSD |
| 15 | 52.6% | 18.0 |
| 20 | 83.5% | 5.4 |
| 30 | 96.3% | 1.3 |
| 60 | 96.6% | 2.9 |

Condition: 50 mM pH4.5 ABS containing 0.5% TRITON™ X-100, 900 mL, Paddle with stationary basket, 75 rpm, 37° C.

| Time | CT220301A | |
|---|---|---|
| (minutes) | Avg. | % RSD |
| 15 | 46.8% | 20.3 |
| 20 | 76.4% | 9.4 |
| 30 | 96.8% | 2.2 |
| 60 | 98.5% | 2.7 |

Condition: 50 mM pH 4.5 ABS containing 0.2% TRITON™ X-100, 900 mL, Paddle with stationary basket, 50 rpm, 37° C.

| Time | CT220301A | |
|---|---|---|
| (minutes) | Avg. | % RSD |
| 15 | 27.3% | 22.9 |
| 20 | 55.2% | 14.1 |
| 30 | 89.7% | 7.1 |
| 60 | 100.3% | 3.3 |

Example 13

A cabozantinib capsule dosage form was prepared by melting polyethylene glycol monostearate in water bath (55±5° C.) to obtain a solution. Cabozantinib monolauryl sulfate (micronized) was added into the solution to obtain a uniform dispersion or coagulate into a semi-solid. The semi-solid was milled after cooling and filled into size 3 hard gelatin capsule for 14 mg cabozantinib free base strength.

The composition of the capsule content is as follows:

| Materials | mg | % |
|---|---|---|
| Cabozantinib monolauryl sulfate (CT-LS) | 21.4 | 17.63 |
| Polyethylene glycol monostearate | 100.0 | 82.37 |
| Total | 121.4 | 100.00 |

The cabozantinib capsule was tested using a U.S.P. Type II (paddle) apparatus with the following conditions:

Condition: 0.01N HCl with 0.5% TRITON™ X-100, 900 mL, Paddle with sinker, 75 rpm, 37° C.

| Time | CT220221A | |
|---|---|---|
| (minutes) | Avg. | % RSD |
| 15 | 79.2% | 17.1 |
| 20 | 92.7% | 11.4 |
| 30 | 100.0% | 3.8 |
| 60 | 102.5% | 1.0 |

Condition: pH4.5 ABS containing 0.2% TRITON™ X-100, 900 mL, Paddle with sinker, 75 rpm, 37° C.

| Time | CT220221A | |
|---|---|---|
| (minutes) | Avg. | % RSD |
| 15 | 91.4% | 7.8 |
| 20 | 98.5% | 3.2 |
| 30 | 100.1% | 2.6 |
| 60 | 100.5% | 2.6 |

Example 14

A cabozantinib capsule dosage form was prepared by melting polyethylene glycol monostearate in a water bath (55±5° C.) to obtain a solution. Cabozantinib monolauryl sulfate (micronized) was added into the solution to obtain a uniform dispersion or coagulate into a semi-solid. The semi-solid was milled after cooling, and mixed with extra-granular excipients after screening through 30 mesh screen. The mixture was filled into size 3 hard gelatin capsule for 14 mg cabozantinib free base strength.

The composition of the capsule content is as follows:

| Materials | mg | % |
|---|---|---|
| Cabozantinib monolauryl sulfate (CT-LS) | 21.4 | 8.56 |
| Polyethylene glycol monostearate | 100.0 | 40.00 |
| Microcrystalline cellulose | 83.6 | 33.44 |
| Croscarmellose sodium | 17.5 | 7.00 |
| Colloidal silicon dioxide | 25.0 | 10.00 |
| Sodium stearyl fumarate | 2.5 | 1.00 |
| Total | 250.0 | 100.00 |

The cabozantinib capsule was tested using a U.S.P. Type II (paddle) apparatus with the following conditions:

Condition: 0.01N HCl with 0.5% TRITON™ X-100, 900 mL, Paddle with sinker, 75 rpm, 37° C.

| Time | CT220301D | |
|---|---|---|
| (minutes) | Avg. | % RSD |
| 15 | 98.2% | 4.0 |
| 20 | 100.6% | 2.6 |
| 30 | 101.5% | 2.4 |
| 60 | 102.3% | 2.6 |

Condition: pH4.5 ABS containing 0.2% TRITON™ X-100, 900 mL, Paddle with sinker, 75 rpm, 37° C.

| Time | CT220301D | |
|---|---|---|
| (minutes) | Avg. | % RSD |
| 15 | 89.6% | 4.0 |
| 20 | 97.1% | 4.3 |
| 30 | 98.5% | 4.8 |
| 60 | 98.3% | 4.0 |

Example 15

A cabozantinib capsule dosage form was prepared by melting polyethylene glycol monostearate in a water bath (55±5° C.) to obtain a solution. Cabozantinib monolauryl sulfate (micronized) was added into the solution to obtain a uniform dispersion or coagulate into a semi-solid. The semi-solid suspension was filled into size 9 hard gelatin capsule for 0.6 mg, 1.2 mg, 1.6 mg, 2.4 mg and 4.8 mg cabozantinib free base strengths.

The compositions of the capsule content are as follows:

| | Strength (mg of free base) | | | | | |
|---|---|---|---|---|---|---|
| Materials | 0.6 mg mg | 1.2 mg mg | 1.6 mg mg | 2.4 mg mg | 4.8 mg mg | % |
| Cabozantinib monolauryl sulfate (CT-LS) | 0.92 | 1.84 | 2.45 | 3.67 | 7.34 | 23.43 |
| Polyethylene glycol monostearate | 3.00 | 6.00 | 8.00 | 12.00 | 24.00 | 76.57 |
| Total | 3.92 | 7.84 | 10.45 | 15.67 | 31.34 | 100.00 |

Example 16

A cabozantinib capsule dosage form was prepared by melting vitamin E polyethylene glycol succinate in a water bath (55±5° C.) to obtain a solution. Cabozantinib monolauryl sulfate (micronized) was added into the solution to obtain a uniform dispersion or coagulate into a semi-solid. The semi-solid suspension was filled into size 9 hard gelatin capsule for 0.6 mg, 1.2 mg, 2.4 mg and 4.8 mg cabozantinib free base strengths.

The compositions of the capsule content are as follows:

| | Strength (mg of free base) | | | | |
|---|---|---|---|---|---|
| Materials | 0.6 mg mg | 1.2 mg mg | 2.4 mg mg | 4.8 mg mg | % |
| Cabozantinib monolauryl sulfate (CT-LS) | 0.92 | 1.84 | 3.67 | 7.34 | 23.43 |
| Vitamin E Polyethylene Glycol Succinate | 3.00 | 6.00 | 12.00 | 24.00 | 76.57 |
| Total | 3.92 | 7.84 | 15.67 | 31.34 | 100.00 |

Example 17

The capsule prepared in Example 1 (Test 1) containing cabozantinib monolauryl sulfate (equivalent to 20 mg of cabozantinib free base) and capsule prepared in Example 2 (Test 2) containing cabozantinib free base were administered to six (6) healthy adult beagle dogs in a fasted state along with an equivalent 20 mg cabozantinib malate tablet prepared in Comparative Example 1 (Ref) in a single-center, single-dose study with a washout period of 7 days between the periods. Blood samples were drawn before dosing and at 0 (prior to the dosing), 0.5, 1, 1.5, 2, 3, 4, 6, 8, 12, 16 and 24 hours after dosing. The six (6) healthy adult beagle dogs enrolled in this study were randomized to one of the sequences as shown in the following table.

| Sequence | Period I | Period II | Period III |
|---|---|---|---|
| 1 | Ref | Test 1 | Test 2 |
| 2 | Test 1 | Test 2 | Ref |
| 3 | Test 2 | Ref | Test 1 |

The results were summarized in the following tables:

The Pharmacokinetic Parameters for Reference and Test Formulations

| Treatment | Parameters | Geometric Mean |
|---|---|---|
| Tablet prepared according | $C_{max}$ (ng/ml) | 458.09 |
| to Comparative Example 1 | $AUC_{0-24}$ (ng · h/mL) | 2171.49 |
| Ref $_{Fasted}$ | $AUC_{0-\infty}$ (ng · h/mL) | 2646.22 |
| Capsule prepared | $C_{max}$ (ng/ml) | 457.85 |
| according to Example 1 | $AUC_{0-24}$ (ng · h/mL) | 2630.49 |
| Test $1_{Fasted}$ | $AUC_{0-\infty}$ (ng · h/mL) | 3130.01 |
| Capsule prepared | $C_{max}$ (ng/ml) | 48.41 |
| according to Example 2 | $AUC_{0-24}$ (ng · h/mL) | 282.51 |
| Test $2_{Fasted}$ | $AUC_{0-\infty}$ (ng · h/mL) | 182.75 |

Ln-transformed $AUC_{0-t}$, $AUC_{0-\infty}$ and $C_{max}$ were analyzed by FDA certified pharmacokinetic program Phoenix WinNonlin 7.0 (Pharsight, USA). A comparison of the data obtained from the Test and Ref dosing is shown in the following table:

The Comparisons between Test 1 vs. Ref and Test 2 vs. Ref

| Comparisons | Parameters | Geometric Mean Ratios |
|---|---|---|
| Test 1~Ref | $C_{max}$ (ng/ml) | 99.95% |
| (Fasted) | $AUC_{0-24}$ (ng · h/mL) | 121.14% |
| | $AUC_{0-\infty}$ (ng · h/mL) | 118.28% |
| Test 2~Ref | $C_{max}$ (ng/ml) | 10.57% |
| (Fasted) | $AUC_{0-24}$ (ng · h/mL) | 13.01% |
| | $AUC_{0-\infty}$ (ng · h/mL) | 7.16% |

The individual subject data obtained from the study is as follows:

Reference Drug under fasted condition (Concentration (ng/mL))

| Time | Subject | | | | | | | |
|---|---|---|---|---|---|---|---|---|
| (hr) | 1 | 2 | 3 | 4 | 5 | 6 | Mean | SD |
| 0 | BLQ | BLQ | BLQ | BLQ | BLQ | BLQ | NA | NA |
| 0.5 | BLQ | BLQ | BLQ | 209.54 | 58.16 | 404.04 | 223.91 | 173.39 |
| 1 | BLQ | 507.44 | BLQ | 436.53 | 78.62 | 584.90 | 401.87 | 223.86 |
| 1.5 | 32.85 | 836.84 | 43.77 | 322.14 | 77.33 | 496.74 | 301.61 | 320.62 |
| 2 | 613.37 | 590.71 | 794.61 | 284.35 | 88.73 | 393.40 | 460.86 | 255.22 |
| 3 | 396.90 | 484.56 | 638.47 | 261.89 | 60.60 | 302.47 | 357.48 | 198.48 |
| 4 | 314.39 | 378.89 | 595.45 | 225.04 | 67.35 | 218.32 | 299.91 | 178.96 |
| 6 | 98.61 | 187.57 | 242.52 | 81.79 | 32.99 | 66.02 | 118.25 | 79.95 |
| 8 | 74.63 | 141.04 | 183.37 | 53.10 | 18.52 | 48.95 | 86.60 | 62.68 |
| 12 | 41.23 | 98.84 | 109.53 | 32.58 | 13.38 | 29.82 | 54.23 | 39.88 |
| 16 | 23.44 | 64.08 | 80.72 | 18.90 | 9.40 | 67.65 | 44.03 | 30.20 |
| 24 | 22.08 | 87.61 | 60.21 | 10.61 | 20.72 | BLQ | 40.25 | 32.53 |

Test Drug 1 under fasted condition (Concentration (ng/mL))

| Time | Subject | | | | | | | |
|---|---|---|---|---|---|---|---|---|
| (hr) | 1 | 2 | 3 | 4 | 5 | 6 | Mean | SD |
| 0 | BLQ | BLQ | BLQ | BLQ | BLQ | BLQ | NA | NA |
| 0.5 | 580.03 | 349.39 | BLQ | 362.89 | 120.14 | 73.67 | 297.22 | 205.15 |
| 1 | 556.26 | 808.51 | 8.31 | 299.69 | 571.60 | 479.37 | 453.96 | 273.15 |
| 1.5 | 450.86 | 745.44 | 50.44 | 273.64 | 563.44 | 496.19 | 430.00 | 241.10 |
| 2 | 470.42 | 564.56 | 188.58 | 235.50 | 520.35 | 502.17 | 413.60 | 159.76 |
| 3 | 467.23 | 340.06 | 171.67 | 274.19 | 396.77 | 302.98 | 325.48 | 102.16 |
| 4 | 492.09 | 514.75 | 149.33 | 280.76 | 368.40 | 218.81 | 337.35 | 147.64 |
| 6 | 137.93 | 146.08 | 77.67 | 91.18 | 209.74 | 71.44 | 122.34 | 52.92 |
| 8 | 84.55 | 133.42 | 53.17 | 58.21 | 150.37 | 59.23 | 89.83 | 42.13 |
| 12 | 52.68 | 78.98 | 29.33 | 32.67 | 77.91 | 35.28 | 51.14 | 22.64 |
| 16 | 32.16 | 61.51 | 50.06 | 20.70 | 50.40 | 21.26 | 39.35 | 17.06 |
| 24 | 15.41 | 58.11 | 52.68 | 23.10 | 26.99 | 19.38 | 32.61 | 18.14 |

Test Drug 2 under fasted condition (Concentration (ng/mL))

| Time | Subject | | | | | | | |
|---|---|---|---|---|---|---|---|---|
| (hr) | 1 | 2 | 3 | 4 | 5 | 6 | Mean | SD |
| 0 | BLQ | BLQ | BLQ | BLQ | BLQ | BLQ | NA | NA |
| 0.5 | BLQ | BLQ | BLQ | BLQ | 37.84 | 18.26 | 28.05 | 13.85 |
| 1 | 6.27 | 58.33 | BLQ | 12.01 | 28.86 | 9.74 | 23.04 | 21.56 |
| 1.5 | 16.31 | 65.90 | 11.49 | 17.35 | 24.09 | 15.39 | 25.09 | 20.41 |
| 2 | 22.64 | 45.06 | 25.45 | 18.61 | 20.79 | 12.55 | 24.18 | 11.11 |
| 3 | 20.62 | 40.04 | 40.32 | 15.04 | 18.44 | 11.48 | 24.32 | 12.67 |
| 4 | 19.46 | 38.37 | 30.74 | 17.75 | 20.82 | 8.90 | 22.67 | 10.38 |
| 6 | 6.94 | 15.52 | 10.40 | 3.73 | 8.19 | 2.64 | 7.90 | 4.70 |
| 8 | 5.32 | 10.29 | 7.87 | 3.77 | 5.51 | 2.51 | 5.88 | 2.82 |
| 12 | 3.05 | 7.69 | 4.64 | BLQ | 2.16 | 1.91 | 3.89 | 2.38 |
| 16 | BLQ | 6.39 | 102.69 | BLQ | BLQ | BLQ | 54.54 | 68.09 |
| 24 | BLQ | 3.71 | 164.91 | 75.72 | 2.20 | BLQ | 61.64 | 76.93 |

A graph of the mean plasma profiles for this study is shown in FIG. 1.

Example 18

The capsules prepared in Example 3 (Test 1) and Example 4 (Test 2) containing cabozantinib monolauryl sulfate (equivalent to 20 mg of cabozantinib free base) were administered to six (6) healthy adult beagle dogs in a fasted state along with an equivalent 20 mg cabozantinib malate tablet prepared in Comparative Example 1 (Ref) in a single-center, single-dose study with a washout period of 7 days between the periods. Blood samples were drawn before dosing and at 0 (prior to the dosing), 0.5, 1, 1.5, 2, 3, 4, 6, 8, 12, 16 and 24 hours after dosing.

The six (6) healthy adult beagle dogs enrolled in this study were randomized to one of the sequences as shown in the following table.

| Sequence | Period I | Period II | Period III |
|---|---|---|---|
| 1 | Ref | Test 1 | Test 2 |
| 2 | Test 1 | Test 2 | Ref |
| 3 | Test 2 | Ref | Test 1 |

The results were summarized in the following tables:

The Pharmacokinetic Parameters for Reference and Test Formulations

| Treatment | Parameters | Geometric Mean |
|---|---|---|
| Tablet prepared according | $C_{max}$ (ng/ml) | 1339.30 |
| to Comparative Example 1 | $AUC_{0-24}$ (ng · h/mL) | 5847.08 |
| Ref $_{Fasted}$ | $AUC_{0-\infty}$ (ng · h/mL) | 5961.14 |
| Capsule prepared | $C_{max}$ (ng/ml) | 2178.77 |
| according to Example 3 | $AUC_{0-24}$ (ng · h/mL) | 8010.68 |
| Test $1_{Fasted}$ | $AUC_{0-\infty}$ (ng · h/mL) | 8388.11 |

-continued

The Pharmacokinetic Parameters for Reference and Test Formulations

| Treatment | Parameters | Geometric Mean |
|---|---|---|
| Capsule prepared | $C_{max}$ (ng/ml) | 2194.76 |
| according to Example 4 | $AUC_{0-24}$ (ng · h/mL) | 7553.46 |
| Test $2_{Fasted}$ | $AUC_{0-\infty}$ (ng · h/mL) | 7764.64 |

Ln-transformed $AUC_{0-t}$, $AUC_{0-\infty}$, and $C_{max}$ were analyzed by FDA certified pharmacokinetic program Phoenix WinNonlin 7.0 (Pharsight, USA). A comparison of the data obtained from the Test and Ref dosing is shown in the following table:

The Comparisons between Test 1 vs. Ref and Test 2 vs. Ref

The Comparisons between Test 1 vs. Ref and Test 2 vs. Ref

| Comparisons | Parameters | Geometric Mean Ratios |
|---|---|---|
| Test 1~Ref | $C_{max}$ (ng/ml) | 162.68% |
| (Fasted) | $AUC_{0-24}$ (ng · h/mL) | 137.00% |
| | $AUC_{0-\infty}$ (ng · h/mL) | 145.21% |
| Test 2~Ref | $C_{max}$ (ng/ml) | 163.87% |
| (Fasted) | $AUC_{0-24}$ (ng · h/mL) | 129.18% |
| | $AUC_{0-\infty}$ (ng · h/mL) | 124.47% |

The individual subject data obtained from the study is as follows:

Reference Drug under fasted condition (Concentration (ng/mL))

| | Subject | | | | | | | |
|---|---|---|---|---|---|---|---|---|
| Time | 1 | 2 | 3 | 4 | 5 | 6 | Mean | SD |
| 0 | BLQ | BLQ | BLQ | BLQ | BLQ | BLQ | NA | NA |
| 0.5 | 840.66 | 885.80 | 133.08 | 439.52 | 664.95 | 947.16 | 651.86 | 313.68 |
| 1 | 1791.14 | 2165.69 | 1115.94 | 2116.82 | 640.62 | 779.15 | 1434.89 | 676.55 |
| 1.5 | 1710.83 | 2165.60 | 997.42 | 2084.28 | 556.89 | 612.89 | 1354.65 | 725.41 |
| 2 | 1263.85 | 2026.06 | 742.52 | 1832.66 | 486.28 | 489.64 | 1140.17 | 676.54 |
| 3 | 1421.43 | 1500.27 | 552.44 | 1348.85 | 468.58 | 392.88 | 947.41 | 526.17 |
| 4 | 845.96 | 1121.94 | 439.21 | 766.19 | 297.41 | 293.22 | 627.32 | 336.92 |
| 6 | 417.68 | 353.96 | 125.79 | 228.50 | 141.49 | 100.12 | 227.92 | 131.25 |
| 8 | 163.32 | 176.78 | 85.46 | 101.57 | 84.02 | 63.55 | 112.45 | 46.41 |
| 12 | 65.99 | 93.05 | 33.03 | 30.72 | 65.82 | 56.72 | 57.55 | 23.33 |
| 16 | 34.47 | 52.04 | 16.60 | 83.92 | 351.67 | 37.39 | 96.01 | 127.26 |
| 24 | 56.87 | 53.71 | 5.10 | 14.19 | 205.88 | 11.55 | 57.88 | 75.85 |

Test Drug 1 under fasted condition (Concentration (ng/mL))

| | Subject | | | | | | | |
|---|---|---|---|---|---|---|---|---|
| Time | 1 | 2 | 3 | 4 | 5 | 6 | Mean | SD |
| 0 | BLQ | BLQ | BLQ | BLQ | BLQ | BLQ | NA | NA |
| 0.5 | 1605.06 | 515.47 | 678.02 | 1679.03 | 1585.70 | 927.78 | 1165.17 | 519.65 |
| 1 | 2595.85 | 2597.73 | 1922.85 | 2466.99 | 1240.96 | 2108.90 | 2155.55 | 525.20 |
| 1.5 | 1915.11 | 2354.92 | 1510.92 | 2067.70 | 1119.41 | 1363.32 | 1721.90 | 467.70 |
| 2 | 1799.69 | 2420.69 | 1110.90 | 1874.11 | 983.06 | 1274.75 | 1577.20 | 549.74 |
| 3 | 1238.89 | 1816.69 | 805.06 | 1048.55 | 890.66 | 749.43 | 1091.55 | 397.21 |
| 4 | 1077.28 | 1154.26 | 548.81 | 970.23 | 864.53 | 702.19 | 886.22 | 229.60 |
| 6 | 275.94 | 361.75 | 182.43 | 302.35 | 675.02 | 210.47 | 334.66 | 178.70 |
| 8 | 186.00 | 219.99 | 103.91 | 149.88 | 267.90 | 135.02 | 177.12 | 60.05 |
| 12 | 90.54 | 106.57 | 52.23 | 56.35 | 186.26 | 59.65 | 91.93 | 50.99 |
| 16 | 66.26 | 59.99 | 38.98 | 31.07 | 122.37 | 33.64 | 58.72 | 34.33 |
| 24 | 48.16 | 34.29 | 18.00 | 50.09 | 58.28 | 11.16 | 36.66 | 18.89 |

Test Drug 2 under fasted condition (Concentration (ng/mL))

| | Subject | | | | | | | |
|---|---|---|---|---|---|---|---|---|
| Time | 1 | 2 | 3 | 4 | 5 | 6 | Mean | SD |
| 0 | BLQ | BLQ | BLQ | BLQ | BLQ | BLQ | NA | NA |
| 0.5 | 12.17 | 8.50 | BLQ | BLQ | 1345.68 | 971.83 | 584.55 | 680.38 |
| 1 | 2111.78 | 762.14 | 1713.30 | 369.73 | 3369.80 | 1706.03 | 1672.13 | 1058.54 |
| 1.5 | 1438.70 | 2695.84 | 1611.17 | 1993.24 | 2915.66 | 1470.95 | 2020.93 | 642.84 |
| 2 | 1184.75 | 2440.08 | 1157.68 | 1803.20 | 2519.39 | 1143.12 | 1708.04 | 647.93 |
| 3 | 1125.02 | 1359.45 | 714.56 | 1191.92 | 1813.34 | 873.38 | 1179.61 | 386.56 |
| 4 | 965.27 | 1565.79 | 457.26 | 1027.04 | 1524.69 | 642.72 | 1030.46 | 450.33 |
| 6 | 266.15 | 374.83 | 156.73 | 243.67 | 690.12 | 254.99 | 331.08 | 189.14 |
| 8 | 156.49 | 232.18 | 79.22 | 115.88 | 408.82 | 152.94 | 190.92 | 118.25 |

-continued

| | Subject | | | | | | | |
|---|---|---|---|---|---|---|---|---|
| Time | 1 | 2 | 3 | 4 | 5 | 6 | Mean | SD |
| 12 | 59.95 | 164.04 | 37.60 | 38.16 | 180.54 | 63.09 | 90.56 | 64.40 |
| 16 | 34.48 | 58.00 | 18.23 | 15.24 | 121.82 | 30.76 | 46.42 | 39.94 |
| 24 | 21.54 | 33.22 | 6.71 | 52.75 | 94.69 | 17.29 | 37.70 | 32.04 |

Figure 2:
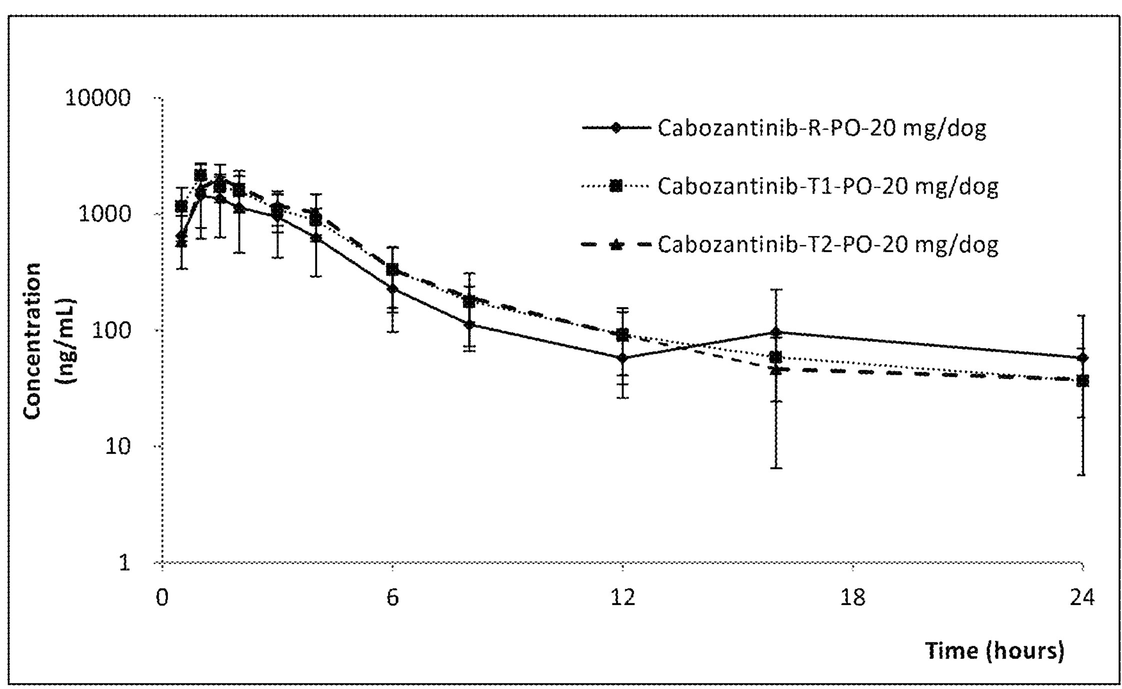
FIG. 2 is a graph of the mean in vivo plasma data provided in Example 18.

A graph of the mean plasma profiles for this study is shown in FIG. 2.

Example 19

The capsules prepared in Example 5 (Test 1) and Example 6 (Test 2) containing cabozantinib monolauryl sulfate (equivalent to 2 mg of cabozantinib free base) were administered to eighteen (18) Wistar rats under a fasted state along with an equivalent 2 mg capsule prepared from CABOMETYX® tablets (obtained by crushing the commercially available 60 mg CABOMETYX® tablets containing 76.05 mg cabozantinib (S)-malate and refilling into new capsules in which each content is equivalent to 2 mg of cabozantinib free base) (Ref) in a single-center, single-dose study. Blood samples were drawn before dosing and at 0.5, 1, 2, 3, 4, 5, 6, 8 and 24 hours after dosing.

The eighteen (18) Wistar rats in this study were randomized to one of the sequences as shown in the following table.

| Sequence | Period I |
|---|---|
| 1 | Ref |
| 2 | Test 1 |
| 3 | Test 2 |

The results were summarized in the following tables:

| The Pharmacokinetic Parameters for Reference and Test Formulations (Equivalent to 2 mg dose) | | |
|---|---|---|
| Treatment | Parameters | Geometric Mean |
| Ref $_{Fasted}$ | $C_{max}$ (ng/ml) | 6316.44 |
| | $AUC_{0-24}$ (ng · h/mL) | 72279.41 |
| | $AUC_{0-\infty}$ (ng · h/mL) | 91010.86 |

-continued

| The Pharmacokinetic Parameters for Reference and Test Formulations (Equivalent to 2 mg dose) | | |
|---|---|---|
| Treatment | Parameters | Geometric Mean |
| Test $1_{Fasted}$ | $C_{max}$ (ng/mL) | 13203.56 |
| | $AUC_{0-24}$ (ng · h/mL) | 112008.85 |
| | $AUC_{0-\infty}$ (ng · h/mL) | 145924.62 |
| Test $2_{Fasted}$ | $C_{max}$ (ng/mL) | 13933.48 |
| | $AUC_{0-24}$ (ng · h/mL) | 119168.13 |
| | $AUC_{0-\infty}$ (ng · h/mL) | 159251.22 |

Ln-transformed $AUC_{0-t}$, $AUC_{0-\infty}$ and $C_{max}$ were analyzed by FDA certified pharmacokinetic program Phoenix WinNonlin 7.0 (Pharsight, USA). A comparison of the data obtained from the Test and Ref dosing is shown in the following table:

| The Comparisons between Test 1 vs. Ref and Test 2 vs. Ref (Equivalent to 2 mg dose) | | |
|---|---|---|
| Comparisons | Parameters | Geometric Mean Ratios |
| Test 1~Ref | $C_{max}$ (ng/ml) | 209.03% |
| (Fasted) | $AUC_{0-24}$ (ng · h/mL) | 154.97% |
| | $AUC_{0-\infty}$ (ng · h/mL) | 160.34% |
| Test 2~Ref | $C_{max}$ (ng/ml) | 220.59% |
| (Fasted) | $AUC_{0-24}$ (ng · h/mL) | 164.87% |
| | $AUC_{0-\infty}$ (ng · h/mL) | 174.98% |

The individual subject data obtained from the study is as follows:

Reference Drug under fasted condition (Concentration (ng/mL))

| | Subject | | | | | | | | |
|---|---|---|---|---|---|---|---|---|---|
| Time | 1 | 2 | 3 | 4 | 5 | 6 | Mean | SD | CV % |
| 0.5 | 128.19 | 145.85 | 6.21 | 4586.00 | 358.61 | BLQ | 1044.97 | 1983.55 | 189.82 |
| 1 | 943.49 | 1526.37 | 31.32 | 7144.82 | 2578.88 | 22.23 | 2041.19 | 2680.37 | 131.31 |
| 2 | 1410.68 | 3068.36 | 107.70 | 9335.73 | 4383.59 | 105.27 | 3068.55 | 3501.52 | 114.11 |
| 3 | 1912.48 | 7075.80 | 656.37 | 8360.98 | 5770.12 | 302.39 | 4013.02 | 3487.72 | 86.91 |
| 4 | 5660.04 | 6925.32 | 1303.28 | 7609.26 | 6345.52 | 759.81 | 4767.21 | 2969.21 | 62.28 |
| 5 | 4027.35 | 4285.76 | 4633.78 | 3054.14 | 4257.33 | 678.57 | 3489.49 | 1477.37 | 42.34 |
| 6 | 3874.66 | 4507.93 | 5136.12 | 2444.23 | 3726.64 | 3114.10 | 3800.61 | 959.78 | 25.25 |
| 8 | 3218.78 | 4380.91 | 4979.57 | 2489.48 | 4181.44 | 5211.82 | 4077.00 | 1045.23 | 25.64 |
| 24 | 1272.30 | 1653.10 | 2097.35 | 873.88 | 1205.43 | 2624.90 | 1621.16 | 646.26 | 39.86 |

Test Drug 1 under fasted condition (Concentration (ng/mL))

| | Subject | | | | | | | | |
|---|---|---|---|---|---|---|---|---|---|
| Time | 1 | 2 | 3 | 4 | 5 | 6 | Mean | SD | CV % |
| 0.5 | 2882.31 | 9595.39 | 11702.9 | 8397.99 | 10218.3 | 10381.4 | 8863.05 | 3121.82 | 35.22 |
| 1 | 7394.65 | 12024.7 | 13932.7 | 12425.7 | 10395.6 | 9750.23 | 10987.26 | 2306.87 | 21.00 |
| 2 | 4875.82 | 15472.4 | 13644.5 | 10380.2 | 16774.1 | 11846.8 | 12165.64 | 4261.23 | 35.03 |
| 3 | 8776.09 | 14279.2 | 15083.5 | 10486.7 | 13297.0 | 9472.33 | 11899.14 | 2660.70 | 22.36 |
| 4 | 6941.34 | 10653.6 | 15802.5 | 7525.05 | 12529.0 | 10956.5 | 10734.67 | 3275.65 | 30.51 |
| 5 | 5037.62 | 5913.15 | 7003.74 | 4942.84 | 6175.19 | 4358.75 | 5571.88 | 967.83 | 17.37 |
| 6 | 5010.16 | 6439.66 | 6541.09 | 4174.33 | 6052.34 | 7059.93 | 5879.59 | 1080.57 | 18.38 |
| 8 | 3952.23 | 4417.87 | 3946.61 | 4163.87 | 5373.19 | 2458.03 | 4051.97 | 943.79 | 23.29 |
| 24 | 1792.25 | 1932.16 | 2130.81 | 2048.65 | 2429.92 | 1130.60 | 1910.73 | 438.20 | 22.93 |

Test Drug 2 under fasted condition (Concentration (ng/mL))

| | Subject | | | | | | | | |
|---|---|---|---|---|---|---|---|---|---|
| Time | 1 | 2 | 3 | 4 | 5 | 6 | Mean | SD | CV % |
| 0.5 | 7675.35 | 2129.40 | 2311.81 | 685.16 | 471.31 | 2094.83 | 2561.31 | 2627.08 | 102.57 |
| 1 | 12666.2 | 7725.85 | 9024.96 | 4778.71 | 4674.05 | 10647.3 | 8252.85 | 3192.57 | 38.68 |
| 2 | 15668.5 | 10663.5 | 8399.64 | 13012.4 | 7585.79 | 14914.8 | 11707.44 | 3367.47 | 28.76 |
| 3 | 16020.1 | 7105.26 | 11495.2 | 14163.3 | 10294.8 | 15909.8 | 12498.08 | 3514.55 | 28.12 |
| 4 | 12375.0 | 7049.92 | 9958.48 | 9601.38 | 16536.6 | 12309.4 | 11305.13 | 3235.57 | 28.62 |
| 5 | 6029.55 | 3742.03 | 6237.27 | 8574.38 | 6291.75 | 7111.94 | 6331.15 | 1577.76 | 24.92 |
| 6 | 5371.89 | 5530.90 | 8321.44 | 7644.22 | 6445.92 | 7129.66 | 6740.67 | 1173.93 | 17.42 |
| 8 | 4392.86 | 3764.88 | 4933.94 | 5082.87 | 4895.74 | 5974.33 | 4840.77 | 736.67 | 15.22 |
| 24 | 2617.74 | 2328.62 | 1851.93 | 1748.37 | 1842.94 | 2438.64 | 2138.04 | 368.12 | 17.22 |

Figure 3:
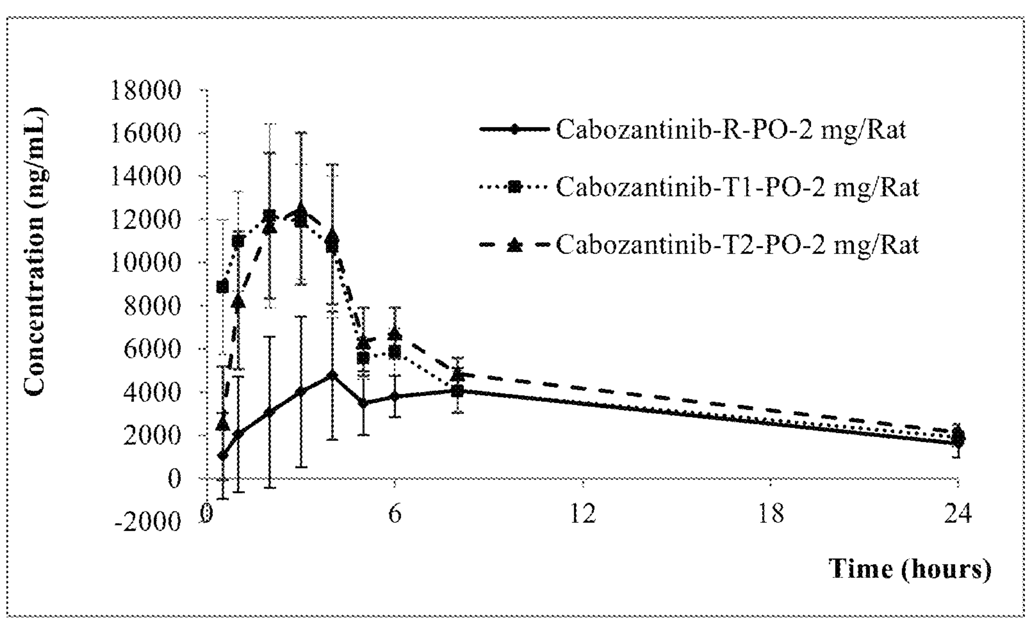
FIG. 3 is a graph of the mean in vivo plasma data provided in Example 19.

A graph of the mean plasma profiles for this study is shown in FIG. 3.

Example 20

The capsules prepared in Example 5 (Test 1) and Example 6 (Test 2) containing cabozantinib monolauryl sulfate (equivalent to 40 mg of cabozantinib free base) were administered to twenty-four (24) healthy human subjects under fasted conditions. This is a single oral dose, open-label, randomized, 3-treatment, 3-sequence, 1-period comparative bioavailability study of the two formulations of cabozantinib lauryl sulfate capsules (40 mg of cabozantinib free base) with CABOMETYX® tablets containing 60 mg of cabozantinib in the form of cabozantinib (S)-malate salt as Reference drug (Ref). All subjects will be randomized to the sequences as shown in the following table.

| Sequence | Period I |
|---|---|
| 1 | Ref |
| 2 | Test 1 |
| 3 | Test 2 |

During each treatment period, blood samples were taken at 0 (prior to the dosing), 0.5, 1, 2, 3, 4, 5, 6, 8, 10, 14, 24, 48 and 72 hours after dosing. $AUC_{0-72}$, $AUC_{0-\infty}$, $C_{max}$, $T_{max}$, and $T_{1/2}$ were determined for each subject based on non-compartmental analyses. The results were summarized in the following table:

The Pharmacokinetic Parameters for Reference and Test Formulations

| Treatment | Parameters | Geometric Mean | Mean | % CV |
|---|---|---|---|---|
| Ref $_{Fasted}$ | $C_{max}$ (ng/ml) | 411.15 | 457.792 | 36.76 |
| 60 mg | $AUC_{0-72}$ (ng · h/mL) | 13559.53 | 14608.023 | 33.66 |
| | $AUC_{0-\infty}$ (ng · h/mL) | 31246.96 | — | — |
| Test $1_{Fasted}$ | $C_{max}$ (ng/mL) | 423.75 | 429.200 | 16.65 |
| 40 mg | $AUC_{0-72}$ (ng · h/mL) | 13092.90 | 13442.464 | 23.34 |
| | $AUC_{0-\infty}$ (ng · h/mL) | 27363.66 | — | — |
| Test $2_{Fasted}$ | $C_{max}$ (ng/ml) | 392.64 | 397.063 | 15.91 |
| 40 mg | $AUC_{0-72}$ (ng · h/mL) | 11854.81 | 11952.498 | 14.69 |
| | $AUC_{0-\infty}$ (ng · h/mL) | 21830.67 | — | — |

*$Ref_{Fasted}$: 60 mg CABOMETYX ® Tablet under fasted condition.

*Test $1_{Fasted}$: Test drug 1 (Test 1) 40 mg (equivalent to 40 mg free base) under fasted condition.

*Test $2_{Fasted}$: Test drug 2 (Test 2) 40 mg (equivalent to 40 mg free base) under fasted condition.

Ln-transformed $AUC_{0-t}$, $AUC_{0-\infty}$, and $C_{max}$ were analyzed by FDA certified pharmacokinetic program Phoenix WinNonlin 7.0 (Pharsight, USA). The sequence, subject (sequence), period and treatment effects were included in the model. A comparison of the data obtained from the Test and Ref dosing is shown in the following table:

The Comparisons between Test 1 vs. Reference and Test 2 vs. Reference

| Comparisons | Parameters | Geometric Mean Ratios |
|---|---|---|
| T1 (40 mg)~Ref (60 mg | $C_{max}$ (ng/ml) | 103.06% |
| (Fasted) | $AUC_{0-72}$ (ng · h/mL) | 96.56% |
| | $AUC_{0-\infty}$ (ng · h/mL) | 87.57% |
| T2 (40 mg)~Ref (60 mg) | $C_{max}$ (ng/ml) | 95.50% |
| (Fasted) | $AUC_{0-72}$ (ng · h/mL) | 87.43% |
| | $AUC_{0-\infty}$ (ng · h/mL) | 69.86% |

The individual subject data obtained from the study is as follows:

Reference Drug under fasted condition (Concentration (ng/mL))

| Time | Subject 1 | 2 | 3 | 4 | 5 | 6 |
|---|---|---|---|---|---|---|
| 0 | 0.000 | 0.000 | 0.000 | 0.000 | 0.000 | 0.000 |
| 0.5 | 110.724 | 34.764 | 130.48 | 98.029 | 141.417 | 127.785 |
| 1 | 277.264 | 211.363 | 150.089 | 282.912 | 294.640 | 274.939 |
| 2 | 484.829 | 630.412 | 455.286 | 459.174 | 489.100 | 334.313 |
| 3 | 511.147 | 660.882 | 540.056 | 444.859 | 442.293 | 437.709 |
| 4 | 584.078 | 553.603 | 536.193 | 396.307 | 460.388 | 455.843 |
| 5 | 340.708 | 482.588 | 409.971 | 333.574 | 279.067 | 370.368 |
| 6 | 300.078 | 460.093 | 336.609 | 256.051 | 247.415 | 275.011 |
| 8 | 250.155 | 377.482 | 314.664 | 224.875 | 202.393 | 268.687 |
| 10 | 244.541 | 330.304 | 272.057 | 197.350 | 186.177 | 232.989 |
| 14 | 235.610 | 294.184 | 268.37 | 182.198 | 145.093 | 207.987 |
| 24 | 350.905 | 358.584 | 290.644 | 239.38 | 227.687 | 238.903 |
| 48 | 216.866 | 201.603 | 178.024 | 130.432 | 110.730 | 228.524 |
| 72 | 218.525 | 166.220 | 150.840 | 133.587 | 102.753 | 218.047 |

| Time | Subject 7 | 8 | Mean | SD | CV % |
|---|---|---|---|---|---|
| 0 | 0.000 | 0.000 | 0.000 | N/A | N/A |
| 0.5 | 4.289 | 0.000 | 80.936 | 58.6078 | 72.41 |
| 1 | 90.333 | 14.697 | 199.530 | 104.4709 | 52.36 |
| 2 | 268.101 | 33.926 | 394.393 | 181.3652 | 45.99 |
| 3 | 353.498 | 54.480 | 430.616 | 176.9987 | 41.10 |
| 4 | 369.702 | 98.800 | 431.864 | 154.1440 | 35.69 |
| 5 | 294.454 | 103.500 | 326.779 | 111.1707 | 34.02 |
| 6 | 256.868 | 101.578 | 279.213 | 100.0471 | 35.83 |
| 8 | 193.245 | 84.103 | 239.451 | 87.4501 | 36.52 |
| 10 | 176.506 | 75.973 | 214.487 | 75.3063 | 35.11 |
| 14 | 229.975 | 67.531 | 203.869 | 72.2451 | 35.44 |
| 24 | 233.124 | 83.908 | 252.892 | 86.3237 | 34.13 |
| 48 | 149.912 | 54.834 | 158.866 | 59.0860 | 37.19 |
| 72 | 122.789 | 56.666 | 146.178 | 55.3255 | 37.85 |

Test Drug 1 under fasted condition (Concentration (ng/mL))

| Time | Subject 1 | 2 | 3 | 4 | 5 | 6 |
|---|---|---|---|---|---|---|
| 0 | 0.000 | 0.000 | 0.000 | 0.000 | 0.000 | 0.000 |
| 0.5 | 0.000 | 0.000 | 5.224 | 4.355 | 0.000 | 0.000 |
| 1 | 0.000 | 152.946 | 35.195 | 260.464 | 40.914 | 10.002 |
| 2 | 161.568 | 387.798 | 188.711 | 459.936 | 425.285 | 200.820 |
| 3 | 378.613 | 484.593 | 320.378 | 485.1 | 522.361 | 313.892 |
| 4 | 434.600 | 493.376 | 343.882 | 478.67 | 508.428 | 320.407 |
| 5 | 373.288 | 411.169 | 282.781 | 352.248 | 360.881 | 247.066 |
| 6 | 319.124 | 335.736 | 285.281 | 287.696 | 231.992 | 216.897 |
| 8 | 287.255 | 290.599 | 238.834 | 245.325 | 219.632 | 164.714 |
| 10 | 293.473 | 264.125 | 203.335 | 242.465 | 206.445 | 163.566 |
| 14 | 249.652 | 255.075 | 144.452 | 222.917 | 191.347 | 133.646 |
| 24 | 288.309 | 283.243 | 166.109 | 313.517 | 218.080 | 132.155 |
| 48 | 205.503 | 166.663 | 111.119 | 175.155 | 186.939 | 86.606 |
| 72 | 154.138 | 149.062 | 96.801 | 163.685 | 170.476 | 73.192 |

| | Subject 7 | 8 | Mean | SD | CV % |
|---|---|---|---|---|---|
| 0 | 0.000 | 0.000 | 0.000 | N/A | N/A |
| 0.5 | 7.210 | 0.000 | 2.099 | 3.0002 | 142.96 |
| 1 | 179.694 | 10.808 | 86.253 | 97.9336 | 113.54 |
| 2 | 402.706 | 153.820 | 297.581 | 132.1471 | 44.41 |
| 3 | 430.746 | 383.389 | 414.884 | 78.4045 | 18.90 |
| 4 | 415.472 | 403.130 | 424.746 | 68.3442 | 16.09 |
| 5 | 271.107 | 301.446 | 324.998 | 57.4483 | 17.68 |
| 6 | 218.887 | 230.869 | 265.810 | 47.1304 | 17.73 |

-continued

| | | | | | |
|---|---|---|---|---|---|
| 8 | 181.620 | 195.900 | 227.985 | 46.4512 | 20.37 |
| 10 | 158.206 | 171.321 | 212.867 | 49.6809 | 23.34 |
| 14 | 136.876 | 145.300 | 184.908 | 51.7434 | 27.98 |
| 24 | 211.442 | 194.863 | 225.965 | 63.7589 | 28.22 |
| 48 | 140.248 | 142.672 | 151.863 | 39.6540 | 26.11 |
| 72 | 144.186 | 142.145 | 136.711 | 33.8838 | 24.79 |

Test Drug 2 under fasted condition (Concentration (ng/mL))

| | Subject | | | | | |
|---|---|---|---|---|---|---|
| Time | 1 | 2 | 3 | 4 | 5 | 6 |
| 0 | 0.000 | 0.000 | 0.000 | 0.000 | 0.000 | 0.000 |
| 0.5 | 0.000 | 2.180 | 0.000 | 10.809 | 4.427 | 0.000 |
| 1 | 76.076 | 51.944 | 13.680 | 151.887 | 59.847 | 68.201 |
| 2 | 254.124 | 73.122 | 282.417 | 458.670 | 164.283 | 268.162 |
| 3 | 332.163 | 236.177 | 453.756 | 424.654 | 211.619 | 398.033 |
| 4 | 341.621 | 242.471 | 452.919 | 398.157 | 233.857 | 362.484 |
| 5 | 272.654 | 331.390 | 320.426 | 249.891 | 257.700 | 276.744 |
| 6 | 246.606 | 284.847 | 239.985 | 235.119 | 210.596 | 229.368 |
| 8 | 198.218 | 217.95 | 229.829 | 184.775 | 178.956 | 216.339 |
| 10 | 188.00 | 181.835 | 186.405 | 154.742 | 252.216 | 187.983 |
| 14 | 140.14 | 167.450 | 161.948 | 145.426 | 237.433 | 153.620 |
| 24 | 187.102 | 186.953 | 242.229 | 204.491 | 317.557 | 181.214 |
| 48 | 129.62 | 121.205 | 116.518 | 135.716 | 199.781 | 111.712 |
| 72 | 125.174 | 111.516 | 86.712 | 136.337 | 158.008 | 100.318 |

| | Subject | | | | |
|---|---|---|---|---|---|
| Time | 7 | 8 | Mean | SD | CV % |
| 0 | 0.000 | 0.000 | 0.000 | N/A | N/A |
| 0.5 | 70.044 | 0.000 | 10.933 | 24.1755 | 221.13 |
| 1 | 439.006 | 35.699 | 112.043 | 138.1242 | 123.28 |
| 2 | 481.868 | 247.19 | 278.730 | 136.6652 | 49.03 |
| 3 | 453.714 | 393.612 | 362.966 | 94.4023 | 26.01 |
| 4 | 389.436 | 367.813 | 348.595 | 75.6362 | 21.70 |
| 5 | 248.864 | 271.061 | 278.591 | 31.1152 | 11.17 |
| 6 | 193.746 | 237.543 | 234.726 | 26.6708 | 11.36 |
| 8 | 165.750 | 207.001 | 199.852 | 21.9697 | 10.99 |
| 10 | 149.074 | 205.324 | 188.197 | 31.8151 | 16.91 |
| 14 | 146.407 | 167.871 | 165.037 | 31.0448 | 18.81 |
| 24 | 190.738 | 167.668 | 209.744 | 48.8206 | 23.28 |
| 48 | 118.155 | 117.063 | 131.221 | 28.7638 | 21.92 |
| 72 | 109.157 | 110.936 | 117.270 | 22.1869 | 18.92 |

Figure 4:
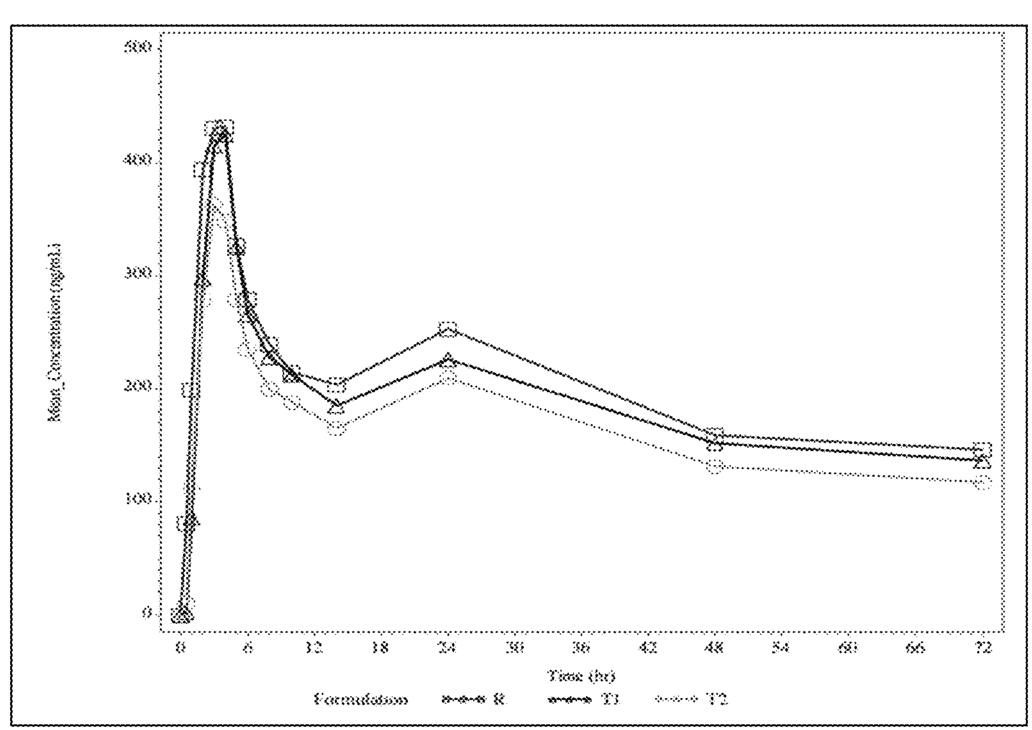
FIG. 4 is a graph of the mean in vivo plasma data provided in Example 20.

A graph of the mean plasma profiles for this study is shown in FIG. 4.

Example 21

The capsules prepared in Example 5 containing cabozantinib monolauryl sulfate (equivalent to 40 mg of cabozantinib free base) were administered to forty-five (45) healthy human subjects under fasted and fed conditions to assess the relative bioavailability and the effect of food condition. This was a single dose, open-label, randomized, 3-treatment, 3-sequence, 1-period comparative bioavailability study. The Reference drug (Ref) was the CABOMETYX® tablet, cabozantinib (S)-malate, with strength of 60 mg (free base) while the Test drug (Test) was the capsule prepared according to the procedure of Example 5 but containing 40 mg free base of cabozantinib. The forty-five (45) healthy subjects enrolled in this study were randomized to one of the sequences as shown in the following table.

| Sequence | Period I |
|---|---|
| 1 | $Ref_{fast}$ |
| 2 | $Test_{fast}$ |
| 3 | $Test_{fed}$ |

During each treatment period, blood samples were taken at 0 (prior to the dosing), 0.5, 1, 2, 3, 4, 5, 6, 8, 10, 14, 24, 48, 72, 120 and 168 hours after dosing. $AUC_{0-168}$, $AUC_{0-\infty}$, $C_{max}$, $T_{max}$, and $T_{1/2}$ were determined for each subject based on non-compartmental analyses.

Ln-transformed $AUC_{0-t}$, $AUC_{0-\infty}$ and $C_{max}$ was analyzed by ANOVA. The sequence, subject (sequence), period and treatment effects were included in the model.

The results of this study were as follows:

The Pharmacokinetic Parameters for Reference and Test Formulation

| Treatment | Parameters | Geometric Mean | Mean | % CV |
|---|---|---|---|---|
| Ref $_{Fasted}$ | $C_{max}$ (ng/mL) | 316.01 | 355.630 | 45.13 |
| 60 mg | $AUC_{0-168}$ (ng · h/mL) | 18427.20 | 20463.130 | 42.26 |
| | $AUC_{0-\infty}$ (ng · h/mL) | 26202.80 | 30091.201 | 50.36 |
| Test $_{Fasted}$ | $C_{max}$ (ng/mL) | 488.33 | 495.732 | 18.17 |
| 40 mg | $AUC_{0-168}$ (ng · h/mL) | 23666.45 | 24501.697 | 27.68 |
| | $AUC_{0-\infty}$ (ng · h/mL) | 36149.62 | 38577.392 | 38.86 |
| Test $_{Fed}$ | $C_{max}$ (ng/ml) | 342.33 | 348.286 | 18.35 |
| 40 mg | $AUC_{0-168}$ (ng · h/mL) | 22301.16 | 22835.818 | 22.01 |
| | $AUC_{0-\infty}$ (ng · h/mL) | 30916.83 | 32340.329 | 28.65 |

*Ref $_{Fasted}$: 60 mg CABOMETYX ® Tablet under fasted condition.
*Test $_{Fasted}$: Test drug (Test) 40 mg (equivalent to 40 mg free base) under fasted condition.
*Test $_{Fed}$: Test drug (Test) 40 mg (equivalent to 40 mg free base) under fed condition.

The Comparisons between Test vs. Reference and Test $_{fasted}$ VS. Test $_{fed}$

| Comparisons | Parameters | Geometric Mean Ratios |
|---|---|---|
| T (40 mg)~Ref | $C_{max}$ (ng/mL) | 154.53% |
| (60 mg) | $AUC_{0-168}$ (ng · h/mL) | 128.43% |
| (Fasted) | $AUC_{0-\infty}$ (ng · h/mL) | 137.96% |
| T (40 mg)~Ref | $C_{max}$ (ng/mL) | 108.33% |
| (60 mg) | $AUC_{0-168}$ (ng · h/mL) | 121.02% |
| (Fed) | $AUC_{0-\infty}$ (ng · h/mL) | 117.99% |
| Test $_{Fed}$~Test $_{Fasted}$ | $C_{max}$ (ng/ml) | 70.10% |
| (40 mg) | $AUC_{0-168}$ (ng · h/mL) | 94.23% |
| | $AUC_{0-\infty}$ (ng · h/mL) | 85.52% |

The individual subject data obtained from the study is as follows:

Reference Drug (Cabometyx® Tablet) under fasted condition (Concentration (ng/mL))

| Time | Subject | | | | | | | | |
|---|---|---|---|---|---|---|---|---|---|
| (hr) | 1 | 2 | 3 | 4 | 5 | 6 | 7 | 8 | 9 |
| 0 | 0.000 | 0.000 | 0.000 | 0.000 | 0.000 | 0.000 | 0.000 | 0.000 | 0.000 |
| 0.5 | 21.330 | 56.619 | 0.000 | 0.000 | 70.540 | 20.197 | 27.624 | 32.532 | 47.424 |
| 1 | 208.009 | 234.951 | 5.395 | 12.842 | 157.205 | 149.775 | 135.086 | 189.747 | 191.670 |
| 2 | 314.902 | 299.956 | 97.824 | 76.067 | 388.507 | 239.043 | 228.503 | 433.935 | 405.491 |
| 3 | 283.893 | 290.680 | 194.689 | 99.947 | 310.801 | 266.895 | 210.302 | 511.616 | 587.114 |
| 4 | 266.109 | 300.401 | 337.354 | 140.740 | 362.815 | 262.596 | 218.965 | 457.526 | 635.852 |
| 5 | 204.152 | 162.500 | 258.900 | 94.067 | 207.842 | 208.631 | 140.519 | 347.520 | 419.363 |
| 6 | 148.660 | 145.256 | 192.744 | 74.061 | 186.447 | 183.815 | 133.510 | 273.049 | 363.052 |
| 8 | 126.612 | 141.707 | 128.674 | 58.523 | 198.476 | 199.575 | 118.122 | 254.836 | 350.400 |
| 10 | 111.688 | 142.100 | 103.075 | 53.031 | 191.531 | 213.966 | 107.666 | 215.413 | 305.504 |
| 14 | 109.997 | 119.198 | 108.924 | 53.753 | 174.802 | 168.380 | 111.331 | 190.709 | 319.883 |
| 24 | 167.967 | 188.909 | 204.606 | 82.711 | 281.790 | 209.123 | 138.812 | 185.485 | 360.653 |
| 48 | 157.517 | 159.898 | 133.011 | Missing | 164.411 | 113.494 | 131.104 | 132.820 | 306.085 |
| 72 | 135.861 | 140.714 | 89.764 | 76.761 | 122.253 | 88.532 | 93.755 | 85.444 | 238.983 |
| 120 | 81.783 | 132.549 | 77.602 | 56.153 | 93.425 | 29.580 | 87.505 | 29.680 | 127.382 |
| 168 | 68.924 | 95.528 | 62.204 | 38.129 | 35.158 | 14.943 | 40.425 | 10.393 | 73.477 |

| Time | Subject | | | | | | | | |
|---|---|---|---|---|---|---|---|---|---|
| (hr) | 10 | 11 | 12 | 13 | 14 | 15 | Mean | SD | CV % |
| 0 | 0.000 | 0.000 | 0.000 | 0.000 | 0.000 | 0.000 | 0.00 | 0.00 | N/A |
| 0.5 | 60.589 | 0.000 | 138.689 | 27.254 | 16.819 | 27.892 | 36.50 | 35.70 | 97.80 |
| 1 | 303.390 | 24.881 | 329.669 | 177.667 | 174.321 | 106.912 | 160.10 | 95.26 | 59.50 |
| 2 | 421.508 | 31.420 | 587.185 | 284.810 | 362.089 | 139.621 | 287.39 | 154.40 | 53.73 |
| 3 | 490.733 | 62.867 | 555.344 | 393.773 | 451.175 | 180.044 | 325.99 | 165.11 | 50.65 |
| 4 | 427.301 | 92.729 | 590.212 | 378.139 | 453.843 | 188.394 | 340.87 | 155.38 | 45.58 |
| 5 | 318.606 | 83.164 | 383.864 | 322.889 | 312.411 | 134.145 | 239.90 | 106.70 | 44.48 |
| 6 | 244.009 | 65.376 | 316.594 | 293.631 | 259.947 | 94.720 | 198.32 | 90.79 | 45.78 |
| 8 | 245.199 | 55.984 | 309.587 | 228.589 | 227.076 | 95.040 | 182.56 | 88.24 | 48.34 |
| 10 | 236.437 | 51.453 | 269.598 | 248.259 | 204.224 | 90.018 | 169.60 | 80.68 | 47.57 |
| 14 | 211.031 | 45.815 | 251.654 | 226.626 | 174.671 | 76.445 | 156.21 | 76.85 | 49.20 |
| 24 | 241.261 | 46.201 | 290.792 | 187.952 | 233.404 | 121.460 | 196.08 | 81.18 | 41.40 |
| 48 | 179.635 | 35.704 | 226.181 | 169.272 | 188.985 | 69.046 | 154.80 | 74.27 | 47.98 |
| 72 | 178.658 | 25.951 | 176.073 | 122.680 | 186.034 | 63.293 | 121.65 | 55.72 | 45.81 |
| 120 | 128.463 | 20.870 | 118.367 | 97.482 | 141.508 | 45.848 | 84.55 | 40.67 | 48.10 |
| 168 | 136.252 | 13.615 | 90.467 | 56.805 | 98.852 | 38.378 | 58.24 | 36.19 | 62.14 |

Test Drug under fasted condition (Concentration (ng/mL))

| Time | Subject | | | | | | | | |
|---|---|---|---|---|---|---|---|---|---|
| (hr) | 1 | 2 | 3 | 4 | 5 | 6 | 7 | 8 | 9 |
| 0 | 0.000 | 0.000 | 0.000 | 0.000 | 0.000 | 0.000 | 0.000 | 0.000 | 0.000 |
| 0.5 | 2.080 | 18.530 | 70.382 | 11.991 | 18.128 | 9.984 | 0.000 | 0.000 | 6.633 |
| 1 | 16.262 | 478.558 | 315.924 | 178.250 | 276.959 | 474.030 | 107.661 | 8.974 | 211.235 |
| 2 | 477.938 | 543.469 | 416.781 | 429.505 | 445.384 | 666.567 | 616.474 | 237.063 | 386.912 |

-continued

| | | | | | | | | | |
|---|---|---|---|---|---|---|---|---|---|
| 3 | 527.873 | 395.485 | 299.017 | 333.919 | 496.038 | 580.368 | 493.525 | 447.974 | 429.257 |
| 4 | 484.582 | 397.097 | 269.060 | 264.407 | 547.626 | 596.762 | 531.347 | 533.890 | 447.990 |
| 5 | 216.884 | 294.605 | 150.180 | 181.625 | 294.013 | 321.272 | 382.408 | 384.266 | 326.998 |
| 6 | 168.136 | 189.334 | 128.867 | 134.609 | 267.366 | 281.412 | 311.457 | 326.580 | 281.490 |
| 8 | 183.321 | 166.835 | 130.835 | 114.279 | 275.464 | 308.272 | 290.152 | 318.442 | 233.645 |
| 10 | 230.067 | 136.857 | 106.109 | 101.581 | 252.376 | 245.389 | 260.331 | 282.472 | 218.021 |
| 14 | 122.555 | 119.846 | 107.559 | 110.065 | 218.442 | 240.502 | 244.442 | 277.249 | 187.380 |
| 24 | 222.379 | 157.592 | 149.317 | 171.484 | 283.541 | 388.108 | 316.658 | 247.565 | 233.352 |
| 48 | 117.178 | 123.667 | 80.361 | Missing | 183.297 | 144.622 | 239.574 | 372.481 | 148.264 |
| 72 | 88.794 | 116.770 | 68.613 | 133.683 | 101.976 | 148.899 | 171.070 | 181.000 | Missing |
| 120 | 76.999 | 87.315 | 57.178 | 107.299 | 121.023 | 320.866 | 100.593 | 95.360 | 161.352 |
| 168 | 63.650 | 78.702 | 39.422 | 65.805 | 39.635 | 158.634 | 58.274 | 64.267 | 110.139 |

| Time | Subject | | | | | | | | |
|---|---|---|---|---|---|---|---|---|---|
| (hr) | 10 | 11 | 12 | 13 | 14 | 15 | Mean | SD | CV % |
| 0 | 0.000 | 0.000 | 0.000 | 0.000 | 0.000 | 0.000 | 0.00 | 0.00 | N/A |
| 0.5 | 0.000 | 0.000 | 0.000 | 28.644 | 0.000 | 0.000 | 11.09 | 18.69 | 168.54 |
| 1 | 12.061 | 86.537 | 153.733 | 295.203 | 41.794 | 23.114 | 178.69 | 160.43 | 89.78 |
| 2 | 40.013 | 525.864 | 459.730 | 405.110 | 254.713 | 268.811 | 411.62 | 160.32 | 38.95 |
| 3 | 172.678 | 615.179 | 420.438 | 341.658 | 361.280 | 438.402 | 423.54 | 113.72 | 26.85 |
| 4 | 368.198 | 578.090 | 389.673 | 348.554 | 376.068 | 450.804 | 438.94 | 105.75 | 24.09 |
| 5 | 398.915 | 372.275 | 275.914 | 199.285 | 264.121 | 323.202 | 292.40 | 78.01 | 26.68 |
| 6 | 320.473 | 239.764 | 222.164 | 184.663 | 193.675 | 236.590 | 232.44 | 64.99 | 27.96 |
| 8 | 246.443 | 245.422 | 221.460 | 195.469 | 194.194 | 194.492 | 221.25 | 61.07 | 27.60 |
| 10 | 242.412 | 202.441 | 208.988 | 181.830 | 184.147 | 187.806 | 202.72 | 54.42 | 26.85 |
| 14 | 192.198 | 189.099 | 196.639 | 166.303 | 174.748 | 157.378 | 180.29 | 51.47 | 28.55 |
| 24 | 241.306 | 297.294 | 229.040 | 254.069 | 171.795 | 200.190 | 237.58 | 65.24 | 27.46 |
| 48 | 220.912 | 160.185 | 126.570 | 134.271 | 153.056 | 134.192 | 167.05 | 81.70 | 48.91 |
| 72 | 134.776 | 162.393 | 103.674 | 158.967 | 109.694 | 115.843 | 128.30 | 46.00 | 35.85 |
| 120 | 148.972 | 141.858 | 45.848 | 95.054 | 74.102 | 93.900 | 115.18 | 65.44 | 56.81 |
| 168 | 92.474 | 111.660 | 23.567 | 78.738 | 47.736 | 73.046 | 73.72 | 34.23 | 46.43 |

Test Drug under fed condition (Concentration (ng/mL))

| Time | Subject | | | | | | | | |
|---|---|---|---|---|---|---|---|---|---|
| (hr) | 1 | 2 | 3 | 4 | 5 | 6 | 7 | 8 | 9 |
| 0 | 0.000 | 0.000 | 0.000 | 0.000 | 0.000 | 0.000 | 0.000 | 0.000 | 0.000 |
| 0.5 | 0.000 | 0.000 | 0.000 | 0.000 | 0.000 | 0.000 | 0.000 | 0.000 | 0.000 |
| 1 | 0.000 | 0.000 | 0.000 | 2.451 | 4.695 | 0.000 | 0.000 | 0.000 | 0.000 |
| 2 | 11.615 | 20.200 | 0.000 | 95.290 | 95.225 | 0.000 | 0.000 | 135.301 | 2.843 |
| 3 | 36.728 | 60.500 | 4.340 | 225.381 | 250.256 | 0.000 | 21.370 | 207.303 | 125.799 |
| 4 | 82.823 | 135.769 | 41.018 | 312.836 | 409.520 | 14.188 | 142.933 | 211.774 | 418.043 |
| 5 | 188.447 | 269.904 | 125.605 | 338.573 | 308.569 | 236.915 | 359.975 | 242.467 | 408.754 |
| 6 | 213.206 | 211.632 | 204.877 | 377.559 | 282.793 | 324.419 | 380.980 | 246.679 | 315.974 |
| 8 | 324.381 | 164.948 | 278.762 | 392.123 | 256.189 | 262.176 | 300.472 | 200.907 | 237.024 |
| 10 | 267.000 | 157.186 | 329.642 | 350.563 | 228.752 | 244.181 | 255.844 | 162.966 | 226.323 |
| 14 | 171.060 | 136.296 | 358.817 | 328.076 | 225.720 | 215.646 | 216.094 | 135.087 | 181.969 |
| 24 | 192.310 | 158.837 | 312.265 | 324.848 | 335.053 | 274.959 | 267.969 | 225.628 | 207.149 |
| 48 | 177.805 | 134.085 | 204.253 | 238.584 | 203.379 | 349.946 | 144.380 | 100.195 | 131.451 |
| 72 | 132.764 | 123.936 | 147.515 | 175.360 | 151.205 | 158.946 | 116.392 | 61.845 | 154.403 |
| 120 | 119.560 | 128.121 | 76.272 | 131.245 | 111.095 | 138.237 | 95.610 | 37.829 | 83.151 |
| 168 | 87.582 | 84.250 | 42.242 | 70.834 | 79.488 | 69.311 | 58.385 | 21.436 | 72.336 |

| Time | Subject | | | | | | | | |
|---|---|---|---|---|---|---|---|---|---|
| (hr) | 10 | 11 | 12 | 13 | 14 | 15 | Mean | SD | CV % |
| 0 | 0.000 | 0.000 | 0.000 | 0.000 | 0.000 | 0.000 | 0.00 | 0.00 | N/A |
| 0.5 | 0.000 | 0.000 | 0.000 | 0.000 | 0.000 | 0.000 | 0.00 | 0.00 | N/A |
| 1 | 0.000 | 0.000 | 5.846 | 0.000 | 0.000 | 0.000 | 0.87 | 1.91 | 220.30 |
| 2 | 11.545 | 42.526 | 80.129 | 18.379 | 0.000 | 3.989 | 34.47 | 44.64 | 129.51 |
| 3 | 31.158 | 157.989 | 230.051 | 33.598 | 68.998 | 7.922 | 97.43 | 92.64 | 95.08 |
| 4 | 187.336 | 253.147 | 397.317 | 87.820 | 312.227 | 13.671 | 201.36 | 143.18 | 71.11 |
| 5 | 341.100 | 288.778 | 328.344 | 366.799 | 392.832 | 21.945 | 281.27 | 105.49 | 37.50 |
| 6 | 272.895 | 295.285 | 224.791 | 277.195 | 442.885 | 27.718 | 273.26 | 97.00 | 35.50 |
| 8 | 245.728 | 255.615 | 163.293 | 196.620 | 346.840 | 41.024 | 244.41 | 85.40 | 34.94 |
| 10 | 228.192 | 208.364 | 146.156 | 163.072 | 290.989 | 142.969 | 226.81 | 65.27 | 28.78 |
| 14 | 184.029 | 175.887 | 135.663 | 125.367 | 223.593 | 144.032 | 197.16 | 68.84 | 34.92 |
| 24 | 199.591 | 178.567 | 173.198 | 195.680 | 211.957 | 207.550 | 231.04 | 57.37 | 24.83 |

-continued

| | | | | | | | | | |
|---|---|---|---|---|---|---|---|---|---|
| 48 | 158.073 | 137.511 | 113.273 | Missing | 187.218 | 230.506 | 179.33 | 77.88 | 43.43 |
| 72 | 95.713 | 102.294 | 118.375 | 118.176 | 145.879 | 184.838 | 132.51 | 32.19 | 24.29 |
| 120 | 71.005 | 70.670 | 60.874 | 91.093 | 134.278 | 110.010 | 97.27 | 30.40 | 31.26 |
| 168 | 41.707 | 38.456 | 29.929 | 71.981 | 78.111 | 96.526 | 62.84 | 22.80 | 36.28 |

Figure 5:
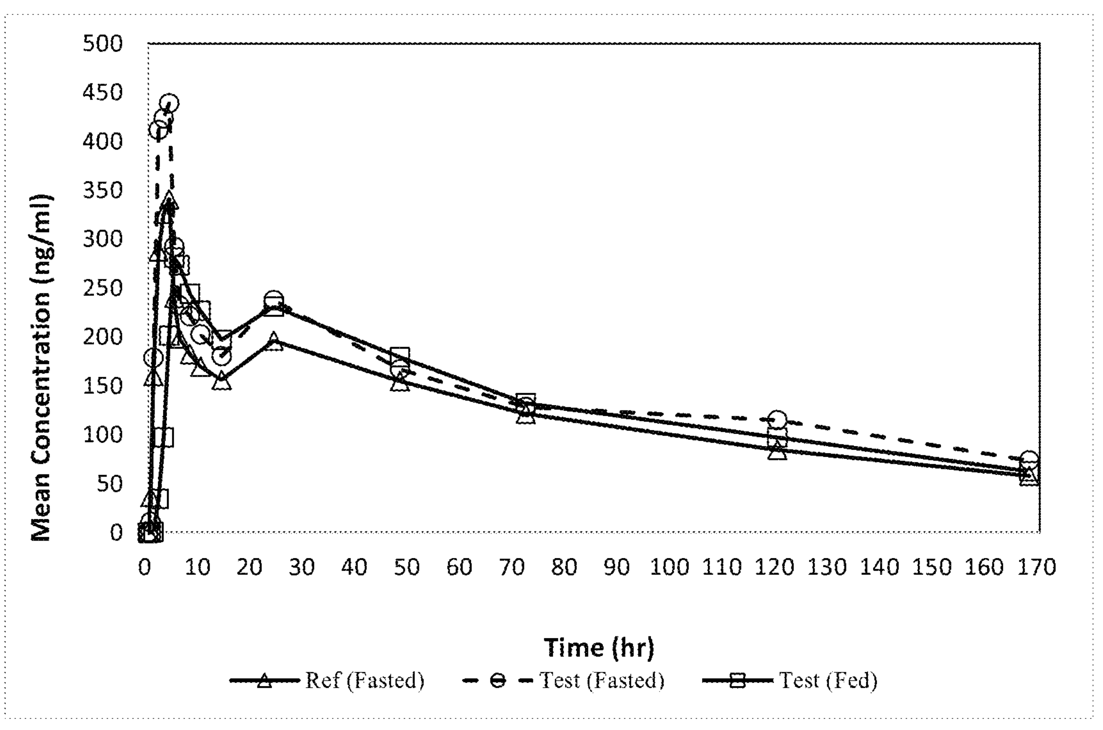
FIG. 5 is a graph of the mean in vivo plasma data provided in Example 21.

A graph of the mean plasma profiles for this study is shown in FIG. 5.

Example 22

Capsules containing the composition described in Example 5 containing cabozantinib monolauryl sulfate were administered to thirty (30) Wistar rats under fasted conditions. This is a single dose, open-label, randomized, 3-treatment, 3-sequence, 1-period bioavailability study. All subjects were randomized to the sequences as shown in the following table. The Reference drug (Ref) was prepared from CABOMETYX® tablets (obtained by crushing the commercially available 60 mg CABOMETYX® tablets containing 76.05 mg cabozantinib (S)-malate and refilling into new capsules in which each content is equivalent to 2.4 mg of cabozantinib free base) while the Test drug (Test) was a capsule prepared according to the procedure of Example 5 containing 1.6 mg free base of cabozantinib. The thirty (30) Wistar rat in this study were randomized to one of the sequences as shown in the following table.

| Sequence | Period I |
|---|---|
| 1 | Placebo |
| 2 | Ref |
| 3 | Test |

Administer the test drugs or placebo via oral gavage. One capsule once a day and last more than 28 days. The animals were fasted 3 h before the dosing and fasted 1 h after the dosing every day. Water was offered normally all through the day. The changes of diarrhea, body weight, food intake and mortality (survival rate) of rats were observed and recorded.

The results were summarized in the following tables:

TABLE 1

Effect of oral Cabozantinib on body weight in Wistar rats ($\bar{x}$ ± s, n = 10)

| | Body Weights (g)/Day | | | | | | | | | | |
|---|---|---|---|---|---|---|---|---|---|---|---|
| Treatment | D0 | D2 | D5 | D8 | D12 | D15 | D19 | D22 | D26 | D29 | D33 |
| Placebo | 197.8 | 207.0 | 218.6 | 223.4 | 245.8 | 255.0 | 265.4 | 267.6 | 277.2 | 282.5 | 293.6 |
| Test, 8 mg/kg | 197.9 | 206.2 | 213.0 | 218.8 | 229.5 | 227.7 | 221.4 | 215.2 | 207.4 | 204.3 | 193.9 |
| Ref, 12 mg/kg | 197.8 | 204.2 | 210.8 | 212.4 | 220.9 | 219.4 | 210.3 | 204.1 | 192.7 | 186.0 | 208.0* |

*Only one rat survived, resulting in a large fluctuation in average body weights.

Figure 6:
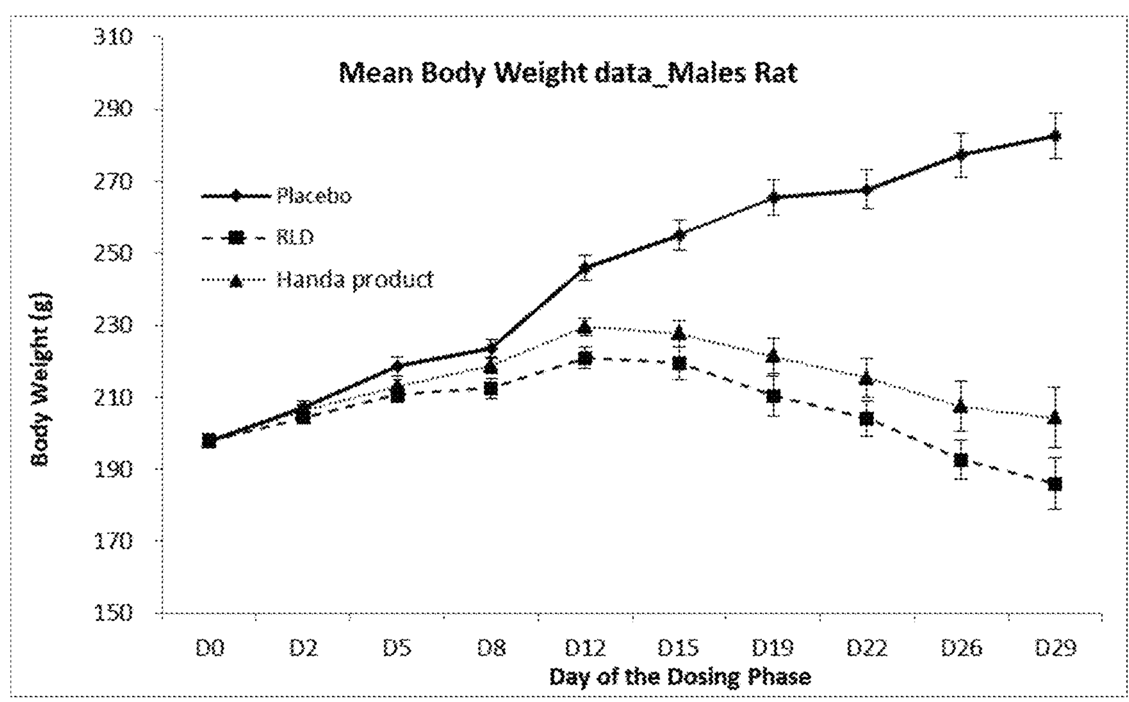
FIG. 6 is a graph of the mean body weight fluctuation data provided in Example 22.

A graph showing the fluctuation in body weight is shown in FIG. 6.

TABLE 2

Effect of oral Cabozantinib on Diarrhea score in wistar rats ($\bar{x}$ ± s, n = 10)

| | Score/Day | | | | | | | | | | | |
|---|---|---|---|---|---|---|---|---|---|---|---|---|
| Treatment | D0 | D1 | D2 | D3 | D4 | D5 | D6 | D7 | D8 | D9 | D10 | D11 |
| Placebo | 0 | 0 | 0 | 0 | 0 | 0 | 0 | 0 | 0 | 0 | 0 | 0 |
| Test, 8 mg/kg | 0 | 0 | 0 | 0 | 0 | 0.4 ± 0.8 | 0.2 ± 0.4 | 0 | 0 | 0 | 0 | 0 |
| Ref, 12 mg/kg | 0 | 0 | 0 | 0 | 0 | 0.8 ± 1 | 0.2 ± 0.4 | 0 | 0 | 0.1 ± 0.3 | 0.1 ± 0.3 | 0 |

| | Score/Day | | | | | | | | |
|---|---|---|---|---|---|---|---|---|---|
| Treatment | D12 | D13 | D14 | D15 | D16 | D17 | D18 | D19 | D20 |
| Placebo | 0 | 0 | 0 | 0 | 0 | 0 | 0 | 0 | 0 |
| Test, 8 mg/kg | 0.1 ± 0.3 | 0.2 ± 0.4 | 0.4 ± 0.5 | 0.4 ± 0.5 | 0.2 ± 0.4 | 0 | 0.4 ± 0.5 | 0 | 0.2 ± 0.4 |
| Ref, 12 mg/kg | 0.1 ± 0.3 | 0.2 ± 0.4 | 0.1 ± 0.3 | 0.4 ± 0.5 | 0 | 0 | 0.4 ± 0.5 | 0.1 ± 0.3 | 0.1 ± 0.3 |

| | Score/Day | | | | | | | | |
|---|---|---|---|---|---|---|---|---|---|
| Treatment | D21 | D22 | D23 | D24 | D25 | D26 | D27 | D28 | D29 |
| Placebo | 0 | 0 | 0 | 0 | 0 | 0 | 0 | 0 | 0 |
| Test, 8 mg/kg | 0.1 ± 0.3 | 0.2 ± 0.4 | 0.2 ± 0.7 | 0 | 0.3 ± 0.5 | 0.2 ± 0.4 | 0.6 ± 0.7 | 0.5 ± 0.5 | 0.5 ± 0.5 |
| Ref, 12 mg/kg | 0.1 ± 0.3 | 0.3 ± 0.5 | 0 | 0.1 ± 0.4 | 0.4 ± 0.8 | 0 | 0 | 0.5 ± 1 | 0.8 ± 1 |

TABLE 2-continued

Effect of oral Cabozantinib on Diarrhea score in wistar rats ($\bar{x}$ ± s, n = 10)

| Treatment | Score/Day D30 | D31 | D32 | D33 | D34 |
|---|---|---|---|---|---|
| Placebo | 0 | 0 | 0 | 0 | 0 |
| Test, 8 mg/kg | 0.6 ± 0.9 | 1.1 ± 1 | 0 | 0.1 ± 0.4 | 0.6 ± 0.5 |
| Ref, 12 mg/kg | 0 | 3 ± 1.4 | 0 | 0 | 0 |

The Diarrhea scores provided above were recorded twice/day.

Standard: 0-no diarrhea; 1-mild diarrhea, staining of anus; 2-moderate diarrhea, staining over top of legs and lower abdomen; 3-severe diarrhea, staining over legs and higher abdomen, often with continual anal leakage.

A graph showing the mean diarrhea scores is shown in FIG. 7.

TABLE 3

Effect of oral Cabozantinib on food intake in wistar rats (n = 10)

| Treatment | Food Consumption (g)/average(g)/animal · day D1~2 | D5~6 | D8~9 | D12~13 | D15~16 | D19~20 | D22~23 | D26~27 | D29~30 | D33~34 |
|---|---|---|---|---|---|---|---|---|---|---|
| Placebo | 17.7 | 17.2 | 17.1 | 19.2 | 18.6 | 16.7 | 15.8 | 17.3 | 17.9 | 18.0 |
| Test, 8 mg/kg | 17.5 | 15.4 | 7.4 | 13.2 | 11.4 | 6.3 | 7.6 | 6.5 | 7.0 | 7.6 |
| Ref, 12 mg/kg | 17.5 | 15.2 | 6.7 | 12.2 | 9.0 | 6.0 | 4.9 | 1.6 | 2.8 | 1.3 |

A graph showing the mean food intake scores is shown in FIG. 8.

Figure 9:
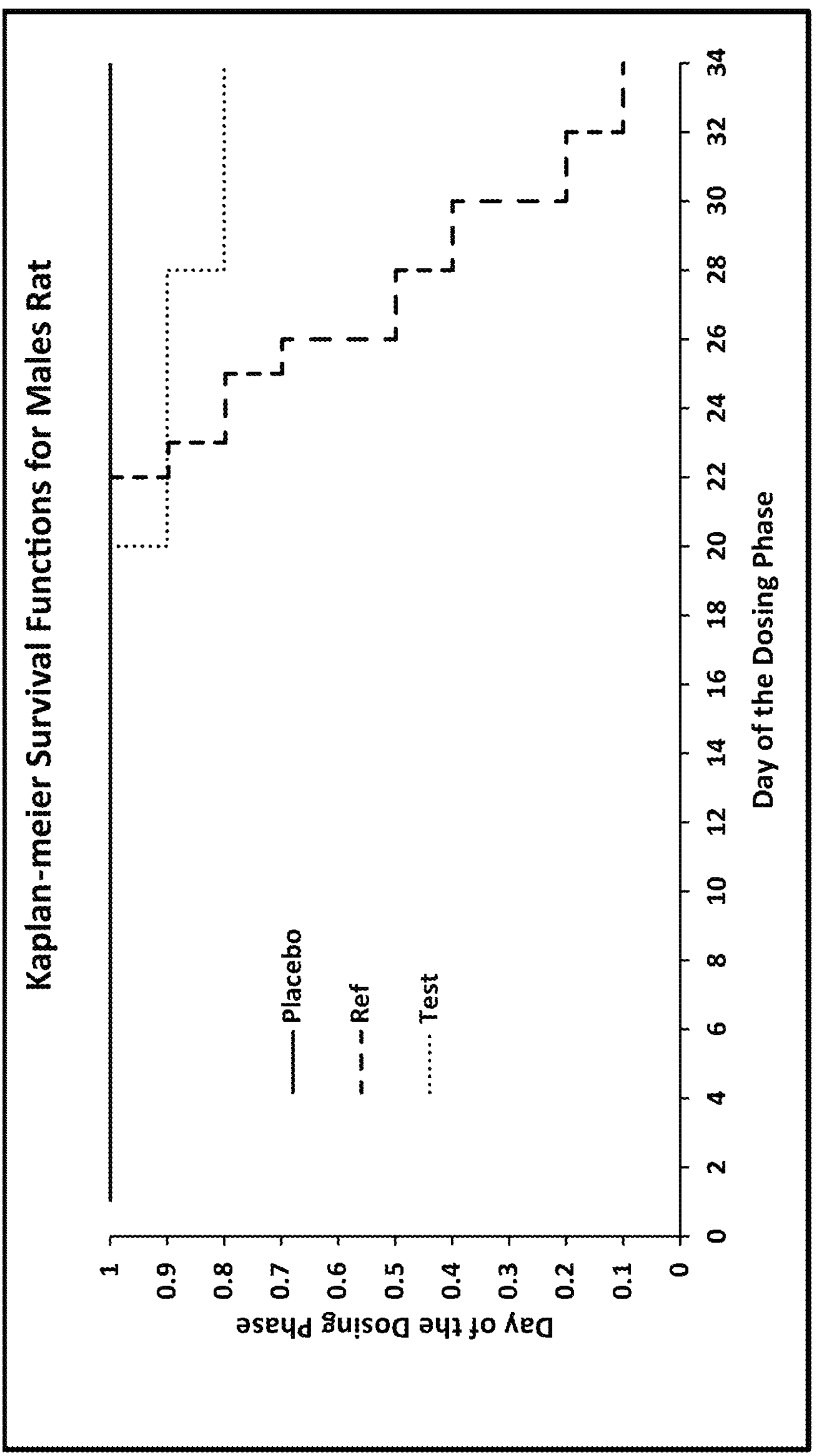
FIG. 9 is a graph of the mean survival data provided in Example 22.

A graph showing the survival function of the rats in this study is shown in FIG. 9.

The data shows the compositions in accordance with the present invention reduced the occurrence and/or severity of adverse events including but not limited to diarrhea, decreased appetite and weight loss.

Example 23

The cabozantinib lauryl sulfate used in the forgoing examples can be prepared by the method generally outlined in Example 41 of International Patent Application No. PCT/US2019/036947 filed on Jun. 13, 2019 and published as WO 2019/241504. The X-Ray Powder Diffraction (XRPD) for the cabozantinib lauryl sulfate used in Examples 12 and 14 was obtained using Empyrean (Malvern Panalytical) and employing the following testing condition:

| Anode Material: Cu | Generator Setting: 40 Kv, 40 mA |
|---|---|
| K-Alpha [Å]: 1.54060 | K-Alpha [Å]: 1.554443 |
| Scan Type: Continuous | Scan Range [°2 Th.]: 3-50 |
| Step Size [°2 Th.]: 0.0260 | Scan Step Time [s]: 45.900 |

Figure 10:
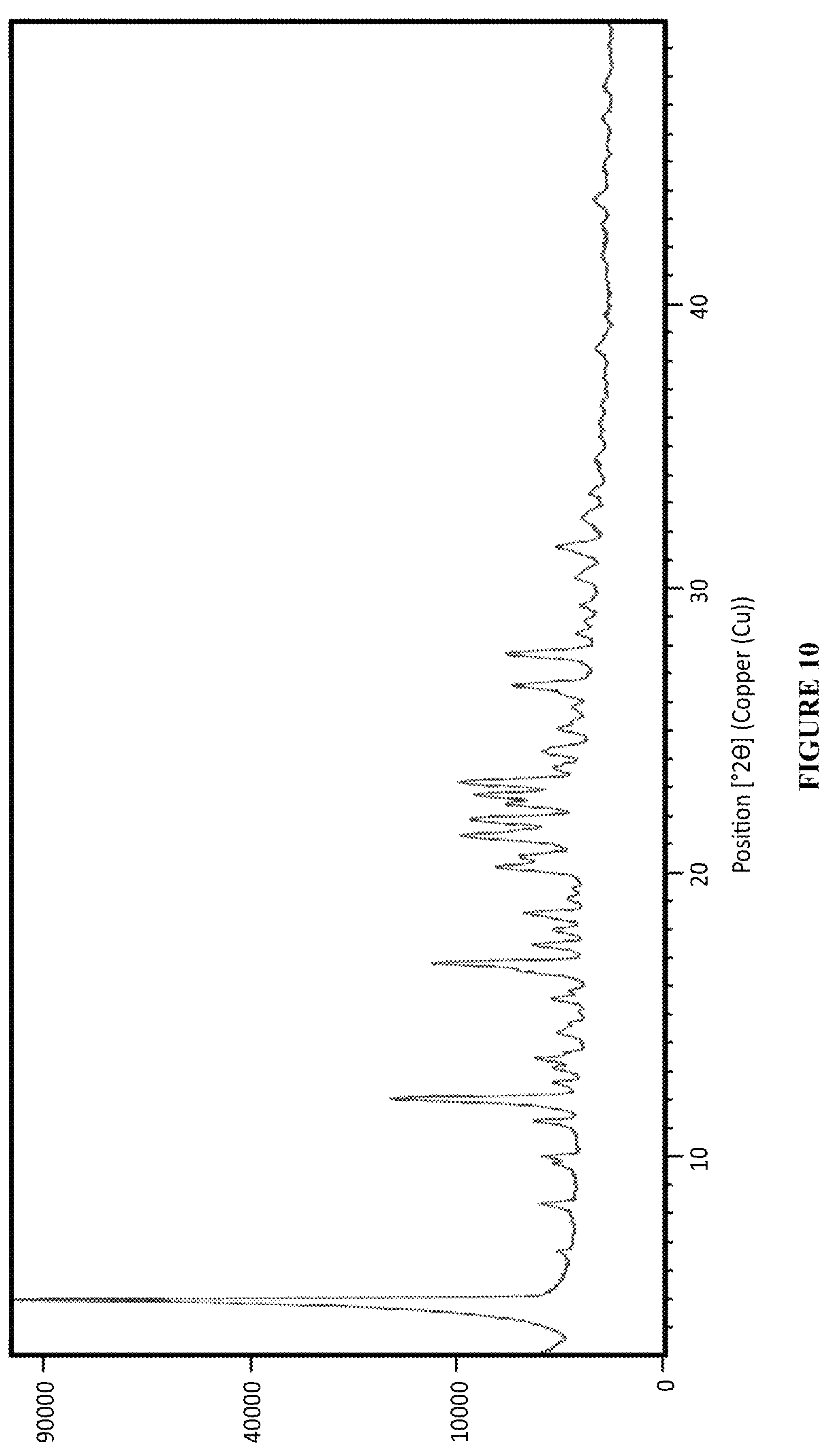
FIG. 10 is an XRPD pattern of the non-micronized cabozantinib monolauryl sulfate salt as described in Example 23.

The XPRD graph is shown in FIG. 10 and the peak values are as follows:

| 2-Theta | Rel. Int (%) |
|---|---|
| 4.97 | 100.00 |
| 10.02 | 1.70 |
| 12.62 | 1.24 |
| 14.36 | 1.16 |
| 17.46 | 2.58 |
| 20.20 | 5.43 |
| 21.90 | 7.45 |
| 23.20 | 8.74 |
| 25.07 | 1.48 |
| 27.69 | 4.90 |
| 31.50 | 1.71 |
| 34.59 | 0.20 |
| 47.65 | 0.17 |
| 6.59 | 0.4 |
| 11.28 | 2.25 |
| 13.12 | 1.28 |
| 15.57 | 1.46 |
| 17.99 | 1.49 |
| 20.58 | 3.52 |
| 22.42 | 4.64 |
| 23.67 | 1.61 |
| 26.60 | 4.30 |
| 28.41 | 0.70 |
| 32.43 | 0.66 |
| 38.44 | 0.33 |
| 8.35 | 1.80 |
| 12.07 | 15.73 |
| 13.45 | 2.27 |
| 16.83 | 11.06 |
| 18.60 | 3.10 |
| 21.30 | 8.44 |
| 22.74 | 7.24 |
| 24.24 | 2.11 |
| 27.13 | 0.25 |

-continued

| 2-Theta | Rel. Int (%) |
|---|---|
| 30.37 | 0.82 |
| 33.35 | 0.37 |
| 43.65 | 0.37 |

In certain embodiments the crystalline cabozantinib monolauryl sulfate salt will exhibit two, three, four, five, six, seven, eight, nine, ten or more of the following 2θ peaks: 5.0±0.2; 6.6±0.2; 8.4±0.2; 10.0±0.2; 11.3±0.2; 12.1±0.2; 12.6±0.2; 13.1±0.2; 13.5±0.2; 14.4±0.2; 15.6±0.2; 16.8±0.2; 17.5±0.2; 18.0±0.2; 18.6±0.2; 20.2±0.2; 20.6±0.2; 21.3±0.2; 21.9±0.2; 22.4±0.2; 22.7±0.2; 23.2±0.2, 23.7±0.2; 24.2±0.2; 25.1±0.2; 26.6±0.2; 27.1±0.2; 27.7±0.2; 28.4±0.2; 30.4±0.2; 31.5±0.2; 32.4±0.2; 33.4±0.2; 34.6±0.2; 38.4±0.2; 43.7±0.2 and/or 47.7±0.2. In certain aspects of the present invention, the crystalline cabozantinib monolauryl sulfate will exhibit one, two, three, four or more of the following 2θ peaks: 5.0±0.2; 11.3±0.2; 12.1±0.2; 13.5±0.2; 16.8±0.2; 17.5±0.2; 18.6±0.2; 20.2±0.2; 20.6±0.2; 21.3±0.2; 21.9±0.2; 22.4±0.2; 22.7±0.2; 23.2±0.2, 24.2±0.2; 26.6±0.2; and/or 27.7±0.2. In certain aspects of the present invention, the crystalline cabozantinib monolauryl sulfate salt will exhibit at least the 2θ peaks of: 5.0±0.2; 12.1±0.2; 16.8±0.2; 21.3±0.2; 21.9±0.2 and 23.2±0.2, and optionally exhibit two, three, four, five, six, seven, eight, nine, ten or more of the following 2θ peaks: 6.6 0.2; 8.4 0.2; 10.0±0.2; 11.3±0.2; 12.6±0.2; 13.1±0.2; 13.5±0.2; 14.4±0.2; 15.6±0.2; 17.5±0.2; 18.0±0.2; 18.6±0.2; 20.2±0.2; 20.6±0.2; 22.4±0.2; 22.7±0.2; 23.7±0.2; 24.2±0.2; 25.1±0.2; 26.6±0.2; 27.1±0.2; 27.7±0.2; 28.4±0.2; 30.4±0.2; 31.5±0.2; 32.4±0.2; 33.4±0.2; 34.6±0.2; 38.4±0.2; 43.7±0.2 and/or 47.7±0.2.

The cabozantinib lauryl sulfate was micronized by SJM-50 Spiral Jet Mill (Kunshan Unique) at a pulverization rate of about 0.5 g/min and employed the following parameters:

Grinding pressure: 0.6±0.05 Mpa

Feed pressure: 0.65±0.05 Mpa

Voltage: 40-60 V

The particle size of the cabozantinib lauryl sulfate for some of the examples above was measured using Malvern Mastersizer 3000 and employed the following parameters under wet mode:

| | |
|---|---|
| Particle RI | 1.52 |
| Absorption | 0.1 |
| Obscuration range | 10%~20% |
| Background measurement time | 10 secs |
| Sample measurement time | 10 secs |
| Number of measurement cycles | 3 times |
| Stirring speed of pump | 2300 rpm |

Testing Method:

(1) Dispersant medium (water with 0.05% Tween 80) preparation:

Transfer 0.5 mL of Tween 80 into 1000 mL of water in the volumetric flask. Stir the solution to mix completely.

(2) Sample preparation:

Weigh 0.0628 g of sample into 25 mL of beaker and add 10 mL of Dispersant medium. Disperse for 60 seconds with ultrasonic to form a uniform suspension system.

(3) Procedure: fill the measure cell with dispersant and add the sample solution, analyze as per measurement procedure.

The particle size data obtained is as follows:

| API LOT# | Final Product LOT# | Dv(10) | Dv(50) | Dv(90) |
|---|---|---|---|---|
| SW-002 | CT210819 (Example 1) | 5.82 | 20.4 | 50.4 |
| 20210801 | CT210820A (Example 2) | 13.5 | 38.9 | 78.1 |
| 210817A | CT2111101 (Example3)<br>CT2110282 (Example 4) | 0.837 | 2.09 | 6.32 |
| 2016-20211201A | CT220301A (Example 12)<br>CT220301D (Example 14) | 0.796 | 1.88 | 4.37 |

Example 24

The cabozantinib lauryl sulfate salt that may be used in the present invention, including the examples described herein, may be prepared according to the following reaction scheme:

Step 1—Synthesis of Intermediate 1 (4-((6,7-dimethoxyquinolin-4-yl)oxy)aniline)

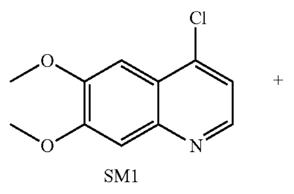

SM1

+

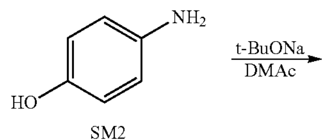

SM2

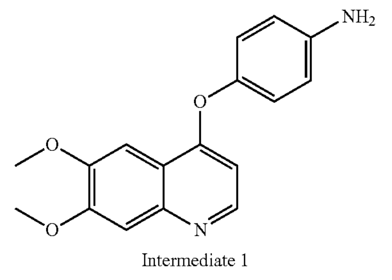

Intermediate 1

60.91 g of Dimethyl acetamide (DMAc) is added into a reactor. While stirring 6.50 g of 4-chloro-6,7-dimethoxyquinoline (compound SM1) and 3.91 g of sodium tert-butoxide are sequentially added and stirred at room temperature for about 0.5 hours and 4.45 g of p-aminophenol (compound SM2) is added. After the p-aminophenol is added the reaction mixture is continuously stirred at room temperature for about 0.5 hours. The temperature of the reaction mixture is increased to about 95-110° C. and allowed to react under nitrogen condition for about 15 hours.

Step 2—Synthesis of Intermediate 2 (1-((4-((6,7-dimethoxyquinolin-4-yl)oxy)phenyl)carbamoyl)cyclopropane-1-carboxylic acid)

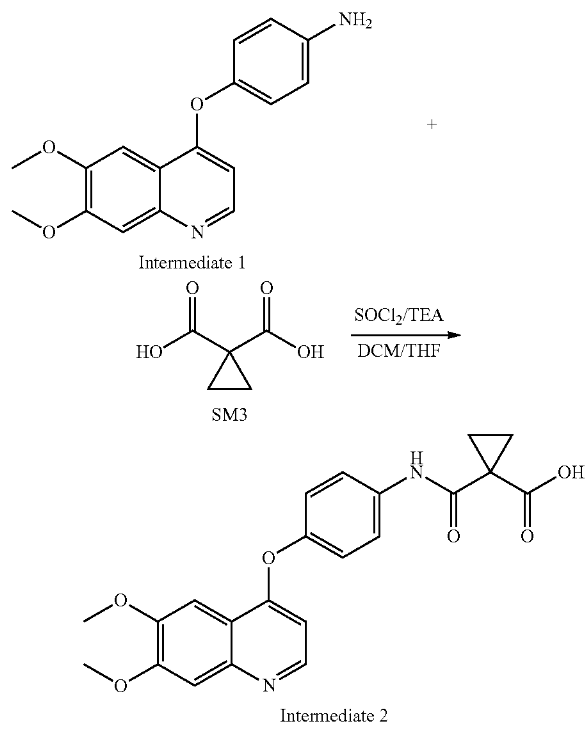

Intermediate 1

SM3

Intermediate 2

66.75 g of tetrahydrofuran is added into a first reactor and 0.23 g of dimethylformamide (DMF) catalyst is added. While stirring, 4.94 g of 1,1-cyclopropanedicarboxylic acid (compound SM3) was added to the reactor. The reactor is purged with nitrogen and the reaction mixture cooled to about 0-10° C. Once cooled, sulfoxide chloride is added to the reaction mixture and stir at about 0-10° C. for about 2 hours.

99.38 g of dichloromethane is added into a second reactor and while stirring 75.00 g of Intermediate 1 and 8.98 g of trimethylamine are sequentially added. The second reactor is purged with nitrogen and cooled to about 0-10° C. Once cooled, 71.92 g of acyl chloride solution from the first reactor is added to the third reacor while maintaining the temperature of the reaction mixture at about 0-15° C. for about 3 hours.

Step 3—Synthesis of Intermediate 3 (Crude Cabozantinib Free Base)

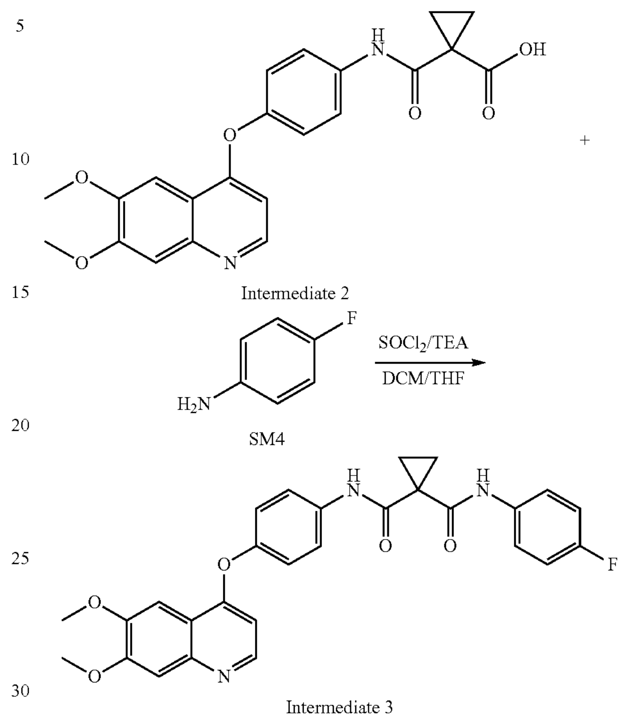

Intermediate 2

SM4

Intermediate 3

119.25 g of dichloromethane is added into a reactor and while stirring 9.00 g of Intermediate 2 is added. After Intermediate 2 is added, the reactor is purged with nitrogen and cooled to about 0-10° C. Once cooled, 3.93 g of sulfoxide chloride is added dropwise into the reactor while maintaining the temperature during the addition at about 0° C. to about 15° C. After the sulfoxide chloride is added the reaction mixture is allowed to react at about 5° C. to about 15° C. for about 3 hours. 4.46 g of triethylamine is added to the reaction mixture while maintaining the temperature of the reaction mixture below 10° C. After the trimethylamine is added, 3.67 g of 4-fluoroaniline is added while maintaining the temperature of the reaction mixture below 15° C. After the 4-fluoroaniline is added the temperature of the reaction mixture is raised to about 30° C. to about 40° C., and allow reacting for about 2 hours.

Step 4—Synthesis of Cabozaninib Lauryl Sulfate

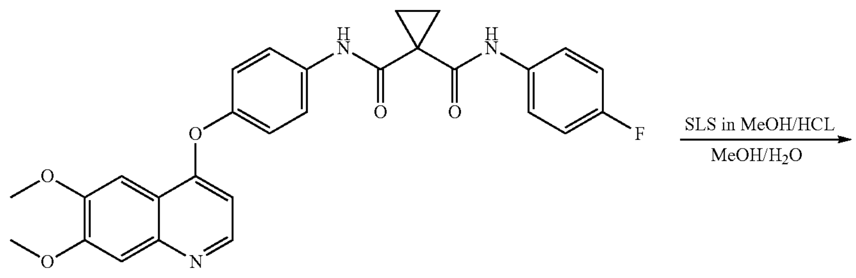

Cabozantinib Free Base
Intermediate 3

-continued

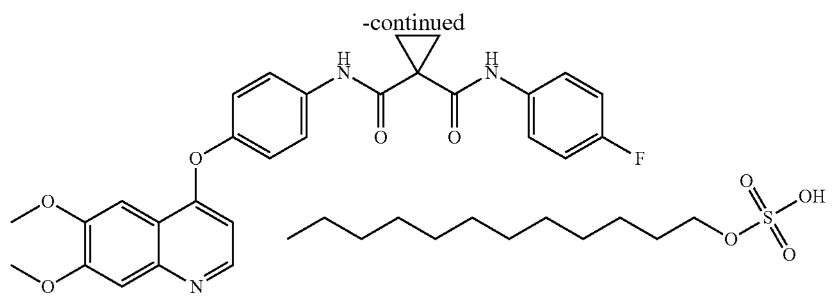

Cabozantinib Lauryl Sulfate Salt 4.86 g of sodium lauryl sulfate, 15.42 g of methanol and 1 mol/L hydrochloric acid solution are added to a transfer barrel and stir until completely dissolved.

128.54 g of methanol is added to a reactor. While stirring, 6.50 g of Intermediate 3 is added to the reactor and the reaction mixture is heated to about 45° C. to about 55° C. The sodium lauryl sulfate/methanol/hydrochloric acid solution is added to the reaction mixture while stirring until the reactants are completely dissolved and then maintained at the temperature for about 0.5 hours. The resulting mixture is transferred by hot filtration into a new clean reactor and the filtrate is stirred at about 45° C. to about 55° C. for about 0.5 hours and then cooled to about 20° C. to about 30° C. react for about 1 hour.

Step 5—Crystallization of Cabozaninib Lauryl Sulfate (a) Part of methanol is removed from the reaction mass of step 4 by vacuum concentration followed by a dropwise addition of 97.50 g of purified water at about 20° C. to about 30° C. for about 2-2.5 hours. The temperature of the reaction mixture should be below 35° C. during the water addition process. After the water is added, the reaction mixture is stirred about 1 hour allowing crystallization, and the resulting crystals are collected as a wet cake by centrifuge.

(b) 130.00 g of purified water is added to a reactor and the wet cake from step (a) is slurried at about 20° C. to about 30° C. for about 1 hour and centrifuge to collect a wet cake.

(c) 61.70 g of methanol is added into a reactor and the wet cake from step (b) is added and the reaction mixture is heated to about 55° C. to about 70° C. and stirred until completely dissolved. The solution is maintained at the temperature for about 0.5 hours, and then cooled to about 20° C. to about 30° C. After cooling 117.00 g of purified water is added dropwise over about 1-2 hours and the temperature is maintained below 35° C. during the water adding process. Once the water is added the cabozantinib lauryl sulfate is allowed to crystallize while maintaining the temperature for about 1 hour.

(d) The reaction mixture from step (c) is centrifuged and the resulting wet cake is washed with purified water before each discharge. The centrifuging is continued until no liquid flows out as observed through the view glass before each discharge.

(e) The wet purified cabozantinib lauryl sulfate crystals from step (d) are discharged and dried under vacuum at about 45° C. to about 55° C. for about 20 hours, to afford a Yield: 70-95% which can be jet milled to afford target, mill yield: 90-100%.

Example 25

Figure 11A:
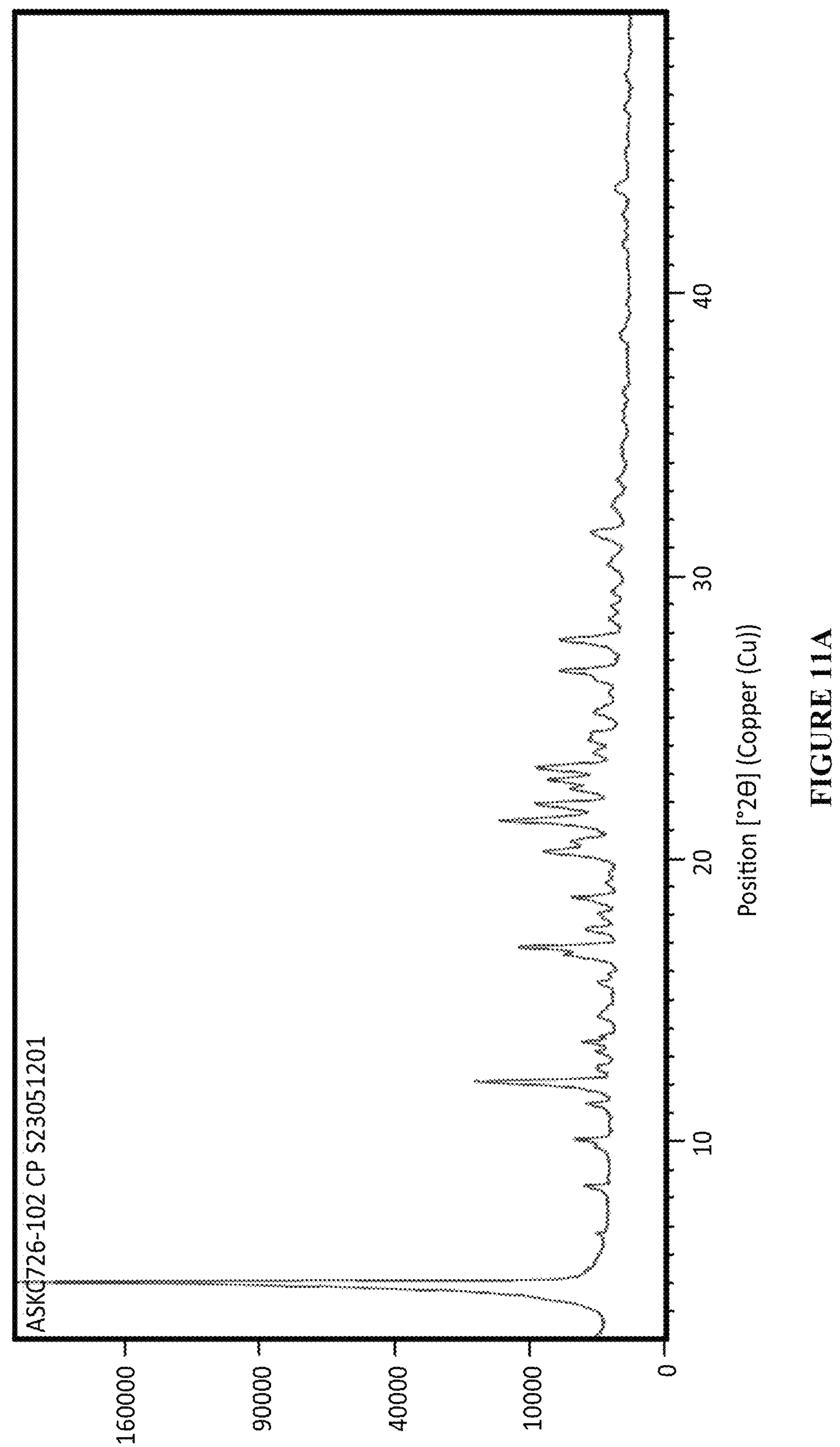
FIGS. 11A, 11B and 11C are the XRPD patterns for the cabozantinib monolauryl sulfate salt as described in Examples 25A, 25B and 25C respectively.
Figure 11B:
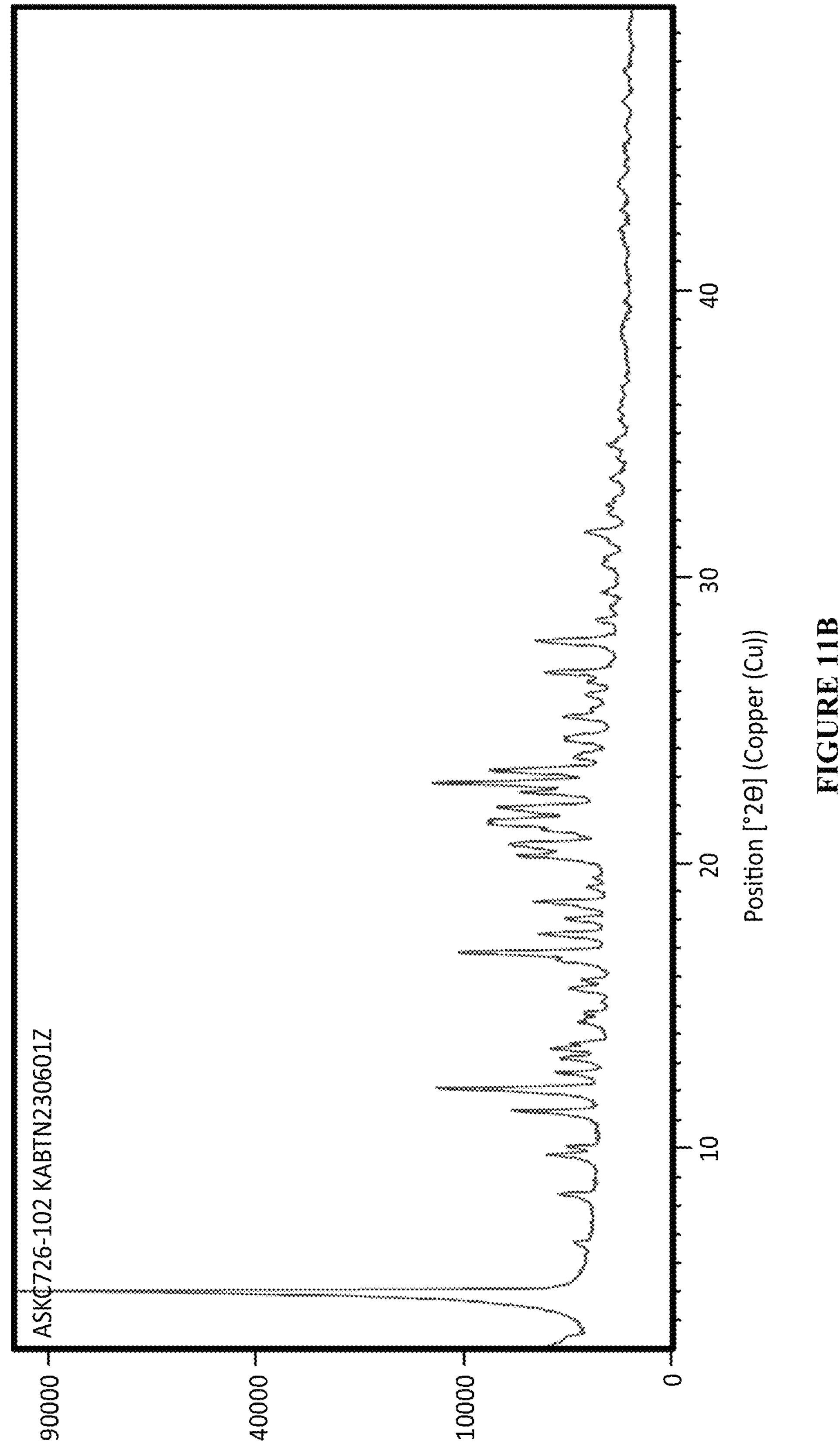
Figure 11C:
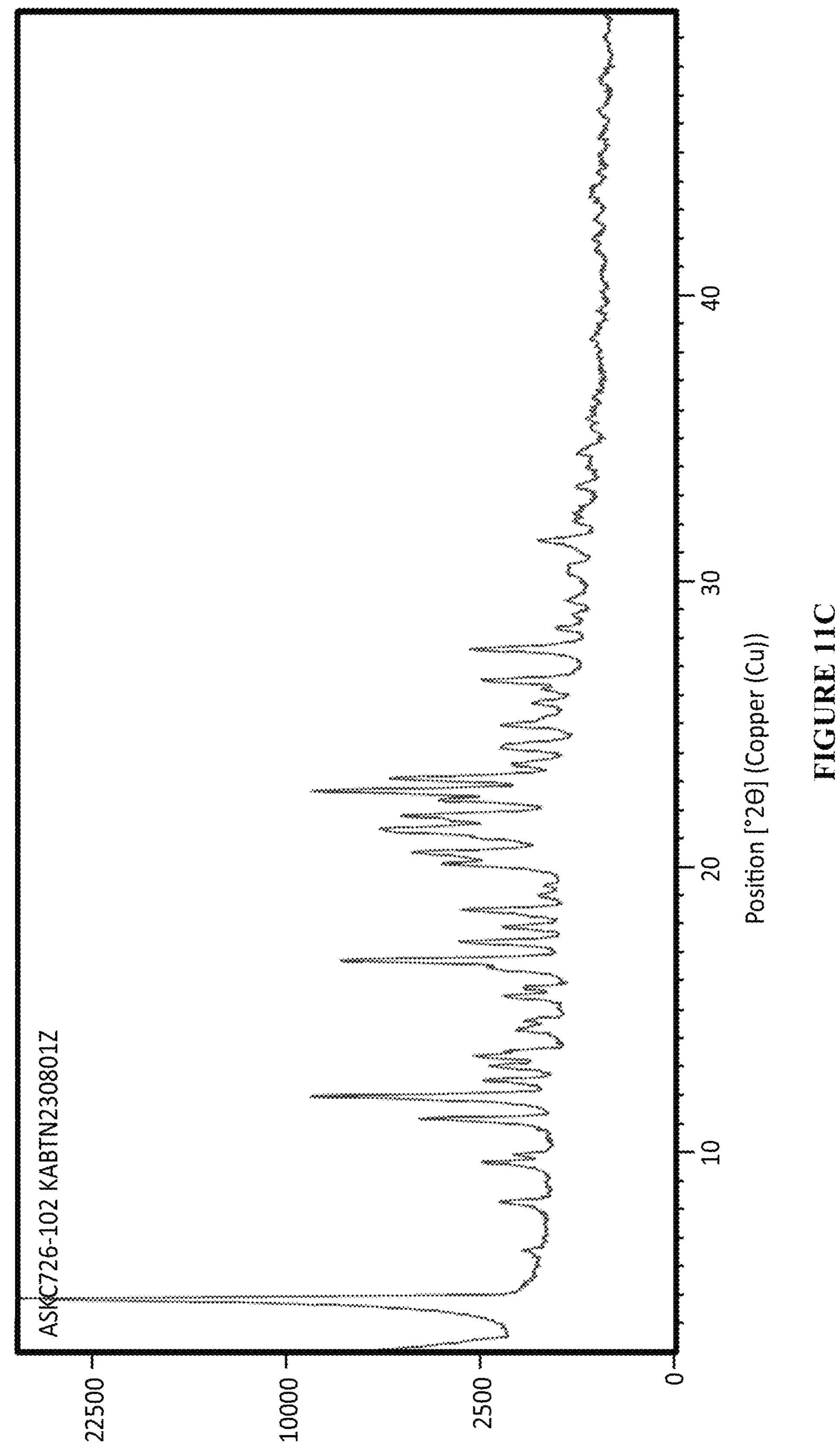

Three (3) lots of crystalline cabozantinib lauryl sulfate were prepared using the procedure outlined in Example 24 and the XRPD was determined for each lot according to the procedure of Example 23. The XPRD graphs for the three lots 25A, 25B and 25C are shown in FIGS. 11A, 11B and 11C respectively and the peak values are as follows:

| 2-Theta | Rel. Int (%) |
|---|---|
| 5.03 | 100.00 |
| 10.08 | 1.23 |
| 12.62 | 0.40 |
| 14.42 | 0.40 |
| 16.88 | 4.50 |
| 18.65 | 1.45 |
| 20.63 | 1.56 |
| 22.48 | 1.62 |
| 23.76 | 0.66 |
| 25.13 | 0.67 |
| 28.47 | 0.30 |
| 30.39 | 0.35 |
| 33.41 | 0.17 |
| 38.56 | 0.19 |
| 6.70 | 0.22 |
| 11.35 | 0.76 |
| 13.19 | 0.43 |
| 15.63 | 0.43 |
| 17.53 | 0.90 |
| 19.12 | 0.26 |
| 21.35 | 5.89 |
| 22.81 | 2.71 |
| 24.18 | 0.85 |
| 26.65 | 2.14 |
| 28.92 | 0.23 |
| 31.57 | 0.79 |
| 34.65 | 0.08 |
| 43.64 | 0.24 |
| 8.42 | 0.79 |
| 12.13 | 7.78 |
| 13.52 | 0.94 |
| 16.60 | 1.75 |
| 18.06 | 0.48 |
| 20.26 | 2.98 |
| 21.95 | 3.26 |
| 23.26 | 3.34 |
| 24.46 | 0.73 |
| 27.75 | 2.09 |
| 29.45 | 0.25 |
| 32.54 | 0.28 |
| 36.51 | 0.10 |
| 46.57 | 0.08 |

In certain embodiments the crystalline cabozantinib monolauryl sulfate salt will exhibit two, three, four, five, six, seven, eight, nine, ten or more of the following 2θ peaks: 5.0±0.2; 6.7±0.2; 8.4±0.2; 10.1±0.2; 11.4±0.2; 12.1±0.2; 12.6±0.2; 13.2±0.2; 13.5±0.2; 14.4±0.2; 15.6±0.2; 16.6±0.2; 16.9±0.2; 17.5±0.2; 18.1±0.2; 18.7±0.2; 19.1±0.2; 20.3±0.2; 20.6±0.2; 21.4±0.2; 22.0±0.2; 22.5±0.2; 22.8±0.2; 23.3±0.2, 23.8±0.2; 24.2±0.2; 24.5±0.2; 25.1±0.2; 26.7±0.2; 27.8±0.2; 28.5±0.2; 28.9±0.2; 29.5±0.2; 30.4±0.2; 31.6±0.2; 32.5±0.2; 33.4±0.2; 34.7±0.2; 36.5±0.2; 38.6±0.2; 43.6±0.2 and/or 46.6±0.2. In certain aspects of the present invention, the crystalline cabozantinib monolauryl sulfate will exhibit one, two, three, four or more of the following 2θ peaks: 5.0±0.2; 10.1±0.2; 12.1±0.2; 16.6±0.2; 16.9±0.2; 18.7±0.2; 20.3±0.2; 20.6±0.2; 21.4±0.2; 22.0±0.2; 22.5±0.2; 22.8±0.2; 23.3±0.2; 26.7±0.2; and/or 27.8±0.2.

In certain aspects of the present invention, the crystalline cabozantinib monolauryl sulfate salt will exhibit at least the 2θ peaks of: 5.0±0.2; 12.1±0.2; 16.9±0.2; 21.4±0.2; 22.0±0.2 and 23.3±0.2, and optionally exhibit two, three, four, five, six, seven, eight, nine, ten or more of the following 2θ peaks: 6.7±0.2; 8.4±0.2; 10.1±0.2; 11.4±0.2; 12.6±0.2; 13.2±0.2; 13.5±0.2; 14.4±0.2; 15.6±0.2; 16.6±0.2; 17.5±0.2; 18.1±0.2; 18.7±0.2; 19.1±0.2; 20.3±0.2; 20.6±0.2; 22.5±0.2; 22.8±0.2; 23.8±0.2; 24.2±0.2; 24.5±0.2; 25.1±0.2; 26.7±0.2; 27.8±0.2; 28.5±0.2; 28.9±0.2; 29.5±0.2; 30.4±0.2; 31.6±0.2; 32.5±0.2; 33.4±0.2; 34.7±0.2; 36.5±0.2; 38.6±0.2; 43.6±0.2 and/or 46.6±0.2.

| 2-Theta | Rel. Int (%) |
|---|---|
| 5.01 | 100.00 |
| 9.79 | 2.35 |
| 12.11 | 11.73 |
| 13.50 | 2.25 |
| 15.60 | 1.37 |
| 16.86 | 9.68 |
| 18.63 | 3.48 |
| 20.67 | 4.83 |
| 21.94 | 6.14 |
| 23.24 | 6.80 |
| 24.39 | 1.77 |
| 26.32 | 0.84 |
| 28.47 | 0.59 |
| 31.55 | 1.11 |
| 34.66 | 0.34 |
| 43.73 | 0.22 |
| 6.69 | 0.60 |
| 10.06 | 1.30 |
| 12.66 | 2.01 |
| 13.70 | 1.22 |
| 15.90 | 0.80 |
| 17.51 | 3.19 |
| 19.15 | 0.62 |
| 21.33 | 6.84 |
| 22.45 | 4.56 |
| 23.68 | 1.40 |
| 25.09 | 1.96 |
| 26.64 | 2.95 |
| 29.45 | 0.41 |
| 32.20 | 0.33 |
| 38.59 | 0.14 |
| 46.61 | 0.13 |
| 8.40 | 1.52 |
| 11.32 | 4.78 |
| 13.17 | 1.72 |
| 14.40 | 0.90 |
| 16.57 | 2.01 |
| 18.03 | 1.60 |
| 20.23 | 4.66 |
| 21.50 | 6.54 |
| 22.79 | 12.60 |
| 24.24 | 1.73 |
| 25.87 | 0.97 |
| 27.74 | 3.54 |
| 30.53 | 0.41 |
| 33.43 | 0.32 |
| 42.10 | 0.17 |

In certain embodiments the crystalline cabozantinib monolauryl sulfate salt will exhibit two, three, four, five, six, seven, eight, nine, ten or more peaks of the following 2θ peaks: 5.0±0.2; 6.7±0.2; 8.4±0.2; 9.8±0.2; 10.1±0.2; 11.3±0.2; 12.1±0.2; 12.7±0.2; 13.2±0.2; 13.5±0.2; 13.7±0.2; 14.4±0.2; 15.6±0.2; 15.9±0.2; 16.6±0.2; 16.9±0.2; 17.5±0.2; 18.0±0.2; 18.6±0.2; 19.2±0.2; 20.2±0.2; 20.7±0.2; 21.3±0.2; 21.5±0.2; 21.9±0.2; 22.5±0.2; 22.8±0.2; 23.2±0.2, 23.7±0.2; 24.2±0.2; 24.4±0.2; 25.1±0.2; 25.9±0.2; 26.3±0.2; 26.6±0.2; 27.7±0.2; 28.5±0.2; 29.5±0.2; 30.5±0.2; 31.6±0.2; 32.2±0.2; 33.4±0.2; 34.7±0.2; 38.6±0.2; 42.1±0.2; 43.7±0.2 and/or 46.6±0.2. In certain aspects of the present invention, the crystalline cabozantinib monolauryl sulfate will exhibit one, two, three, four or more of the following 2θ peaks: 5.0±0.2; 8.4±0.2, 9.79±0.2, 11.3±0.2; 12.1±0.2; 12.7±0.2, 13.2±0.2; 13.5±0.2, 16.6±0.2, 16.9±0.2; 17.5±0.2; 18.0±0.2, 18.6±0.2; 20.2±0.2; 20.7±0.2; 21.3±0.2; 21.5±0.2, 21.9±0.2; 22.5±0.2; 22.8±0.2; 23.2±0.2, 24.2±0.2; 24.4±0.2, 25.1±0.2, 26.6±0.2; and/or 27.7±0.2.

In certain aspects of the present invention, the crystalline cabozantinib monolauryl sulfate salt will exhibit at least the 2θ peaks of: 5.0±0.2; 12.1±0.2; 16.9±0.2; 20.7±0.2; 21.9±0.2 and 22.8±0.2, and optionally exhibit two, three, four, five, six, seven, eight, nine, ten or more of the following 2θ peaks: 6.7±0.2; 8.4±0.2; 9.8±0.2; 10.1±0.2; 11.3±0.2; 12.7±0.2; 13.2±0.2; 13.5±0.2; 13.7±0.2; 14.4±0.2; 15.6±0.2; 15.9±0.2; 16.6±0.2; 17.5±0.2; 18.0±0.2; 18.6±0.2; 19.2±0.2; 20.2±0.2; 21.3±0.2; 21.5±0.2; 22.5±0.2; 23.2±0.2, 23.7±0.2; 24.2±0.2; 24.4±0.2; 25.1±0.2; 25.9±0.2; 26.3±0.2; 26.6±0.2; 27.7±0.2; 28.5±0.2; 29.5±0.2; 30.5±0.2; 31.6±0.2; 32.2±0.2; 33.4±0.2; 34.7±0.2; 38.6±0.2; 42.1±0.2; 43.7±0.2 and/or 46.6±0.2.

Example 25C (Lot KABTN230801Z)*

| 2-Theta | Rel. Int (%) |
|---|---|
| 4.88 | 100.00 |
| 9.92 | 2.64 |
| 12.53 | 5.50 |
| 14.28 | 2.72 |
| 15.77 | 2.14 |
| 17.37 | 8.49 |
| 20.09 | 10.50 |
| 21.35 | 18.20 |
| 22.65 | 30.04 |
| 24.13 | 4.80 |
| 26.51 | 7.03 |
| 29.31 | 0.85 |
| 33.30 | 0.74 |
| 43.65 | 0.36 |
| 8.27 | 3.50 |
| 11.18 | 12.35 |
| 13.02 | 5.00 |
| 14.62 | 2.12 |
| 16.42 | 5.07 |
| 17.90 | 4.25 |
| 20.52 | 14.09 |
| 21.80 | 15.90 |
| 23.09 | 17.68 |
| 24.95 | 5.06 |
| 27.60 | 8.18 |
| 30.43 | 0.92 |

-continued

| 2-Theta | Rel. Int (%) |
|---|---|
| 34.55 | 0.74 |
| 9.65 | 5.32 |
| 11.97 | 29.35 |
| 13.35 | 6.55 |
| 15.46 | 3.93 |
| 16.73 | 24.87 |
| 18.49 | 8.43 |
| 21.21 | 16.53 |
| 22.32 | 11.21 |
| 23.57 | 3.84 |
| 25.73 | 2.70 |
| 28.33 | 1.40 |
| 31.41 | 2.81 |
| 35.66 | 0.29 |

*XRPD Scan Step Time was 42.840

In certain embodiments the crystalline cabozantinib monolauryl sulfate salt will exhibit two, three, four, five, six, seven, eight, nine, ten or more of the following 2θ peaks: 4.9±0.2; 8.3±0.2; 9.7±0.2; 9.9±0.2; 11.2±0.2; 12.0±0.2; 12.5±0.2; 13.0±0.2; 13.4±0.2; 14.3±0.2; 14.6±0.2; 15.5±0.2; 15.8±0.2; 16.4±0.2; 16.7±0.2; 17.4±0.2; 17.9±0.2; 18.5±0.2; 20.1±0.2; 20.5±0.2; 21.2±0.2; 21.4±0.2; 21.8±0.2; 22.3±0.2; 22.7±0.2; 23.1±0.2, 23.6±0.2; 24.1±0.2; 25.0±0.2; 25.7±0.2; 26.5±0.2; 27.6±0.2; 28.3±0.2; 29.3±0.2; 30.4±0.2; 31.4±0.2; 33.3±0.2; 34.6±0.2; 35.7±0.2 and/or 43.7±0.2. In certain aspects of the present invention, the crystalline cabozantinib monolauryl sulfate will exhibit one, two, three, four or more of the following 2θ peaks: 4.9±0.2; 9.7±0.2, 11.2±0.2; 12.0±0.2; 12.5±0.2, 13.0±0.2; 13.4±0.2, 16.4±0.2, 16.7±0.2; 17.4±0.2; 18.5±0.2; 20.1±0.2; 20.5±0.2; 21.2±0.2; 21.4±0.2; 21.8±0.2, 22.3±0.2; 22.7±0.2; 23.1±0.2, 25.0±0.2; 26.5±0.2; and/or 27.6±0.2.

In certain aspects of the present invention, the crystalline cabozantinib monolauryl sulfate salt will exhibit at least the 2θ peaks of: 4.9±0.2; 12.0±0.2; 16.7±0.2; 21.2±0.2; 22.7±0.2 and 23.1±0.2, and optionally exhibit two, three, four, five, six, seven, eight, nine, ten or more of the following 2θ peaks: 8.3±0.2; 9.7±0.2; 9.9±0.2; 11.2±0.2; 12.5±0.2; 13.0±0.2; 13.4±0.2; 14.3±0.2; 14.6±0.2; 15.5±0.2; 15.8±0.2; 16.4±0.2; 17.4±0.2; 17.9±0.2; 18.5±0.2; 20.1±0.2; 20.5±0.2; 21.4±0.2; 21.8±0.2; 22.3±0.2; 23.6±0.2; 24.1±0.2; 25.0±0.2; 25.7±0.2; 26.5±0.2; 27.6±0.2; 28.3±0.2; 29.3±0.2; 30.4±0.2; 31.4±0.2; 33.3±0.2; 34.6±0.2; 35.7±0.2 and/or 43.7±0.2.

The cabozantinib lauryl sulfate of Examples 25B and 25C were packed in aluminum foil bag double-lined low-density polyethylene bags and stored at 40° C. and 75% relative humidity. The impurity profile was measured as follows:

1. Related Substance 1

1.1 Chromatographic Conditions

| Column | | Waters XSelect CSH C18, 4.6 mm × 150 mm, 3.5 μm | |
|---|---|---|---|
| Injection volume | | 5 μL | |
| Mobile phase | A | 0.02M $KH_2PO_4$ (0.1% TEA)-Acetonitrile: Methanol 90:8:2 | |
| | B | Acetonitrile: Methanol 80:20 | |
| | Time (min) | Mobile phaseA (%) | Mobile phase B (%) |
| Gradient elution | 0 | 80 | 20 |
| | 5 | 70 | 30 |
| | 20 | 55 | 45 |
| | 25 | 55 | 45 |
| | 45 | 30 | 70 |
| | 50 | 20 | 80 |
| | 51 | 80 | 20 |
| | 60 | 80 | 20 |
| Flow rate | | 1.0 mL/min | |
| Detection | | UV at 242 nm | |
| Column temperature | | 35° C. | |
| Run Time | | 60 minutes | |

1.2 Preparation of Solution

Blank Solution: 90% MeOH. Take 900 mL of methanol, add 100 mL of water and mix well.

Reference Standard Solution: Accurately weigh about 18 mg of Cabozantinib Laurylsulfate standard and transfer into a 20-mL volumetric flask, dissolve and dilute to volume with Diluent, mix well. Transfer 1.0 mL of above Solution into a 50-mL volumetric flask, and dilute to volume with Diluent, mix well. Transfer 1.0 mL of above Solution into a 20-mL volumetric flask, and dilute to volume with Diluent, mix well.

Sample Solution: Accurately weigh about 18 mg of API and transfer into a 20-mL volumetric flask, dissolve and dilute to volume with Diluent, mix well.

2. Related Substance 2 (GTIs, Genotoxic Impurities)

2.1 Chromatographic Conditions

| Column | | ACE Excel 5 C18-PFP, 4.6 mm × 250 mm, 5 μm | |
|---|---|---|---|
| Injection volume | | 10 μL | |
| Mobile phase | A | 0.02M $KH_2PO_4$ (0.1% TEA)-Acetonitrile 95:5 | |
| | B | Acetonitrile | |
| | Time (min) | Mobile phaseA (%) | Mobile phase B (%) |
| Gradient elution | 0 | 95 | 5 |
| | 5 | 89 | 11 |
| | 15 | 58 | 42 |
| | 35 | 58 | 42 |
| | 45 | 42 | 58 |
| | 55 | 21 | 79 |
| | 60 | 21 | 79 |
| | 70 | 95 | 5 |
| Flow rate | | 1.0 mL/min | |
| Detection | | UV at 245 nm | |
| Column temperature | | 25° C. | |
| Run Time | | 70 minutes | |

2.2 Preparation of Solution

Blank Solution: DMSO-MeOH 80:20. Take 800 mL of DMO, add 200 mL of methanol and mix well.

Reference Standard Solution: Accurately weigh about 9 mg of SM1-Imp4 standard, 9 mg of SM2 standard, 9 mg of SM4 standard, 9 mg of Int1 standard and 9 mg of Int1-Imp11 standard and transfer into a same 100-mL volumetric flask, dissolve and dilute to volume with Diluent, mix well. Transfer 1.0 mL of above Solution into a 100-mL volumetric flask, and dilute to volume with Diluent, mix well.

Sample Solution: Accurately weigh about 760 mg of API and transfer into a 10-mL volumetric flask, add about 800 full ofDiluent, sonicate for one minute while shakingto dissolve and dilute to volume with Diluent, mix well.

The identified impurities are listed below, and each of the identified impurities is present in the Cabozantinib lauryl sulfate of an amout less than 0.2%, less than 0.150%, less than 0.10%, or less than 0.050%:

| No. | Item | Name |
|---|---|---|
| 1 | Int2-Imp1 | N,N'-bis(4-((6,7-dimethoxyquinolin-4-yl)oxy)phenyl)cyclopropane-1,1-dicarboxamide |
| 2 | Int3-Imp2 | N-(4-fluorophenyl)-N-(4-((6-hydroxy-7-methoxyquinolin-4-yl)oxy)phenyl)cyclopropane-1,1-dicarboxamide |
| 3 | Int3-Imp5 | N-(4-((6,7-dimethoxyquinolin-4-yl)oxy)phenyl)-N-phenylcyclopropane-1,1-dicarboxamide |
| 4 | Int3-Imp7 | N-(4-((6,7-dimethoxyquinolin-4-yl)oxy)phenyl)-N-(2-fluorophenyl)cyclopropane-1,1-dicarboxamide |
| 5 | Int1 | 4-((6,7-dimethoxyquinolin-4-yl)oxy)aniline |
| 6 | SM1-Imp4 | 3,4-dimethoxyaniline |
| 7 | Int1-Imp1 | 6,7-dimethoxy-4-(4-nitrophenoxy)quinolone |
| 8 | SM2 | 4-aminophenol |
| 9 | SM4 | 4-fluoroaniline |

Int = intermediate;

Imp = impurity

The Stability Results were:

Stability data of Example 25B

| Condition: 40° C./75% RH | | Time (months) | | | |
|---|---|---|---|---|---|
| Items | | 0 | 1 | 3 | 6 |
| Related Substance 1 (%) | Int2-Imp1 | 0.12 | 0.07 | 0.06 | 0.10 |
| | Int3-Imp2 | ND | ND | <0.05 | ND |
| | Int3-Imp5 | <0.05 | <0.05 | <0.05 | <0.05 |
| | Int3-Imp7 | ND | ND | ND | <0.05 |
| | Unidentified imp | 0.06 | ND | ND | <0.05 |
| | Total imp. | 0.20 | 0.09 | 0.11 | 0.10 |
| Related Substance 2 (ppm) | Int1 | 2.77 | 6.28 | 6.50 | 7.34 |
| | Int1-Imp1 | ND | ND | ND | ND |
| | SM2 | ND | ND | ND | ND |
| | SM4 | ND | ND | ND | ND |
| Water Content | | 0.19% | / | 0.10% | / |
| Assay(on anhydrous basis) | | 98.2% | 97.1% | 99.7% | 99.0% |

Stability data of Example 25C

| | | Condition: 40° C./75% RH Time (months) | | | |
|---|---|---|---|---|---|
| Items | | 0 | 1 | 2 | 3 |
| Related Substance 1 (%) | Int2-Imp1 | 0.10 | 0.11 | 0.13 | 0.13 |
| | Int3-Imp2 | ND | ND | ND | ND |
| | Int3-Imp5 | 0.05 | <0.05 | <0.05 | <0.05 |
| | Int3-Imp7 | <0.05 | 0.05 | <0.05 | <0.05 |
| | Unidentified imp | <0.05 | <0.05 | ND | <0.05 |
| | Total imp. | 0.24 | 0.24 | 0.21 | 0.29 |
| Related Substance 2 (ppm) | Int1 | 5.22 | 5.98 | 6.07 | 6.99 |
| | Int1-Imp1 | ND | ND | ND | ND |
| | SM1-Imp4 | ND | ND | ND | ND |
| | SM2 | ND | ND | ND | ND |
| | SM4 | ND | ND | ND | ND |
| Water Content | | 0.31% | 0.29% | 0.068% | 0.05% |
| Assay(on anhydrous basis) | | 100.8% | 101.0% | 100.1% | 99.2% |

Example 26

An oral capsule dosage form in accordance with the present invention was prepared by the method described in Example 5. The composition of the capsule content is as follows:

| | Batch No. CT2203281A Strength 20 mg | |
|---|---|---|
| Ingredient | Mg/capsule | Wt % |
| Cabozantinib Lauryl Sulfate (Lot No S23010801) | 30.59 | 23.42 |
| PEG-32 Stearate (GELUCIRE 48/16) | 100.00 | 76.58 |
| Hard Gelatin Capsule Size | 3# | |
| Total | 130.59 | 100.00 |

The capsules were placed in a 60 mL Huanuno HDPE bottle with 1 gram of desiccant and sealed. The sealed bottles were stored at 40° C. and 7500 relative humidity and periodically tested for impurities and dissolution. The impurities were measured with following chromatographic conditions:

1.1 Chromatographic Conditions

| Parameters | | Setting/Description | | |
|---|---|---|---|---|
| Column | | YMC-Triart C18, 4.6*150 mm, 3 μm | | |
| Injection Volume | | 5 μL | | |
| Mobile phase | A | 0.02M $KH_2PO_4$ (0.1% TEA, adjust pH to 6.0 with $H_3PO_4$) | | |
| | B | Acetonitrile:methanol:water 60:30:10 | | |
| Gradient elution | | Time (min) | Mobile phase A (%) | Mobile phase B (%) |
| | | 0 | 70 | 30 |
| | | 8 | 60 | 40 |
| | | 20 | 40 | 60 |
| | | 25 | 40 | 60 |
| | | 36 | 25 | 75 |
| | | 44 | 20 | 80 |
| | | 53 | 20 | 80 |
| | | 53.5 | 70 | 30 |
| | | 60 | 70 | 30 |
| Flow rate | | 0.8 mL/min | | |
| Detection | | UV at 245 nm | | |
| Column temperature | | 25° C. | | |
| Run Time | | 60 minutes | | |

1.2 Preparation of Solution

Blank Solution: 90% MeOH. Take 900 mL of methanol, add 100 mL of water and mix well.

Standard Stock Solution: Accurately weigh about 18.4 mg of Cabozantinib Laurylsulfate standard (equivalent to 12.0 mg of Cabozantinib) and transfer into a 50-mL volumetric flask. Add 80% full of Diluent, sonicate for 5 minutes to dissolve, cool, then dilute to volume with Diluent and mix well. Transfer 5.0 mL of above solution into a 20-mL volumetric flask and dilute to volume with Diluent and mix well.

Reference Standard Solution: Transfer 2.0 mL of Standard Stock Solution into a 25-mL volumetric flask, and dilute to volume with Diluent, mix well. Transfer 5.0 mL of above solution into a 50-mL volumetric flask and dilute to volume with Diluent and mix well.

Sample Solution: Take ten capsules and carefully open, transfer the contents and the capsule shells into a 200-mL (10 mg or 20 mg strength) or 250-mL (30 mg strength) volumetric flask. Add 80% full of Diluent, sonicate for 20 minutes and stir for 15 minutes, cool, then dilute to volume with Diluent and mix well Quantitatively dilute with Diluent based on the strength in the table below, 0.45p m nylon filter.

For 10 mg: Transfer 5.0 mL of above solution into a 10-mL volumetric flask, and dilute to volume with Diluent and mix well, 0.45p m nylon filter.

For 20 mg: Transfer 5.0 mL of above solution into a 20-mL volumetric flask, and dilute to volume with Diluent and mix well, 0.45p m nylon filter.

For 30 mg: Transfer 5.0 mL of above solution into a 25-mL volumetric flask, and dilute to volume with Diluent and mix well, 0.45p m nylon filter.

The dissolution was measured using a U.S.P. Type II (paddle with a stationary basket) apparatus with 0.01N HCl with 0.375% TRITON™ X-100, 900 mL media, 75 rpm, 37° C.

The stability results were as follows:

| 40° C./75% RH | | T0 | | 1M | | 3M | | 6M | |
|---|---|---|---|---|---|---|---|---|---|
| Appearance | | Complies | | Complies | | Complies | | Complies | |
| Assay | | 97.4% | | 97.5% | | 100.6% | | 101.3% | |
| Max Individuals | | 0.07% | | 0.06% | | 0.06% | | 0.07% | |
| Total Impurities | | 0.11% | | 0.17% | | 0.16% | | 0.24% | |
| | Time (min) | Avg. | % RSD | Avg. | % RSD | Avg. | % RSD | Avg. | % RSD |
| Dissolution (%) | 15 | 38.2 | 7.9 | 35.5 | 17.3 | 37.4 | 8.3 | 42.4 | 5.1 |
| | 20 | 56.9 | 5.7 | 52.1 | 14.0 | 55.6 | 7.2 | 63.1 | 4.8 |
| | 30 | 84.6 | 2.3 | 78.6 | 10.0 | 84.1 | 4.3 | 92.7 | 3.7 |
| | 45 | \ | \ | 99.3 | 1.7 | 100.6 | 2.6 | 101.6 | 2.8 |
| | 60 | 100.4 | 2.1 | 100.9 | 2.1 | 100.9 | 2.2 | 101.9 | 3.0 |

Example 27

An oral capsule dosage form in accordance with the present invention was prepared by the method described in Example 5. The composition of the capsule content is as follows:

| Example | | 27A | 27B | 27C |
|---|---|---|---|---|
| Batch No. | | CT2305233 | T230701 | CT230919 |
| Hard Gelatin Capsule Size | | 1# | 1# | 3# |
| Strength | | | 30 mg | |
| Ingredient | | | Mg/capsule (Wt %) | |
| Cabozantinib | Lot No. S23051201 | 45.94 (18.68) | — | — |
| Lauryl Sulfate | Lot No. KABTN230601Z | — | 45.94 (18.68) | — |
| | Lot No. KABTN230801Z | — | — | 45.94 (18.68) |
| PEG-32 Stearate (GELUCIRE 48/16) | | 200.00 (81.32) | 200.00 (81.32) | 200.00 (81.32) |
| Total | | | 245.94 (100.00) | |

The capsules of Example 27A, 27B and 27C were placed in a 60 mL Huanuno HDPE bottle with 1 gram of desiccant and sealed. The sealed bottles were stored at 40° C. and 75% relative humidity and periodically tested for impurities and dissolution.

The impurities of Example 27A, 27B and 27C were measured with the chromatographic conditions as follows:

1.1 Chromatographic Conditions

| Parameters | | Setting/Description | | |
|---|---|---|---|---|
| Column | | Waters XSelect CSH C18, 150*4.6 mm, 3.5 μm | | |
| Injection Volume | | 20 μL | | |
| Mobile phase | A | 0.02M $KH_2PO_4$ (0.1% TEA) | | |
| | B | Acetonitrile:methanol 80:20 | | |
| Gradient elution | | Time (min) | Mobile phase A (%) | Mobile phase B (%) |
| | | 0 | 90 | 10 |
| | | 8 | 80 | 20 |
| | | 15 | 70 | 30 |
| | | 40 | 40 | 60 |
| | | 45 | 20 | 80 |
| | | 50 | 20 | 80 |
| | | 51 | 90 | 10 |
| | | 60 | 90 | 10 |
| Flow rate | | 0.8 mL/min | | |
| Detection | | UV at 239 nm | | |
| Column temperature | | 25° C. | | |
| Run Time | | 60 minutes | | |

1.2 Preparation of Solution

Blank Solution: 9000 MeOH. Take 900 mL of methanol, add 100 mL of water and mix well.

Int1/Int1-Imp1/SM2/SM4 Impurity Stock Solution: Accurately weigh about 15 mg of Int1/Int1-Imp1l/SM2/SM4 impurity standard and transfer into a 100-mL volumetric flask. Add 80% full of Diluent, sonicate for 5 minutes to dissolve, cool, then dilute to volume with Diluent and mix well.

Reference Standard Solution: Transfer 1.0 mL of Int1 Impurity Stock Solution, Int1-Imp1 Impurity Stock Solution, SM2 Impurity Stock Solution and SM4 Impurity Stock Solution respectively into a same 100-mL volumetric flask, dilute to the volume with Diluent and mix well. Transfer 2.0 mL of above Solution into a 10-mL volumetric flask, dilute to the volume with Diluent and mix well.

Sample Solution: Take 12 (10 mg strength) or 6 (20 mg strength) or 4 (30 mg strength) capsules and carefully open, weigh about 984 mg of the contents (equivalent to about 120 mg of cabozantinib) and transfer into a 10-mL volumetric flask. Add 80% full of Diluent, sonicate for 20 minutes to dissolve, cool, then dilute to volume with Diluent and mix well, 0.45 μm Nylon66 filter.

The stability results of Example 27A were as follows:

The dissolution was measured using a U.S.P. Type II (paddle with a stationary basket) apparatus with 0.01N HCl with 0.25% TRITON™ X-100, 900 mL media, 75 rpm, 37° C.

| 40° C./75% RH | | T0 | | 1M | | 2M | | 3M | |
|---|---|---|---|---|---|---|---|---|---|
| Appearance | | Complies | | Complies | | Complies | | Complies | |
| Assay | | 105.1% | | 102.0% | | 100.2% | | 102.7% | |
| Max Individuals | | 0.13% | | 0.08% | | 0.09% | | 0.05% | |
| Total Impurities | | 0.13% | | 0.08% | | 0.09% | | 0.05% | |
| Related | Int 1 | 26.36 ppm | | 52.08 ppm | | 63.71 ppm | | 67.39 ppm | |
| Substance | SM4 | ND | | 9.3 ppm | | 14.5 ppm | | 16.53 ppm | |
| 2 (ppm) | SM2 | / | | ND | | ND | | ND | |
| | Time (min) | Avg. | % RSD | Avg. | % RSD | Avg. | % RSD | Avg. | % RSD |
| Dissolution | 15 | 35.8 | 5.6 | 36.0 | 9.1 | 36.9 | 6.1 | 38.7 | 10.9 |
| (%) | 20 | 50.2 | 3.8 | 51.3 | 8.0 | 52.4 | 5.2 | 53.9 | 8.3 |
| | 30 | 73.5 | 1.4 | 77.0 | 6.4 | 76.5 | 4.5 | 79.5 | 5.1 |
| | 45 | 97.5 | 1.7 | 99.1 | 3.0 | 96.4 | 1.7 | 97.9 | 1.3 |
| | 60 | 100.8 | 0.9 | 101.2 | 1.0 | 98.1 | 0.9 | 99.0 | 1.4 |

The stability results of Example 27B were as follows:

The dissolution was measured using a U.S.P. Type II (paddle with a stationary basket) apparatus with 0.01N HCl with 0.25% TRITON™ X-100, 900 mL media, 75 rpm, 37° C.

| 40° C./75% RH | | T0 | | 1M | | 3M | |
|---|---|---|---|---|---|---|---|
| Appearance | | Complies | | Complies | | Complies | |
| Assay | | 99.7% | | 97.4% | | 101.6% | |
| Max Individuals | | 0.07% | | 0.08% | | 0.11% | |
| Total Impurities | | 0.07% | | 0.08% | | 0.11% | |
| Related | Int 1 | 8.42 ppm | | 8.80 ppm | | 18.04 ppm | |
| Substance | SM4 | ND | | ND | | ND | |
| 2 (ppm) | SM2 | ND | | ND | | ND | |
| | Time (min) | Avg. | % RSD | Avg. | % RSD | Avg. | % RSD |
| Dissolution | 15 | 38.7 | 9.9 | 32.9 | 3.2 | 36.3 | 8.1 |
| (%) | 20 | 56.6 | 7.0 | 51.7 | 3.5 | 53.8 | 5.0 |
| (Apparatus II) | 30 | 78.3 | 2.4 | 76.9 | 2.1 | 77.7 | 2.3 |
| | 45 | 88.4 | 0.8 | 89.9 | 1.3 | 90.2 | 1.1 |
| | 60 | 91.0 | 0.8 | 93.6 | 1.2 | 94.2 | 1.2 |

The stability results of Example 27C were as follows:

The dissolution was measured using a U.S.P. Type II (paddle with a stationary basket) apparatus with 0.01N HCl with 0.375% TRITON™ X-100, 900 mL media, 75 rpm, 37° C.

| 40° C./75% RH | | T0 | | 1M | |
|---|---|---|---|---|---|
| Appearance | | Complies | | Complies | |
| Assay | | 99.1% | | 101.6% | |
| Max Individuals | | 0.10% | | 0.11% | |
| Total Impurities | | 0.16% | | 0.11% | |
| Related | Int 1 | 4.85 ppm | | 5.43 ppm | |
| Substance | SM4 | ND | | ND | |
| 2 (ppm) | SM2 | ND | | ND | |
| Dissolution (%) | Time (min) | Avg. | % RSD | Avg. | % RSD |
| | 10 | 20.7 | 4.7 | 21.2 | 10.9 |
| | 15 | 46.0 | 5.1 | 42.9 | 8.9 |
| | 20 | 68.2 | 2.7 | 63.1 | 5.7 |
| | 30 | 93.1 | 0.9 | 90.0 | 2.2 |
| | 45 | 100.2 | 0.9 | 100.3 | 1.0 |
| | 60 | 101.8 | 1.0 | 101.1 | 0.7 |

Example 28

Capsules in accordance with the present invention were prepared according to the procedure outlined in Example 5 and administered to Wistar rats in a multiple dose adverse event study. The composition of the Test capsule in accordance with the present invention was as follows:

| | Batch No. CT2307051 Strength 1 mg | |
|---|---|---|
| Ingredient | mg/cap | % |
| Cabozantinib Laurylsulfate | 1.53 | 18.67 |
| PEG-32 Stearate (Gelucire 48/16) | 6.67 | 81.30 |
| Hard Gelatin Capsule | 20 uL small animal capsules | |
| SUM | 8.20 | 100.0 |

The Wister rates were also administered one of two comparative reference compositions. The comparative reference compositions were prepared by removing the outer coating from a commercially available CABOIVETYX® tablet, crushing the uncoated tablet and filling the crushed material into 20 µl small animal capsules. The reference capsules contained with 1.5 mg of cabozantinib free base in the form of cabozantinib (S)-malate, hereinafter RLD-1.5 or 2.0 mg of cabozantinib free base in the form of cabozantinib (S)-malate, hereinafter RLD-2. In addition to the cabozantinib (S)-malate, the reference capsules also contain microcrystalline cellulose, lactose anhydrous, hydroxypropyl cellulose, caroscarmellose sodium, colloidal silicon dioxide and magnesium stearate based on the description provided with the CABOMETYX® tablet package insert.

The Wister rats used in the study were female, specific pathogen-free (SPF), that weighed about 190 g at the time of the first dosing. Prior to dosing the rats were acclimated for 25 days to the animal room conditions of 20-25° C., 40-70% relative humidity and 12-hours light/12-hours dark cycles. SPF mouse growth breeding feed was provided ad libitum throughout the in-life part of the study. Reverse osmosis water was available ad libitum.

After the acclimation period, 30 rats weighing and randomly divided into 3 groups of 10 as follows:

| Group | Treatment | Dose (mg/kg) (190 g/rat) | Capsule Strength (mg free base drug per capsule) | Dosage (capsule/rat) | Route of admin. |
|---|---|---|---|---|---|
| 1 | RLD-2 | 10 | 2.0 | 1 | ig. qd. 35 days |
| 2 | RLD-1.5 | 7.5 | 1.5 | 1 | ig. qd. 35 days |
| 3 | Test | 5 | 1.0 | 1 | ig. qd. 35 days |

According to the table above, the Test and Reference capsules were administered via oral gavage once a day for 35 days. The animals were fasted 4 hours before the dosing and fasted 2 hours after the dosing. Water was offered normally all through the day.

The weight of the rats was recorded daily. The food intake was monitored and recorded twice a day. The blood pressure was measured every 3 days. Diarrhea scores were recorded twice a day. The number of animal deaths and diarrhea in each group was observed and the date of death was recorded.

At the end of the study, all animals were euthanized by inhalation of excess $CO_2$ and the entire stomach tissue, whole small intestine and the entire colon from the cecum to the anus was removed. The stomach was cut open along the greater curvature and the intestine along the mesentery. The length and weight of the stomach, intestine and colon were measured before and after rising with saline. An ulcer scoring system was used to evaluate erosion at necropsy in stomach, intestine and colon. The gastrointestinal tissues were fixed with the damaged portions for histopathological examination using 10% formalin.

Diarrhea was scored using the following criteria:

Score 0=firm feces

Score 1=soft feces without staining of fur around anus

Score 2=wet feces with staining around anus

Score 3=very wet feces with staining spreading to legs or involving abdomen.

To elucidate the relationship between the treatment regimens and the safety parameters, the study was underpinned by rigorous data analysis, with statistical significance determined when the P-value is less than 0.05. Statistical analysis was performed using IBM SPSS Statistics 23 and R software (R Foundation for Statistical Computing).

Over the 35 days of administration, the RLD-2 group experienced a total of 28 instances of diarrhea, with 19 recorded as score 1 and 9 as score 2. The RLD-1.5 group experienced a total of 25 instances of diarrhea with 10 recorded as score 1, 14 as score 2 and 1 as score 3. The Test group experienced a total of 10 instances of diarrhea, with 7 recorded as score 1 and 3 as score 2.

Onset of diarrhea was observed at day 4 for the RLD-2 group, day 7 for the RLD-1.5 and day 4 for the Test group.

When assessing diarrhea data between groups, several analysis methods were utilized to ascertain if there were significant differences in the occurrence, frequency, and severity of diarrhea across the treatment groups. Primarily, Time-To-Event (TTE) analyses, considering both occurrence and severity, were the main method employed for this evaluation. TTE analyses were performed using R with a survival package. Given that the diarrhea was monitored twice daily, "Days" was used as the time variable with half day increments. Since the diarrhea was graded in three levels, the events were identified in three ways: (1) diarrhea scores were equal to or greater than 1; (2) diarrhea scores were equal to or greater than 2; and (3) diarrhea scores were equal to 3. Kaplan-Meir curves were obtained for diarrhea scores. The P-values for the log-rank test identified the significance of the difference. The analyses revealed a statistically significant difference between the test group and both RLD-2 and RLD-1.5 group regarding diarrhea scores equal to or more than 1. The analyses also revealed a statistically significant difference between the test group and both RLD-2 and RLD-1.5 groups regarding diarrhea scores equal to or more than 2.

Figure 12A:
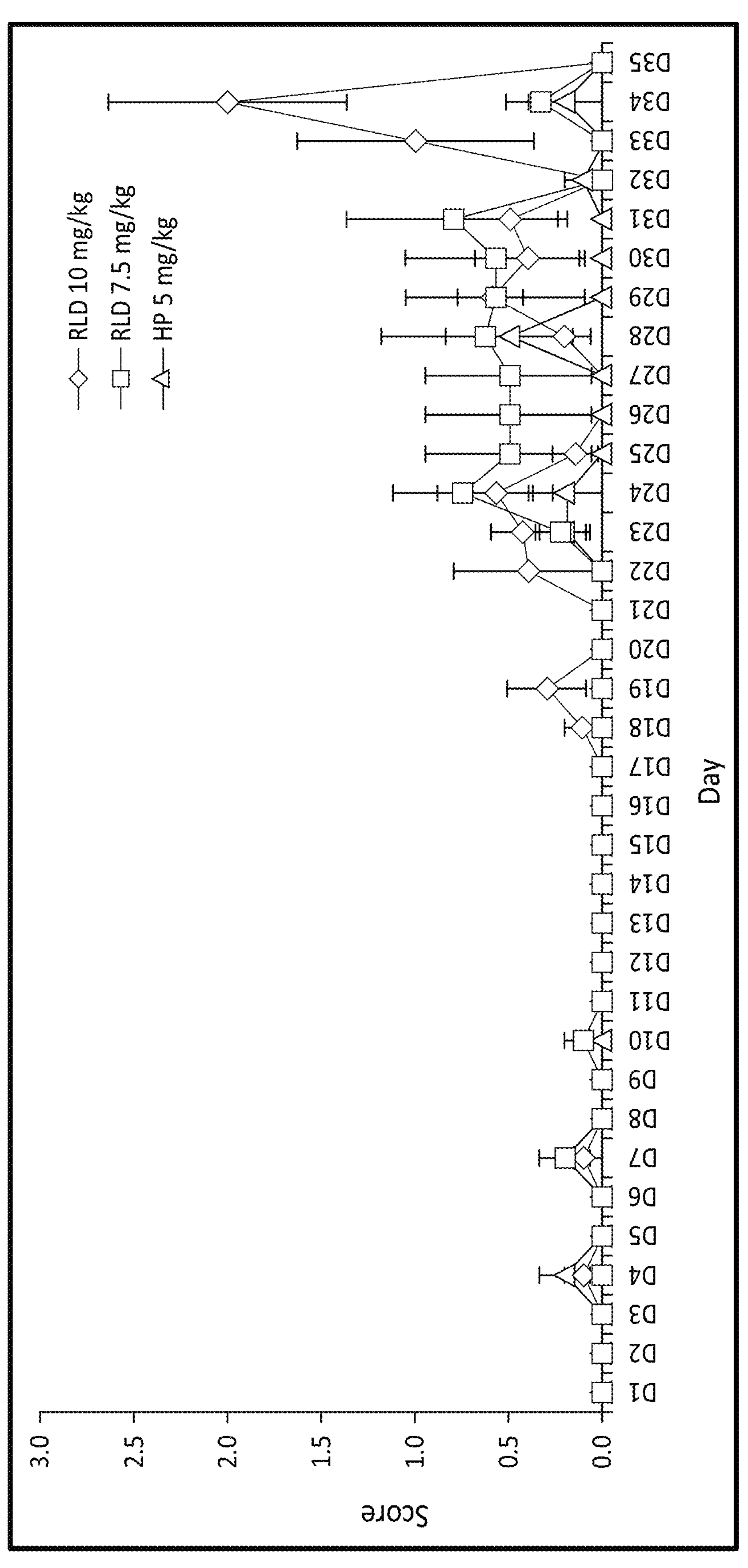
FIGS. 12A and 12B are graphs of the mean diarrhea score and rate from the study described in Example 28.
Figure 12B:
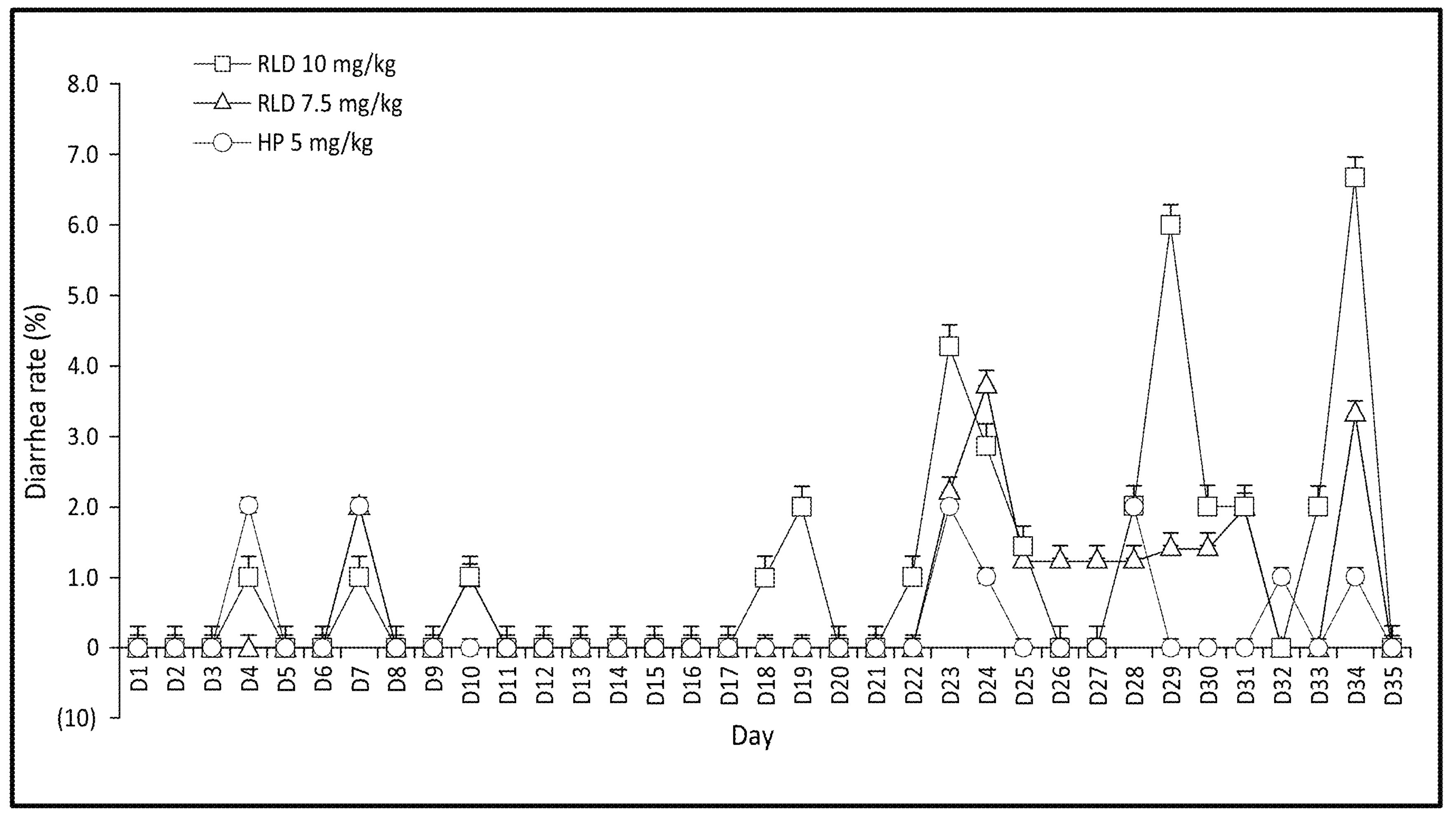

The diarrhea scores and rates were calculated throughout the study and shown in FIGS. 12A and 12B. The following table shows the diarrhea rates (%) on day 34 and the overall average rate per day:

| Treatments | Day 34 | x bar ± s (%) |
|---|---|---|
| RLD-2 (10 mg/kg) | 67% | 10.4 ± 16.8 |
| RLD-1.5 (7.5 mg/kg) | 33% | 6.3 ± 10.2 |
| Test (5 mg/kg) | 10% | 3.1 ± 6.8 |

Ulcers are damages in a mucous membrane, such as the one lining the stomach or duodenum, accompanied by inflammation, pus, and loss of tissue. Ulcer scores and ulcer areas represent the severity and the extent of the damage as summarized in the following tables:

| Ulcer Scoring in the GI Tissues (x bar ± s, n = 10) | | | |
|---|---|---|---|
| | Stomach | Intestine | Colon |
| RLD-2 | 3.9 ± 1.4 | 4.5 ± 0.5** | 0 ± 0 |
| RLD-1.5 | 3.7 ± 1.4 | 4.4 ± 0.5* | 0 ± 0 |
| Test | 3.4 ± 1.8 | 3.6 ± 0.7 | 0 ± 0 |

*P < 0.05 vs Test;
**P < 0.01 vs Test

| Ulcer Area in the GI Tissues (x bar ± s, n = 10) | | | |
|---|---|---|---|
| | Stomach | Intestine | Colon |
| RLD-2 | 84.8 ± 107.6 | 106.8 ± 74.5* | 0 ± 0 |
| RLD-1.5 | 40.9 ± 29.1 | 93.1 ± 65.1* | 0 ± 0 |
| Test | 31.6 ± 19.0 | 19.0 ± 19.3 | 0 ± 0 |

*P < 0.01 vs Test

As shown by the above tables there was a significant difference in the ulcer score and ulcer area in the duodenum (intestine) between the Test group and the RLD-2 and RLD-1.5 groups. There were no significant differences for the ulcer score or ulcer area for the stomach and colon between all groups, however, the Test group exhibited a lower ulcer score and smaller ulcer area for the stomach.

No mortality was observed in the Test group throughout the study. In the RLD-2 group deaths commenced at day 23, reached 50% at day 26 and escalated to 80% by day 35, with only two (2) rats surviving to the end of the experiment. In the RLD-1.5 group mortality started at day 22, with a 20% mortality rate at day 24 to day 28 and a 70% mortality rate at day 35. The statistical analysis revealed a significantly lower mortality rate ($P<0.001$) in the Test group compared to both the RLD-2 and RLD-1.5 groups.

There was a decrease in body weight for all groups on days 1 and 2 followed by an upward trend starting from day 2. The upward trend ended on day 13 for the RLD-2 group, day 11 for the RLD-1.5 group and day 24 for the Test group. The body weight of the Test group was significantly higher (differed ($P<0.01$)) from the RLD-2 from day 17 to the end of the study. The body weight of the Test group also significantly higher (differed ($P<0.001$)) from the RLD-1.5 group from day 14 to the end of the study. The body weight of the RLD-1.5 group was higher (differed ($P<0.001$)) than the RLD-2 group from days 27 to day 34.

The average food intake of the Test group was statistically significantly higher than that of the RLD-2 group ($P<0.001$) and the RLD-1.5 group ($P<0.005$), while no statistically significant difference was observed in the food intake between the RLD-2 and RLD-1.5 groups.

Before washing, the weights of the stomach, intestine and colon of the animals in the RLD-1.5 group were lower than that of the RLD-2 group and the Test group, with the weight of the colon being statistically significantly lower (P<0.05) than that of the Test group. There was no statistically significant difference in the weights of the stomach, intestine, and colon of the rats between the RLD-2 group and the Test group as well as between the RLD-1.5 group and the Test group before washing.

After washing, the weights of the stomach and colon in the Test group were statistically significantly heavier (P<0.05) than that of the RLD-1.5 group. There was no statistically significant difference in the weights of the stomach, intestine, and colon of the animals between the RLD-2 group and the Test group, and also no statistically significant difference between the RLD-2 group and the RLD-1.5 group after washing.

There was no significant difference in the length of the intestine and colon among the RLD-2, RLD-1.5 and Test groups.

The systolic blood pressure (SBP) of all three groups showed an increase from day 1 to day 4, followed by an overall decrease from day 4 until the end of the experiment. Specifically, the SBP of the RLD-1.5 group was statistically significantly lower than that of the RLD-2 group at day 22, and statistically significantly lower than that of the Test group at day 16, 22, 25 and 28. Moreover, the SBP of the RLD-2 group was statistically significantly lower than that of the Test group at day 34. The diastolic blood pressure (DBP) of the RLD-1.5 group and the Test group increased from day 1 to day 4, while the DBP of the RLD-2 group increased from day 1 to day 7. However, for all three groups, the trend from the point of highest DBP to the experiment's end showed a consistent decrease, mirroring the SBP trend. Specifically, the DBP of the RLD-1.5 group was statistically significantly higher than that of the RLD-2 group at day 4 but transitioned to statistically significantly lower than that of the RLD-2 group at day 22. Notably, the DBP of the Test group was statistically significantly higher than that of the RLD-2 group a day 4 and day 28, and statistically significantly higher than that of the RLD-1.5 group at days 22 and 28.

It has been determined the Test capsule exhibits about a 50% higher bioavailability than the commercially available CABOMETYX® tablet, with the Test capsule being bioequivalent to the RLD-1.5 capsule. That data presented above shows superior performance of the dosage forms of the present invention compared to commercially available cabozantinib (S)-malate oral compositions including significant advantages in reducing diarrhea rate, ulcer severity and mortality rates. Accordingly, the dosage forms of the present invention provide enhanced safety compared to commercially available cabozantinib (S)-malate oral compositions.

It is believed the reduced and unnecessary exposure of a subject to cabozantinib that occurs with the dosage forms of the present invention due to the increased bioavailability, results in a reduction of adverse events occurrence as well as adverse events severity including but not limited to gastrointestinal perforations and/or fistula, diarrhea, abdominal pain, dyspepsia, decreased appetite, hypertension and weight loss.

Example 29

A low dose cabozantinib capsule dosage form, with at least about 30% dose reduction, i.e. 70% of cabozantinib free base, compared to commercially available CABOMETYX® tablets, was prepared by melting the carriers (exhibits a melting point between 30° C. to 60° C.) in water bath (under 60° C.) to obtain a solution. Cabozantinib lauryl sulfate was added into the solution to obtain an intimate mixture as a uniform dispersion or coagulate into a semi-solid. The semi-solid suspension was filled into a hard gelatin capsule.

The composition of the capsule content is as follows:

| Materials | Preferred wt % | More preferred wt % | Most preferred wt % |
|---|---|---|---|
| Cabozantinib Lauryl Sulfate | 5-50 | 10-30 | 15-25 |
| Carrier with an HLB value of 10 or greater | 40-95 | 55-90 | 60-90 |
| Carrier with HLB value of less than 10 | 0-40 | 0-30 | 0-20 |
| Optionally one or more additional pharmaceutically acceptable excipients | 0-30 | 0-20 | 0-10 |

The composition of the capsule content of a low dose cabozantinib capsule dosage form equivalent to 20 mg strength CABOMETYX® tablets is as follows:

| Materials | Preferred mg | More preferred mg | Most preferred mg |
|---|---|---|---|
| Cabozantinib Lauryl Sulfate | 8-28 | 10-25 | 12-23 |
| Carrier with an HLB value of 10 or greater | 30-120 | 40-110 | 50-100 |
| Carrier with HLB value of less than 10 | 0-50 | 0-40 | 0-30 |
| Optionally one or more additional pharmaceutically acceptable excipients | 0-50 | 0-40 | 0-30 |
| Total Weght per dosage form | 50-150 | 55-135 | 65-125 |

The composition of the capsule content of a low dose cabozantinib capsule dosage form equivalent to 40 mg strength CABOMETYX® tablets is as follows:

| Materials | Preferred mg | More preferred mg | Most preferred mg |
|---|---|---|---|
| Cabozantinib Lauryl Sulfate | 15~55 | 20-50 | 22-46 |
| Carrier with an HLB value of 10 or greater | 60-240 | 80-220 | 100-200 |
| Carrier with HLB value of less than 10 | 0-80 | 0-60 | 0-40 |
| Optionally one or more additional pharmaceutically acceptable excipients | 0-80 | 0-60 | 0-40 |
| Total Weght per dosage form | 100-300 | 110-270 | 130-250 |

The composition of the capsule content of a low dose cabozantinib capsule dosage form equivalent to 60 mg strength CABOMETYX® tablets is as follows:

| Materials | Preferred mg | More preferred mg | Most preferred mg |
|---|---|---|---|
| Cabozantinib Lauryl Sulfate | 25-85 | 30-75 | 35-70 |
| Carrier with an HLB value of 10 or greater | 100-350 | 130-330 | 150-300 |
| Carrier with HLB value of less than 10 | 0-100 | 0-80 | 0-50 |
| Optionally one or more additional pharmaceutically acceptable excipients | 0-100 | 0-80 | 0-50 |
| Total Weght per dosage form | 150-450 | 170-420 | 190-380 |

The low dose cabozantinib capsule dosage form exhibits one of the following:

(a) the oral administration of the low dose cabozantinib capsule dosage form allows for at least about a 10%, 15%, 20%, 25%, 30%, 35%, 40%, 45% or 50% dose reduction in the total daily dose of cabozantinib compared to the currently U.S. FDA approved CABOMETYX® tablets;

(b) the oral administration of the low dose cabozantinib capsule dosage form may be with or without food;

(c) when administered in the fed versus the fasted condition, the difference in $C_{max}$ and/or AUC is less than 40%, less than 35%, less than 30%, less than 25%, less than 20%, less than 15%, less than 10%;

(d) the oral administration of the low dose cabozantinib capsule dosage form to fed and/or fasted subjects produce a coefficient of variation in AUC is less than 40%, less than 35%, less than 30%, less than 25%, less than 20%, less than 15%, less than 10% and/or produce a coefficient of variation in $C_{max}$ is less than about 50% less than 45%, less than 40%, less than 35%, less than 30%, less than 25%, less than 20%, less than 15%, less than 10%;

(e) the oral administration of the low dose cabozantinib capsule dosage form exhibits an bioavailability increase of at least 20%, 25%, 30% 35% or 40% compared to the currently U.S. FDA approved CABOMETYX® tablets;

(f) the oral administration of the low dose cabozantinib capsule dosage form will reduce the occurrence of one or more adverse reactions compared to the commercially available CABOMETYX® tablets;

(g) the oral administration of the low dose cabozantinib capsule dosage form will reduce the occurrence of one or more Grade 2-4 adverse reactions;

(h) the oral administration of the low dose cabozantinib capsule dosage form will reduce the occurrence of dose interruption and/or dose reduction resulted from adverse reactions; and (i) the oral administration of the low dose cabozantinib capsule dosage form will exhibit a combination of the foregoing.

The invention illustratively described herein suitably may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A crystalline cabozantinib lauryl sulfate salt characterized by an x-ray powder diffraction (XRPD) pattern with 2θ peaks at 5.0±0.2, 12.1±0.2, 19.1±0.2, and 24.5±0.2.

2. The crystalline cabozantinib lauryl sulfate salt of claim 1 further comprising one or more XRPD 2θ peaks selected from the group consisting of 20.3±0.2, 21.4±0.2, 22.0±0.2, 22.8±0.2, and 23.3±0.2.

3. The crystalline cabozantinib lauryl sulfate salt of claim 1 comprising XRPD 2θ peaks at 5.0±0.2, 12.1±0.2, 19.1±0.2, 20.3±0.2, 21.4±0.2, 22.0±0.2, 22.8±0.2, 23.3±0.2 and 24.5±0.2.

4. A pharmaceutical dosage form comprising the crystalline cabozantinib lauryl sulfate salt of claim 1 and one or more pharmaceutical excipients.

5. A pharmaceutical dosage form comprising the crystalline cabozantinib lauryl sulfate salt of claim 2 and one or more pharmaceutical excipients.

6. A pharmaceutical dosage form comprising the crystalline cabozantinib lauryl sulfate salt of claim 3 and one or more pharmaceutical excipients.

* * * * *